United States Patent
Landers et al.

(10) Patent No.: US 11,135,583 B2
(45) Date of Patent: Oct. 5, 2021

(54) DEVICES AND METHODS FOR EXTRACTION, SEPARATION AND THERMOCYCLING

(71) Applicant: University of Virginia Patent Foundation, Charlottesville, VA (US)

(72) Inventors: James P. Landers, Charlottesville, VA (US); Jacquelyn A. DuVall, Raleigh, NC (US); Delphine Le Roux, Barboursville, VA (US); Brian Root, Charlottesville, VA (US); Daniel Mills, Charlottesville, VA (US); Daniel A. Nelson, Charlottesville, VA (US); An-Chi Tsuei, Charlottesville, VA (US); Brandon L. Thompson, Charlottesville, VA (US); Jingyi Li, Charlottesville, VA (US); Christopher Birch, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 528 days.

(21) Appl. No.: 15/768,115

(22) PCT Filed: Oct. 13, 2016

(86) PCT No.: PCT/US2016/056906
§ 371 (c)(1),
(2) Date: Apr. 13, 2018

(87) PCT Pub. No.: WO2017/066485
PCT Pub. Date: Apr. 20, 2017

(65) Prior Publication Data
US 2018/0304253 A1    Oct. 25, 2018

Related U.S. Application Data

(60) Provisional application No. 62/241,043, filed on Oct. 13, 2015, provisional application No. 62/241,049, (Continued)

(51) Int. Cl.
*B01L 99/00* (2010.01)
*B01L 3/00* (2006.01)
(Continued)

(52) U.S. Cl.
CPC ..... *B01L 3/50273* (2013.01); *B01L 3/502753* (2013.01); *B01L 7/52* (2013.01);
(Continued)

(58) Field of Classification Search
None
See application file for complete search history.

(56) References Cited

U.S. PATENT DOCUMENTS

| 6,761,766 B2 | 7/2004 | David |
| 6,916,372 B2 | 7/2005 | David |

(Continued)

FOREIGN PATENT DOCUMENTS

| CN | 1953802 B | 10/2011 |
| EP | 1862792 A2 | 12/2007 |

(Continued)

OTHER PUBLICATIONS

"International Application Serial No. PCT/US2016/056906, International Search Report dated Mar. 17, 2017", 6 pgs.
(Continued)

*Primary Examiner* — Paul S Hyun
(74) *Attorney, Agent, or Firm* — Schwegman Lundberg & Woessner, P.A.

(57) ABSTRACT

A method to extract, amplify and separate nucleic acid in a microfluidic device having a plurality of chambers and
(Continued)

channels can include a) introducing cells having nucleic acid to a first chamber of the microfluidic device and subjecting the cells in the first chamber to conditions that lyse the cells. The method can further include b) subjecting the first chamber to centrifugal force, thereby allowing the lysate or a portion thereof having nucleic acid to be distributed to a second chamber through a first channel in the microfluidic device. The method can also include c) combining the lysate or the portion thereof and reagents for amplification of the nucleic acid, thereby providing a second mixture. The method can also include d) subjecting the second chamber to centrifugal force, thereby allowing gas to be expelled from the second mixture.

9 Claims, 41 Drawing Sheets

Related U.S. Application Data filed on Oct. 13, 2015, provisional application No. 62/241,055, filed on Oct. 13, 2015.

(51) Int. Cl.
  *B01L 7/00* (2006.01)
  *G01N 27/447* (2006.01)
  *G01N 21/07* (2006.01)
  *C12Q 1/00* (2006.01)
  *G01N 21/00* (2006.01)

(52) U.S. Cl.
  CPC ............... *C12Q 1/00* (2013.01); *G01N 21/00* (2013.01); *G01N 21/07* (2013.01); *G01N 27/447* (2013.01); *G01N 27/44791* (2013.01); *B01L 2200/0621* (2013.01); *B01L 2200/0647* (2013.01); *B01L 2200/0684* (2013.01); *B01L 2200/10* (2013.01); *B01L 2200/12* (2013.01); *B01L 2200/16* (2013.01); *B01L 2300/0803* (2013.01); *B01L 2300/0816* (2013.01); *B01L 2300/0887* (2013.01); *B01L 2300/1822* (2013.01); *B01L 2300/1844* (2013.01); *B01L 2400/0409* (2013.01); *B01L 2400/0421* (2013.01); *B01L 2400/0424* (2013.01); *G01N 2201/064* (2013.01)

(56) References Cited

U.S. PATENT DOCUMENTS

| | | | |
|---|---|---|---|
| 7,935,318 B2 | 5/2011 | Harding | |
| 8,030,057 B2 | 10/2011 | Linder et al. | |
| D672,467 S | 12/2012 | Smith et al. | |
| 2002/0137218 A1* | 9/2002 | Mian | B01F 13/00 436/45 |
| 2003/0143637 A1 | 7/2003 | Selvan et al. | |
| 2003/0015491 A1 | 8/2003 | David | |
| 2005/0109396 A1* | 5/2005 | Zucchelli | F16K 99/003 137/67 |
| 2007/0286773 A1* | 12/2007 | Schlautmann | G01N 27/44791 422/68.1 |
| 2008/0058991 A1 | 3/2008 | Lee et al. | |
| 2008/0199930 A1* | 8/2008 | Lee | C12N 13/00 435/173.1 |
| 2009/0035847 A1* | 2/2009 | Cho | B01F 15/0233 435/289.1 |
| 2009/0104643 A1 | 4/2009 | Bartholomeusz | |
| 2011/0143364 A1 | 6/2011 | Kim et al. | |
| 2011/0176963 A1 | 7/2011 | Kim et al. | |
| 2013/0217026 A1 | 8/2013 | Egan et al. | |

FOREIGN PATENT DOCUMENTS

| | | |
|---|---|---|
| EP | 1567796 B1 | 5/2008 |
| EP | 1988381 A1 | 11/2008 |
| EP | 2026074 A2 | 2/2009 |
| EP | 1939629 A3 | 3/2011 |
| WO | WO-9824544 A1 | 6/1998 |
| WO | WO-2004058406 A2 | 7/2004 |
| WO | WO-2004113871 A2 | 12/2004 |
| WO | WO-2014058757 A3 | 8/2014 |
| WO | WO-2017066485 A1 | 4/2017 |

OTHER PUBLICATIONS

"International Application Serial No. PCT/US2016/056906, Invitation to Pay Add'l Fees and Partial Search Report dated Jan. 16, 2017", 11 pgs.

"International Application Serial No. PCT/US2016/056906, Written Opinion dated Mar. 17, 2017", 13 pgs.

* cited by examiner

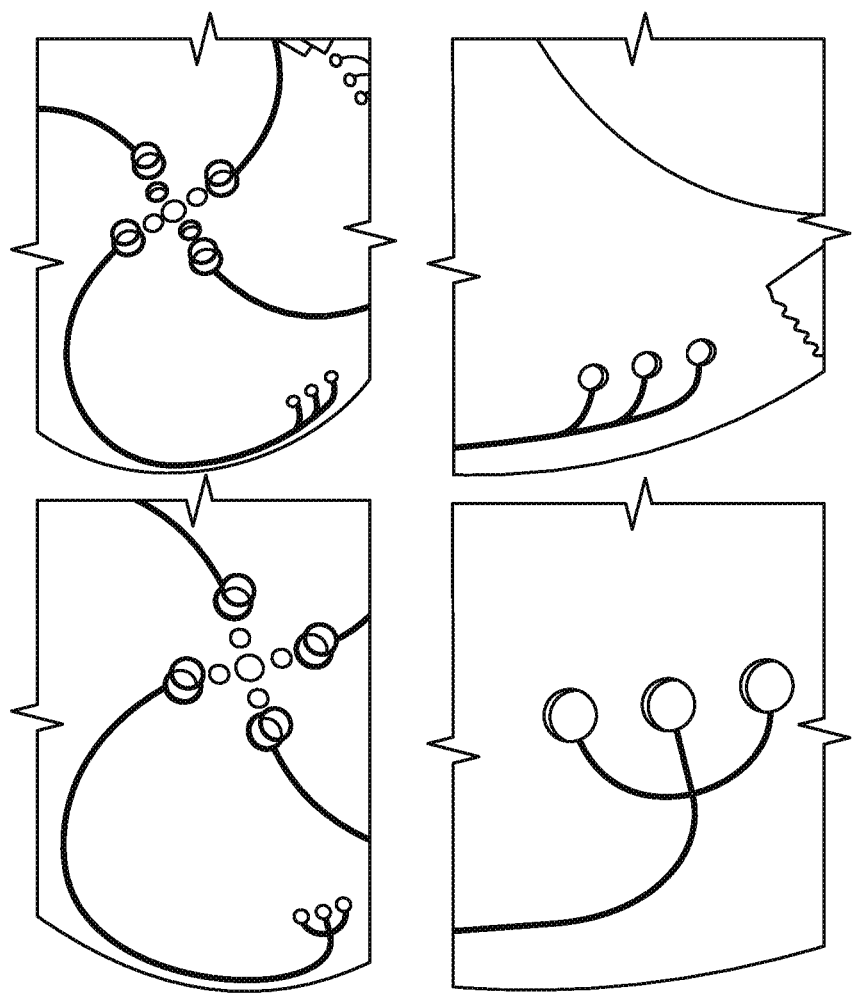
FIG. 14
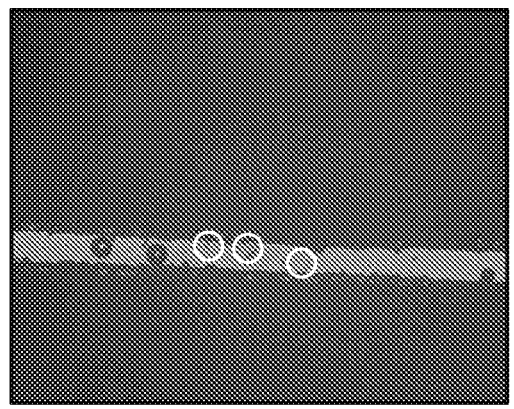 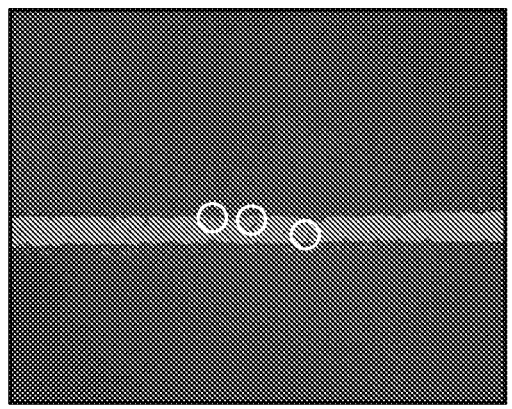
FIG. 15A          FIG. 15B

FIG. 23A   FIG. 23B

DEVICES AND METHODS FOR EXTRACTION, SEPARATION AND THERMOCYCLING

CROSS-REFERENCE TO RELATED APPLICATIONS

This application is a U.S. National Stage Filing under 35 U.S.C. 371 from International Application No. PCT/US2016/056906, filed on Oct. 13, 2016, and published as WO 2017/066485, which claims the benefit of the filing date of U.S. application Ser. No. 62/241,043, filed on Oct. 13, 2015, U.S. application Ser. No. 62/241,049, filed on Oct. 13, 2015, and U.S. application Ser. No. 62/241,055, filed on Oct. 13, 2015, the benefit of each of which are hereby presently claim and the entireties each of which are hereby incorporated by reference herein.

STATEMENT REGARDING FEDERALLY SPONSORED RESEARCH OR DEVELOPMENT

This invention was made with government support under Grant No. N00421-14-2-0003, awarded by the Office of Naval Research. The government has certain rights in the invention.

BACKGROUND

Forensic laboratories heavily rely on successful liberation of the DNA from cells followed by DNA purification, as these are precursors to obtaining the primary form of DNA evidence used in criminal cases, or short tandem repeat (STR) profiles. Most commonly, buccal swabs are substrates used for DNA processing as analysts search for traces of DNA on submitted pieces of evidence. At the present time, small cuttings are taken from each sample and chemically lysed in a chaotropic solution at an elevated temperature (56° C.) for a minimum of 30 minutes. During this step, the cells are desorbed from the swab and cells disrupted, causing the release of DNA into the solution. Once finished, these samples are transferred to a robot instrument, such as a Qiagen EZ1, which performs a solid-phase extraction in approximately 20 minutes. A conventional solid phase extraction requires 3 basic steps: initial binding of the DNA to silica-coated magnetic particles, washing of the beads in an alcohol solution to precipitate the DNA and solubilize contaminants to eliminate any non-specific binding, and elution of the DNA from the silica particles to yield PCR-ready DNA that can be used directly for post processing. External magnets, built into the instrument, move magnetic silica-coated particles through the solution for the initial binding and final elution of the DNA.

Although the lysis method and extraction instruments are fully validated, providing reproducible results for casework, both lend themselves to several limitations such as inefficiency of sample use and non-portability. The maximum volume usable in post processing (i.e. DNA quantitation and amplification) is 12 µL, which accounts for only 6% of the total volume provided from an extraction instrument. Therefore, 90% of the extracted sample volume is more than likely never used, as the remaining 4% may be used for retesting of the sample.

A stand-alone microfluidic device for sample lysis DNA extraction would allow for decreased sample and reagent volumes, reducing the cost per sample and minimizing wasted reagents. Current microfluidic devices, however, require high sample volumes that are not forensically relevant (≥100 µL), require high speeds and complex valving that limits portability, and has not demonstrated multiplexed amplification required for forensic lab DNA testing.

SUMMARY

A portable device for rapid nucleic acid analysis is provided by integrating technologies on a single centrifugal microfluidic device that includes reagent storage and electrophoretic separation on the same centrifugal device.

An aspect of an embodiment provides, among other things, an automated Pe-toner microfluidic device (and related method) on a centrifugal platform for DNA sample lysis and DNA extraction.

An aspect of an embodiment provides, among other things, DNA lysis and extraction on a polyethylene terephthalate (pe) rotationally-driven microdevice and related method thereof.

Thus, a centrifugal microfluidic device that integrates reagent storage, nucleic acid liberation/extraction, multiplexed PCR amplification, electrophoretic separation, and fluorescent detection for rapid and portable nucleic acid analysis is provided, as well as methods of using the device.

In one aspect of the invention, a centrifugal microfluidic device can be configured to prepare a sample for nucleic acid analysis. The centrifugal microfluidic device can include a body, an extraction portion of the body, a reaction portion of the body, a heat and snap-cool portion of the body, and a separation portion of the body. The body can be formed from of a plurality of layers. The extraction portion of the body can include a first reagent storage chamber and a liberation chamber. The reaction portion of the body can include a mixing chamber and a second reagent chamber connected to the mixing chamber. The separation portion of the body can include a polymer loading reservoir and one or more polymer channels and a separation channel connected to the one or more polymer channels and connected to an electrode.

In one aspect of the invention, a method to extract, amplify and separate nucleic acid in a microfluidic device having a plurality of chambers and channels can include a) introducing a sample having nucleic acid to a first chamber of the microfluidic device and subjecting the cells in the first chamber to conditions that lyse the cells. The method can further include b) subjecting the first chamber to centrifugal force, thereby allowing the lysate or a portion thereof having nucleic acid to be distributed to a second chamber through a first channel in the microfluidic device. The method can also include c) combining the lysate or the portion thereof and reagents for amplification of the nucleic acid, thereby providing a second mixture. The method can also included) subjecting the second chamber to centrifugal force, thereby allowing gas to be expelled from the second mixture. The method can include e) subjecting the second mixture in the second chamber to cyclic amplification, thereby providing amplified nucleic acid. The method can further include f) subjecting the second mixture having the amplified nucleic acid to centrifugal force, thereby allowing the amplified nucleic acid to be distributed to a third chamber in the microfluidic device through a second channel, which third chamber reduces the temperature of the amplified nucleic acid to provide denatured nucleic acid. The method can also include g) subjecting the third chamber to centrifugal force, thereby allowing gas to be expelled from the second mixture. The method can additionally include h) combining the amplified nucleic acid in the third chamber with a polymer, thereby providing a fourth mixture. The method can also include i) introducing the fourth mixture into a separation channel using centrifugal force.

In one aspect of the invention, a method of preparing nucleic acid for analysis using a centrifugal microfluidic device can include moving a first reagent from a first reagent chamber to an extraction chamber using centrifugal force. A first fluid can be extracted from a sample cells or nucleic acid by heating the sample in the extraction chamber. The first fluid can be moved to an aliquot chamber using centrifugal force. The first fluid can be moved to a mixing chamber using centrifugal force. A second reagent can be introduced into the mixing chamber through a metering chamber using centrifugal force thereby providing a third fluid. The third fluid can be moved to a reaction chamber using centrifugal force. The third fluid can be degassed using centrifugal force. The third fluid can be moved to a snap-cool chamber using centrifugal force. A third reagent can be moved using centrifugal force to the snap-cool chamber to form a fourth fluid. A polymer can be loaded into a polymer chamber using centrifugal force. The fourth fluid can be mixed with the polymer to create a fifth fluid.

In one aspect of the invention, a device can include a rotating platform, a first thermoelectric heat pump, a second thermoelectric heat pump, and a first fan. The rotating platform can be configured to controllably spin a chip, the rotating platform including a first side and a second side opposing the first side. The first thermoelectric heat pump can be disposed adjacent the first side of the rotating platform. The second thermoelectric heat pump can be disposed adjacent the second side of the rotating platform. The first fan can be adjacent to the first thermoelectric heat pump and can be configured to deliver a first flow of fluid to the rotating platform.

In one aspect of the invention, a chip can be configured for a nucleic acid amplification process and can include a vent, a mixing chamber, a reaction chamber, and a plurality of reagent chambers. The vent can be configured to vent gas. The mixing chamber can be configured to mix and degas a fluid. The polymerase chain reaction chamber can include a first side connected to the vent by a vent channel, and a second side connected to the mixing chamber by a chamber channel. The plurality of reagent chambers can be connected to the mixing chamber by a plurality of reagent channels, and the reagent chambers can have a volume that is larger than a volume of reagents.

In one aspect of the invention, a centrifugal microfluidic device configured for separation of nucleic acids can include a top layer, a middle layer, and a bottom layer. The top layer can be comprised of cyclic olefin copolymer. The top layer can include a first top layer side and a second top layer side opposing the first top layer side. The middle layer can include a first middle layer side that can be configured to mate to the second top layer side, and a second middle layer side opposing the first middle layer side. The bottom layer can be comprised of cyclic olefin copolymer. The bottom layer can include a first bottom layer side that can be configured to mate to the second middle layer side, and a second bottom layer side opposing the first bottom layer side.

In one aspect of the invention, a method of creating a centrifugal microfluidic device configured for separation of nucleic acids can include forming a top layer, forming a middle layer, and forming a bottom layer. Channels and chambers can be ablated into the middle layer. The middle layer can be surrounded with non-bonding layers. Ridges adjacent the channels and the chambers can be re-profiled after ablating the channels and chambers by introducing the middle layer surrounded by the non-bonding layers into a bonding laminator. The top layer and the bottom layer can be bonded to the middle layer. In one aspect of the invention, a chip configured to isolate nucleic acid through a centrifugal process can include a main vent, a recovery vent, a liberation vent, a plurality of storage vents, a first and second valve, a reagent chamber, a liberation chamber, and a recovery chamber. Each vent can be configured to vent gas. The reagent chamber can be connected to the plurality of storage vents and connected to the first valve. The liberation chamber can include a first liberation chamber end connected to the first valve and connected to a liberation vent, and can include a second liberation chamber end connected to the second valve, where the second valve can be connected to the recovery vent. The recovery chamber can include a first recovery side that can be connected to the main vent and a second recovery side that can be connected to the second valve.

In one aspect of the invention, a method of extracting a product using a chip can include pre-loading a reagent into a storage chamber of the chip and opening a liberation chamber of the chip. A swab can be loaded into the liberation chamber and the liberation chamber can be sealed. A storage valve of the chip can be opened and the chip can be spun to release the reagent from the storage chamber into the liberation chamber. The chip can be aligned to a heater and can be heated liberate the product. The recovery valve can be opened and the chip can be spun to separate product from the swab.

In one aspect of the invention, an electrode can include a gold leaf layer, an adhesive layer adhered to the gold leaf layer, and a transparent layer adhered to adhesive layer.

BRIEF DESCRIPTION OF THE FIGURES

FIG. 14 illustrates images of polymer loading via centrifugation, in accordance with at least one example of this disclosure.

FIG. 15A illustrates bubble formation in a separation channel seen when initially heating a device, and FIG. 15B illustrates the separation channel after heating and spinning the device, where bubbles are removed, in accordance with at least one example of this disclosure.

FIG. 23A illustrates an exploded view of a gold electrode, in accordance with at least one example of this disclosure. FIG. 23B illustrates an exploded view of a gold electrode, in accordance with at least one example of this disclosure.

DETAILED DESCRIPTION

Example 1

Figure 1A:
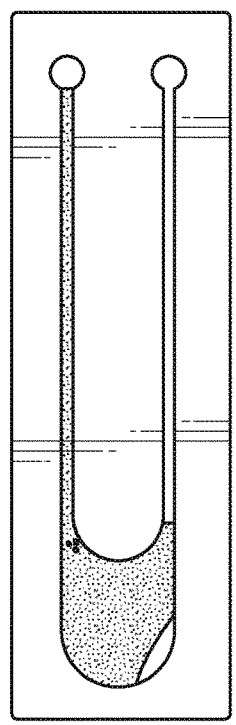
FIG. 1A illustrates a plan view of a chip, in accordance with at least one example of this disclosure.
Figure 1B:
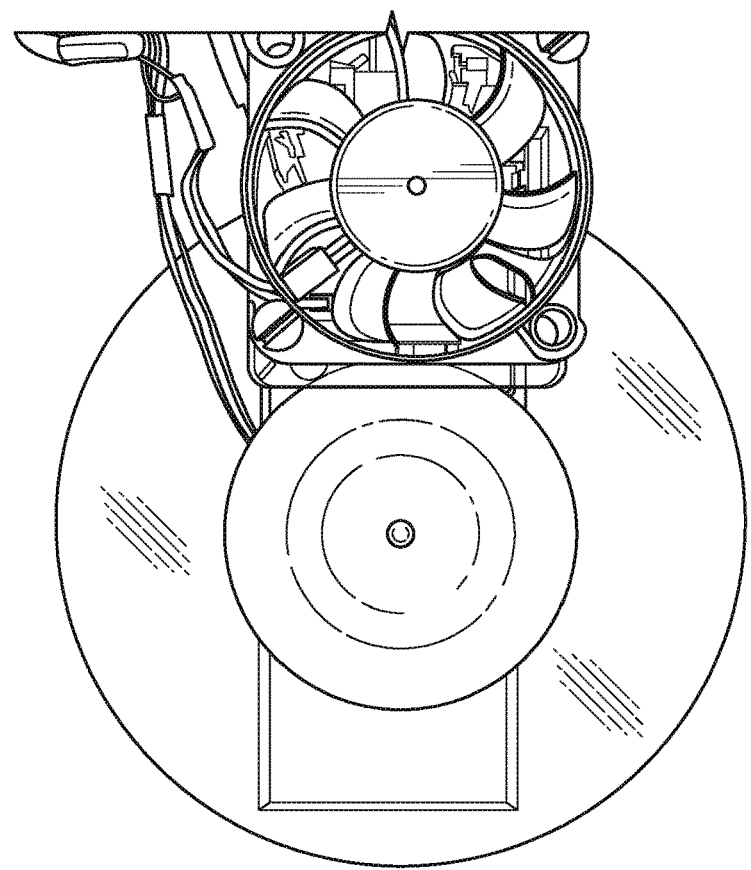
FIG. 1B illustrates a top view of the chip of FIG. 1A being spun by a thermocycling device, in accordance with at least one example of this disclosure.
Figure 1C:
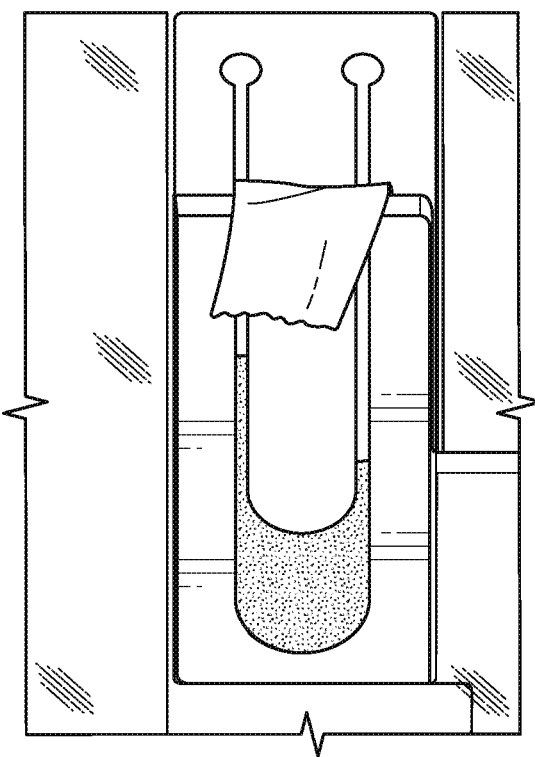
FIG. 1C illustrates a top view of the chip of FIGS. 1A and 1B, in accordance with at least one example of this disclosure.

FIG. 1A illustrates a plan view of a chip, in accordance with at least one example of this disclosure. FIG. 1B illustrates a top view of the chip of FIG. 1A being spun by a thermocycling device, in accordance with at least one example of this disclosure. FIG. 1C illustrates a top view of the chip of FIGS. 1A and 1B, in accordance with at least one example of this disclosure. FIGS. 1A-C. A) Bubble generation after heating a PCR chip to 96° C. for 60 seconds. B) Chip is spun at 500-4500 RPM for 1-60 seconds to degas after heating. C) Bubbles are eliminated for the remainder of amplification time.

One embodiment provides, among other things, a method and apparatus for multiplexed STR-based PCR on PeT chip. This embodiment addresses the problem of bubble formation as a result of heating small volumes in microfluidic devices or when loading fluids into microfluidic devices. The approaches to solving this are to either (a) avoid bubble formation by heating under pressure, or (b) degas the solution. The latter can be accomplished by spinning the chip from a few seconds to tens of minutes at a rotation rate between 500-4500 RPM (FIG. 1). The rotation frequency and the time allotted for degassing are dependent on the solution, and the dimensions of the architectural features involved.

Figure 2A:
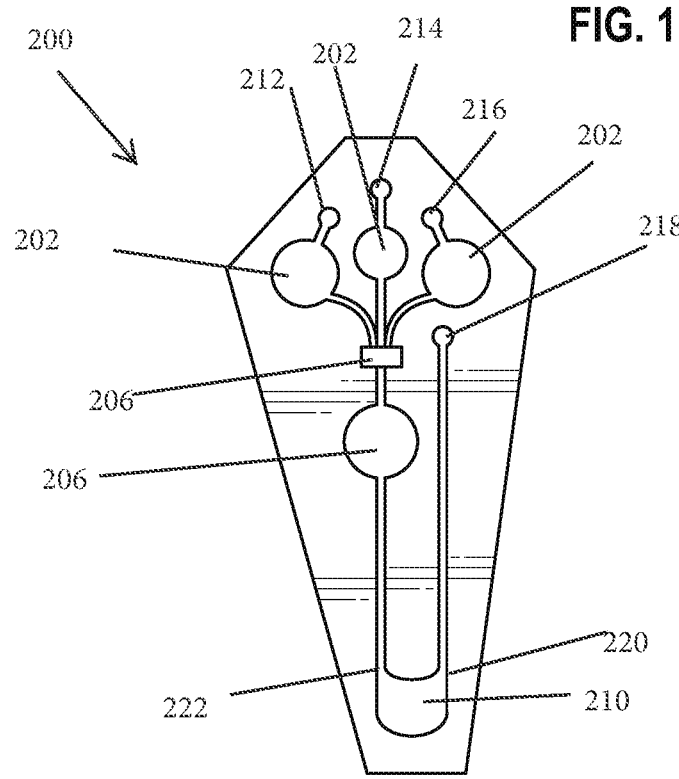
FIG. 2A illustrates a plan schematic view of a polymerase chain reaction chip, in accordance with at least one example of this disclosure.
Figure 2B:
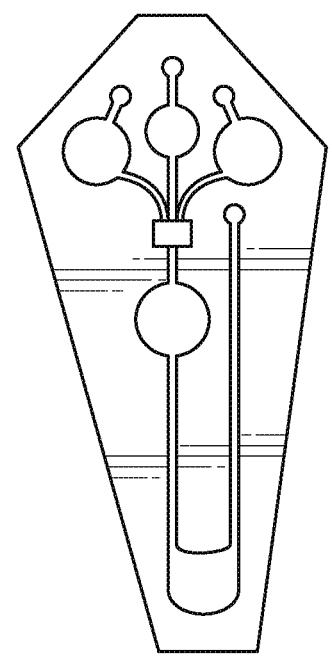
FIG. 2B illustrates a plan view of a polymerase chain reaction chip, in accordance with at least one example of this disclosure.

FIG. 2A illustrates a plan schematic view of a polymerase chain reaction chip, in accordance with at least one example of this disclosure. FIG. 2B illustrates a plan view of a polymerase chain reaction chip, in accordance with at least one example of this disclosure. FIGS. 2A-B. A) Schematic of PCR chip with separate reagent chambers and hydrophobic toner valve. B) PCR chip.

The reagents for PCR (master mix, primers) and sample (template) are maintained in separate chambers until PCR amplification is initiated. The reagents are housed in separate chambers, without the need for physical valves. This is accomplished using chambers with a volume capacity that is slightly larger than the reagent volume. In another embodiment, hydrophobic toner valves may be used (FIG. 2). Other types of valves, e.g., physical/mechanical valves that are opened (or closed) driven by some force (commonly pressure or vacuum) may also be used.

Chip 200 can include reagent chambers 202, toner vale 204, mixing chamber 206, outlet 208, reaction chamber 210, and vents 212, 214, 216, and 218.

Chip 200 can be configured for a reaction process such as a polymerase chain reaction. Vents 212 can be configured to vent gas from their respective chambers. Mixing chamber 206 can be configured to mix and degas a fluid. Reaction chamber 210 can include a first side 220 connected to vent 218 by a vent channel, and second side 222 connected to mixing chamber 206 by a chamber channel. Reagent chambers 202 can be connected to mixing chamber 206 by a plurality of reagent channels, and reagent chambers 202 can have a volume that is larger than a volume of reagents to control the flow of fluid into and out of reagent chambers 202.

Chip 200 can be comprised of polyester. In some examples valve 204, which can a hydrophobic toner valve in one example, can be connected to the reagent channels and mixing chamber 206. In some examples, chip 200 can have a shape of an irregular hexagonal prism.

In some examples, chip 200 can include a first thickness of the chip and a reaction chamber thickness, where the first thickness of the chip is larger than the polymerase chain reaction chamber thickness.

In some examples, chip 200 can include a reaction chamber volume, comprised of a reaction chamber height, length, and thickness. The reaction chamber dimension can be, for example, about 6 mm (l), about 5 mm (w) and about 100 μm (h). In this case, the reaction chamber can have a volume of about 3 cubic millimeters. Because the height or thickness is about 100 μm or 0.1 mm, the ratio of the height to the volume is about 3.3%. In other examples, the ratio can be 1-10%, or 2-5%.

Figure 3A:
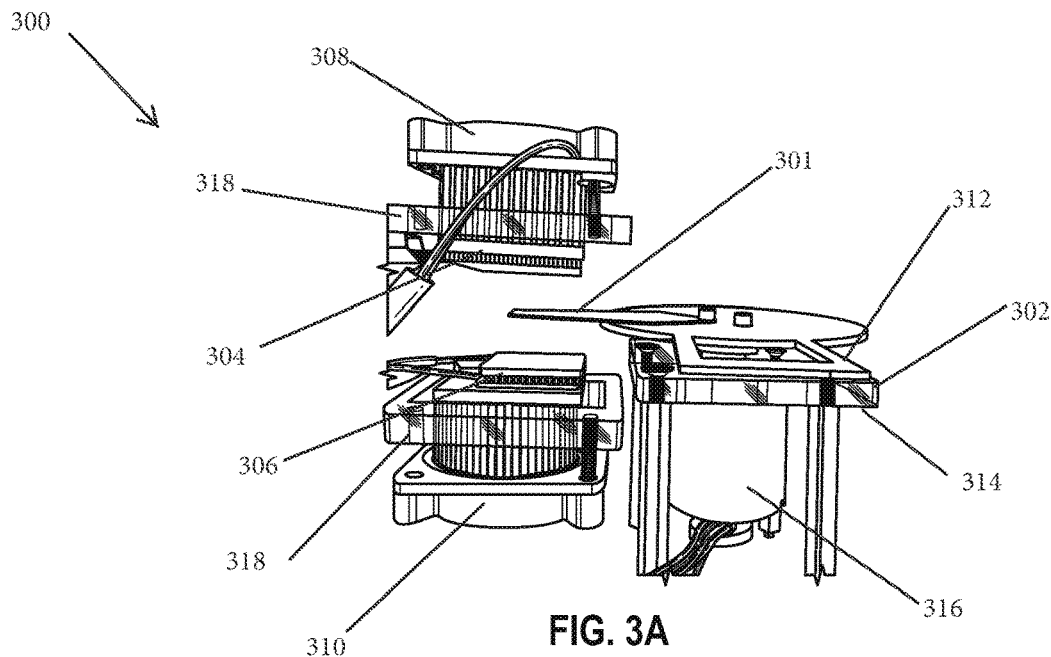
FIG. 3A illustrates a side view of a thermocycling device in an open position, in accordance with at least one example of this disclosure.
Figure 3B:
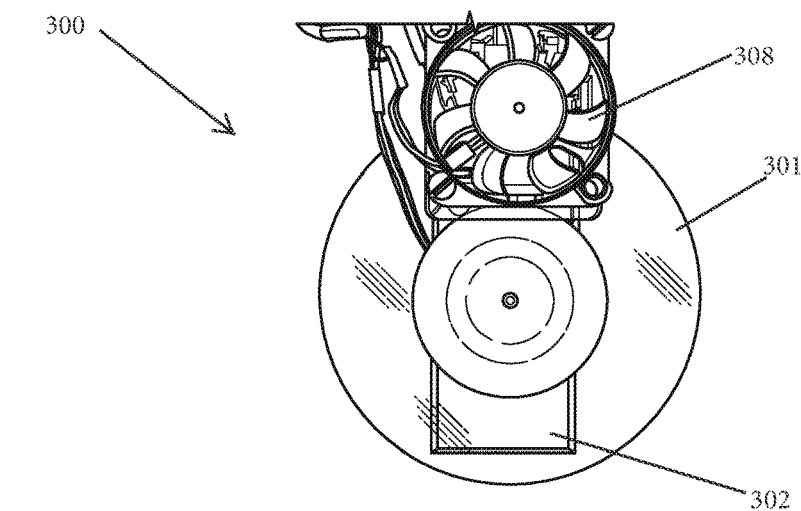
FIG. 3B illustrates a top view of a chip being spun by the thermocycling device of FIG. 3A, in accordance with at least one example of this disclosure.
Figure 3C:
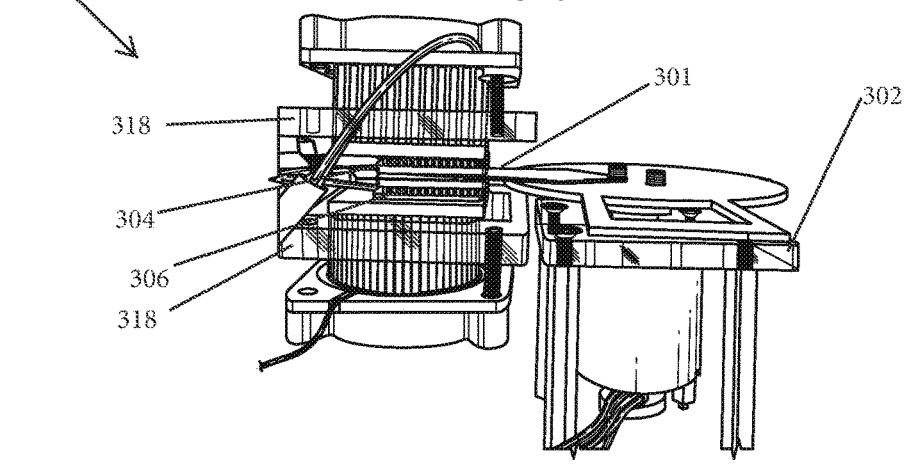
FIG. 3C illustrates a thermocycling device in closed position around a chip, in accordance with at least one example of this disclosure.

FIG. 3A illustrates a side view of a thermocycling device in an open position, in accordance with at least one example of this disclosure. FIG. 3B illustrates a top view of a chip being spun by the thermocycling device of FIG. 3A, in accordance with at least one example of this disclosure. FIG. 3C illustrates a thermocycling device in closed position around a chip, in accordance with at least one example of this disclosure. FIGS. 3A-C. A) DIPSS in open position allowing for chip to rotate between a dual heating system. B) DIPSS spinning to allow for fluidic movement (mixing, mobilization, degassing and the like). C) DIPSS in closed position allowing efficient thermocycling inside the PCR chip using clamp. FIGS. 3A-3C are discussed below concurrently.

Of the chip-based PCR systems that have been described, the vast majority of these involve the application of heat to one side of the chip/chamber—this can lead to inefficient heating and cooling, but can also be addressed by slowing the temperature cycling to allow equilibrium at each temperature. With the need to carry out rapid temperature cycling, a Dual Integrated Peltier Spinning System (DIPSS) was developed, which allows for heating from both sides of the chamber/chip simultaneously. A clamping system allows for contact between Peltier heaters and flat PCR chip (FIG. 3). Some of the components in this system are, but not limited thereto, two Peltier heaters and two fans (for thermocycling, heating and cooling, respectively).

Thermocycling device 300 can include rotating platform 302, thermoelectric heat pump 304, second thermoelectric heat pump 306, fan 308, and fan 310. Rotating platform 302 can include first side 312, second side 314, and motor 316. Thermocycling device 300 can also include clamp 318.

Rotating platform 302 can be configured to controllably spin chip 301, rotating platform 302 being drivable by motor 316. First side 312 can oppose second side 314.

Thermoelectric heat pump 304 can be disposed adjacent first side 312 and thermoelectric heat pump 306 can be disposed adjacent second side 314 to heat and/or cool chip 301. Fan 308 can be adjacent to thermoelectric heat pump 304 and can be configured to deliver a first flow of fluid to rotating platform 302 and chip 301. Fan 310 can be adjacent to thermoelectric heat pump 306 and can be configured to deliver a second flow of fluid to rotating platform 302 and chip 301.

Thermoelectric heat pumps 304 and 306 can be Peltier devices configured to heat (thermoelectric heating configuration) and cool (thermoelectric cooling configuration)

In some examples, thermocycling device 300 can include clamp 318 connected to thermoelectric heat pump 304 and thermoelectric heat pump 306. Clamp 318 can be configured to position thermoelectric heat pump 304 in contact with first side 312 and can be configured to position thermoelectric heat pump 306 in contact with second side 314.

Figure 4:
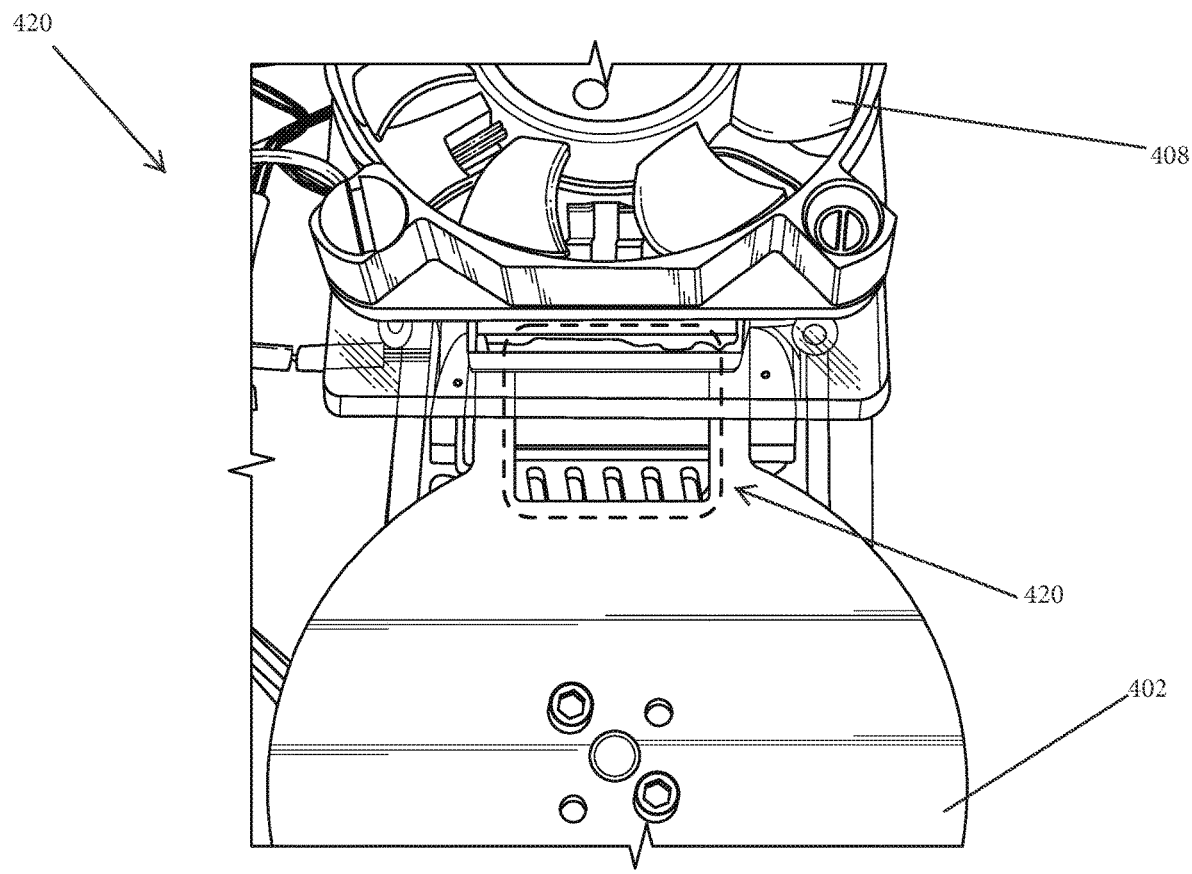
FIG. 4 illustrates a top view of the thermocycling device showing a sensor, in accordance with at least one example of this disclosure.

FIG. 4 illustrates a top view of the thermocycling device showing a sensor, in accordance with at least one example of this disclosure. FIG. 4. Optical switch allows for automated circular alignment of PCR chip.

Chip-based PCR systems often require manual alignment/adjustment. A system was developed with an optical alignment switch to allow for automated alignment of the PCR chip. This device allows for alignment of a circular PCR chip with 10° accuracy (FIG. 4).

Thermocycling device 400 can include optical alignment switch 420 connected to rotating platform 402. Optical alignment switch 420 can be configured to align a chip on rotating platform 402.

Thermoelectric device 500 can include thermoelectric heat pump 506, which can include exposed metallic surface 522. Exposed metallic surface 522 can comprise a thin layer of aluminum, gold, and the like. Exposed metallic surface 522 can face rotating platform 502 and can have a small thermal mass relative to a chip and thermoelectric heat pump 522 to enable faster heating and cooling. In some examples, thermoelectric heat pump 504 can also include exposed metallic surface 522.

Figure 5:
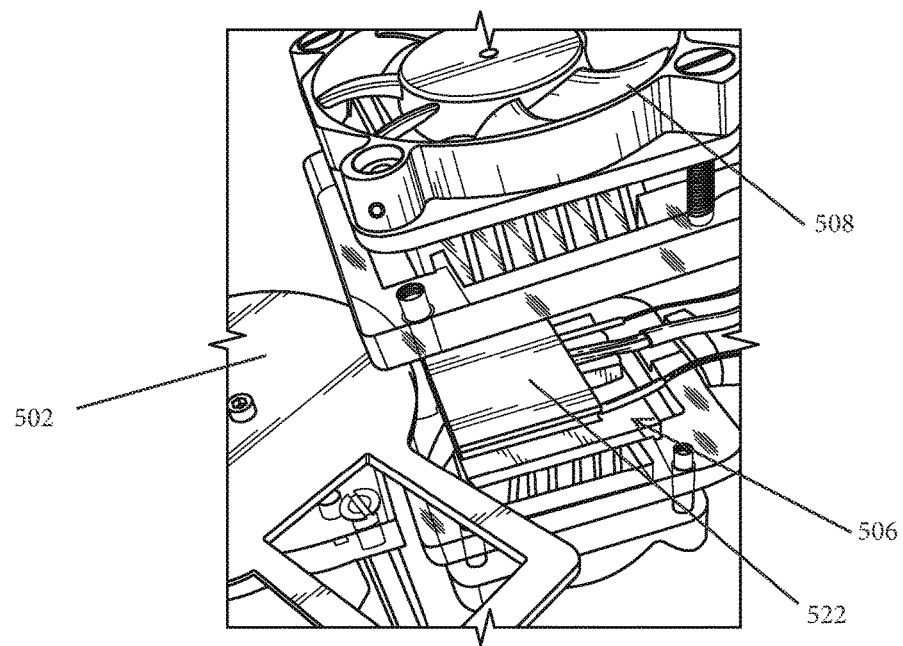
FIG. 5 illustrates a perspective view of the thermocycling device showing a metallic surface of one thermoelectric heat pump of the thermocycling device, in accordance with at least one example of this disclosure.
Figure 6:
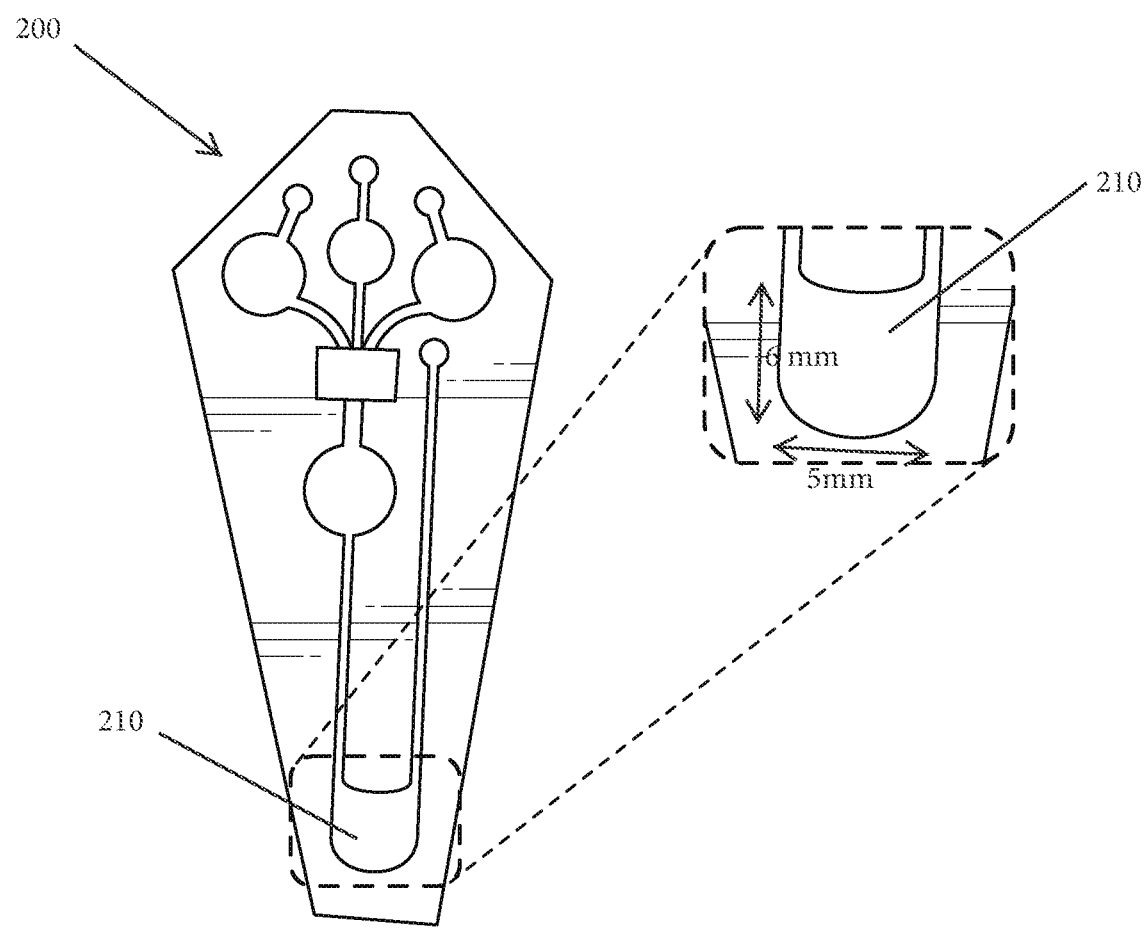
FIG. 6 illustrates a chip configured for a polymerase chain reaction process with a focused view showing an aspect ratio of a polymerase chain reaction chamber of the hip, in accordance with at least one example of this disclosure.

FIG. 5 illustrates a perspective view of the thermocycling device showing a metallic surface of one thermoelectric heat pump of the thermocycling device, in accordance with at least one example of this disclosure. FIG. 5. Dual Peltiers are enhanced using a metal surface for reduced thermal gradients and low thermal mass for rapid heating/cooling. Peltiers tend to have temperature gradients that could affect accurate thermocycling of small volume liquids in microareas of the Peltier surface. To reduce temperature gradients and maintain low thermal mass for rapid heating/cooling, a thin layer of aluminum was applied over the exposed surface of the Peltiers. The clamping system allows for effective contact between the Peltier heaters and flat PCR chip (FIG. 5). FIG. 6 illustrates a chip configured for a polymerase chain reaction process with a focused view showing an aspect ratio of a polymerase chain reaction chamber of the hip, in accordance with at least one example of this disclosure. FIG. 6. PeT is employed for thin height in PCR chamber, allowing for increased volume exposed to dual heating system. Aspect ratio is about 6 mm (l), 5 mm (w) and 100 μm (h)).

Chips with deeper chambers can be less efficient to heat using a dual heating system. To address this, the aspect ratio of the PCR chamber was modified to increase the efficiency of heating and cooling using the thin nature of the Pe layer (about 100 μm) to achieve a PCR chamber with a maximum exposed surface for contact with the heating elements. The length and width of the chamber was also increased to obtain the highest Peltier-exposed surface area relative to the volume in the chamber. In one embodiment, the aspect ratio (l, w, h) is approximately 6 mm, 5 mm, and 100 μm (FIG. 6).

Figure 7A:
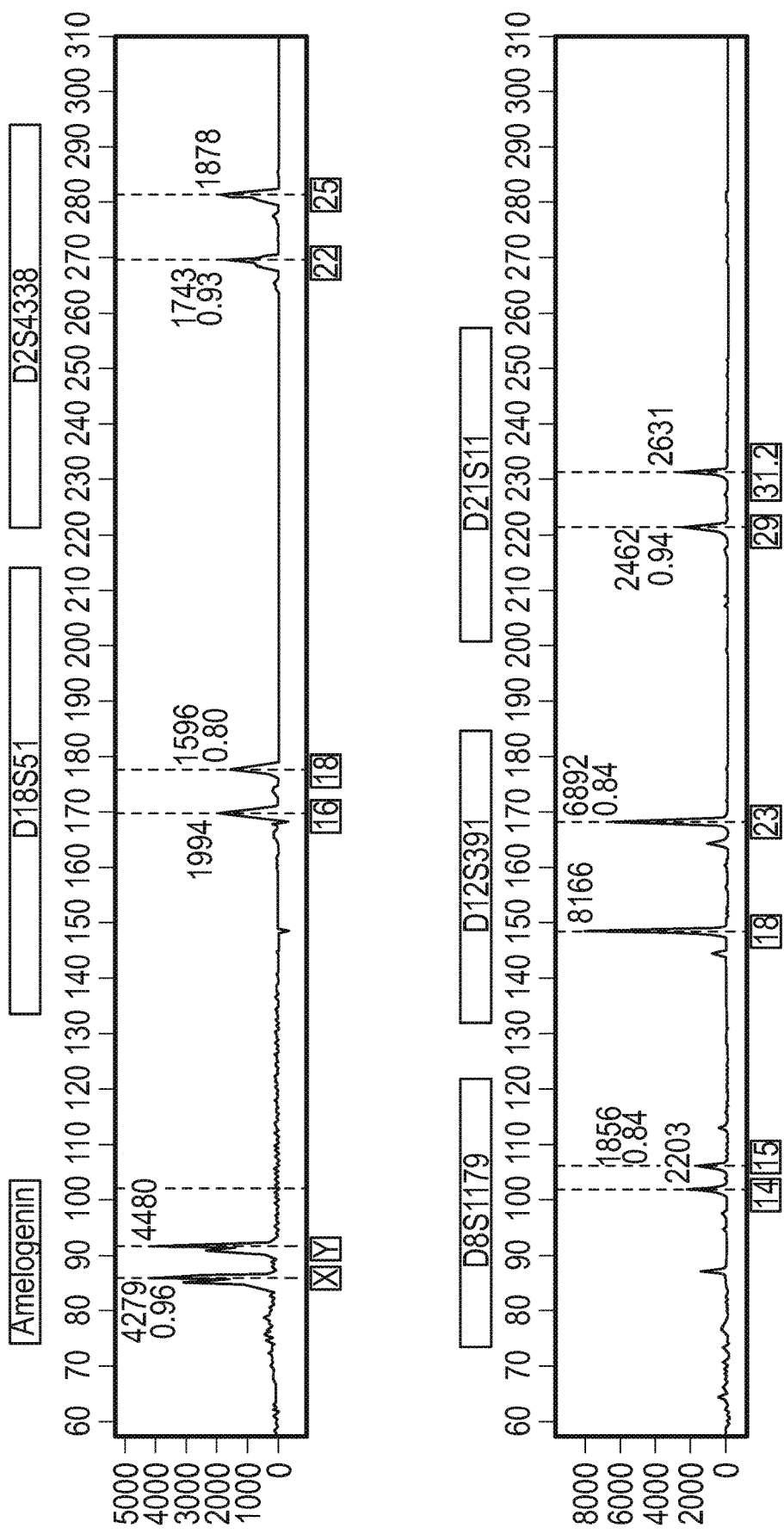
FIG. 7A illustrates a non-chip profile using 6-plex STR kit.
Figure 7B:
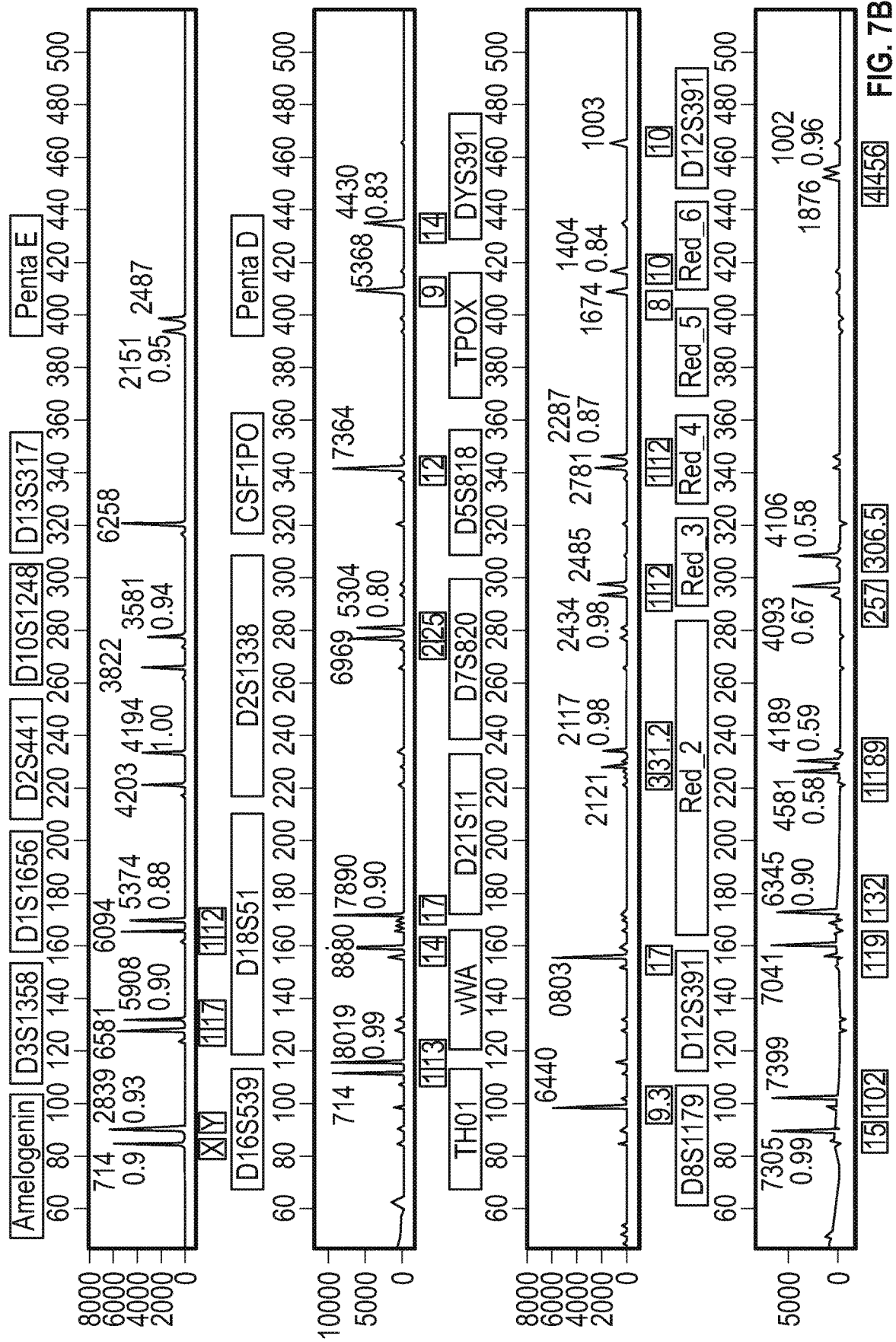
FIG. 7B illustrates-chip profile using the Fusion kit.
Figure 7C:
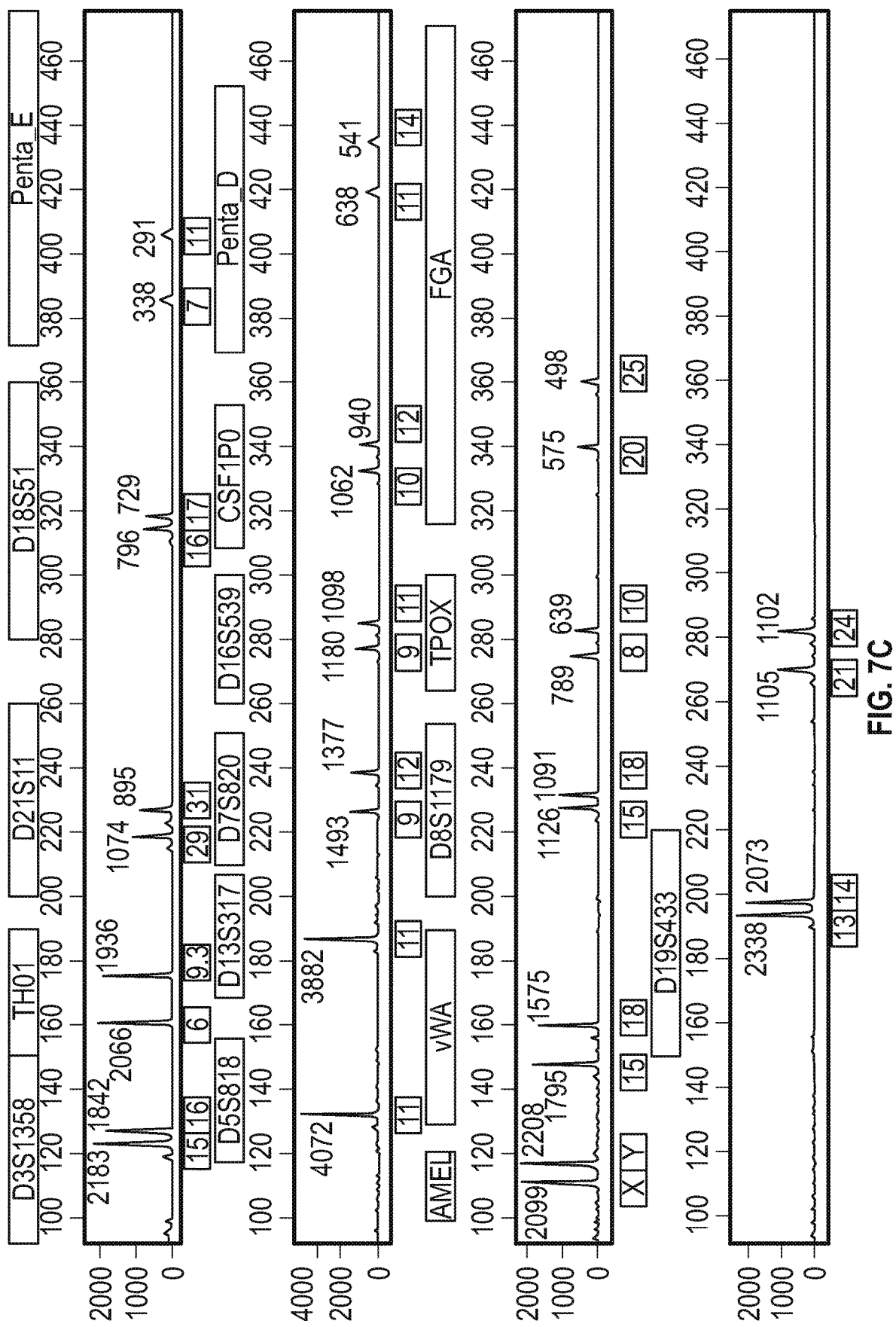
FIG. 7C illustrates an on-chip profile using a modified Powerplex 18D kit.
Figure 7D:
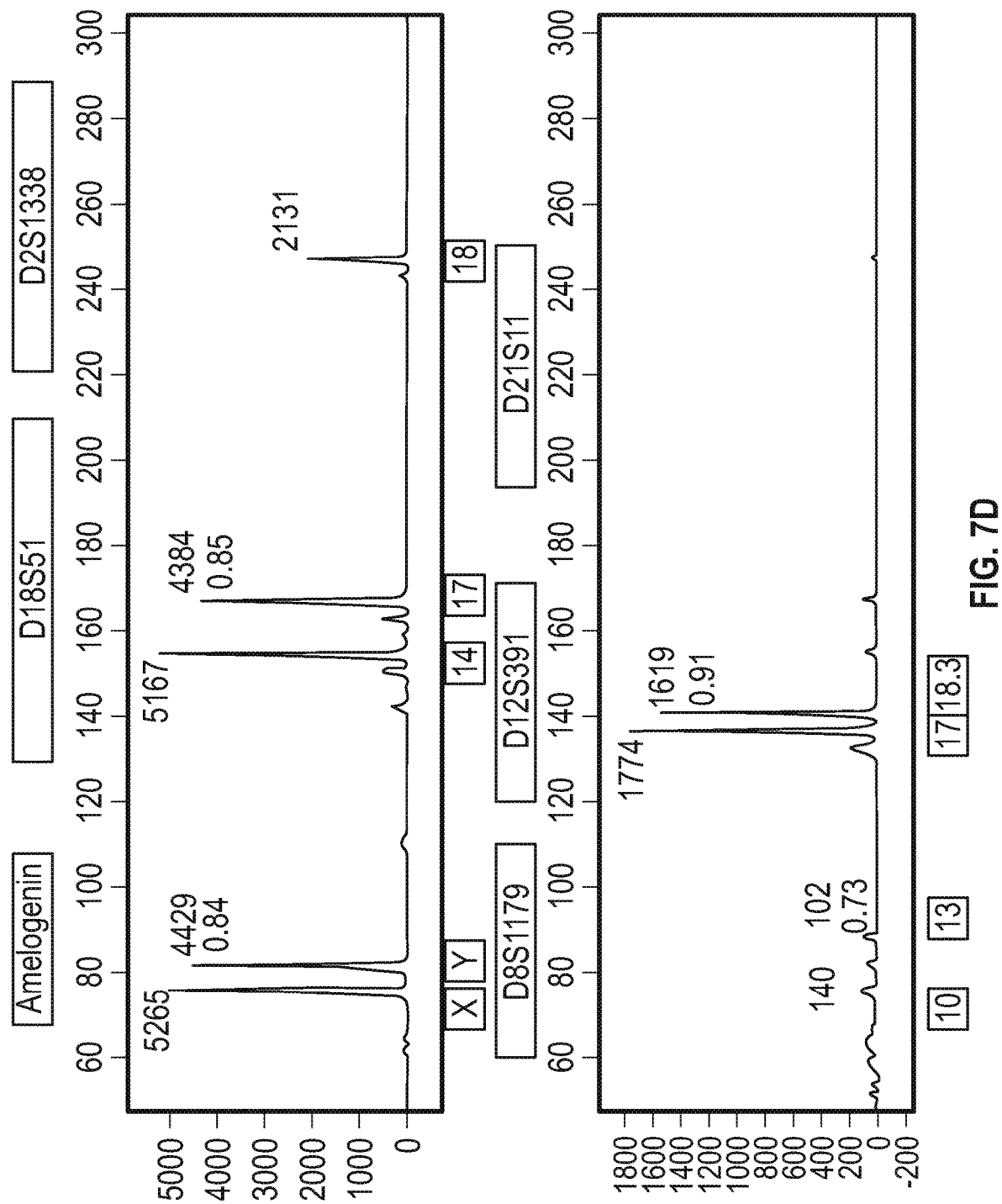
FIG. 7D illustrates an on-chip profile using Splex primers and rapid conditions in a 21 minute PCR, in accordance with at least one example of this disclosure.

FIG. 7A illustrates an on-chip profile using 6-plex STR kit, FIG. 7B illustrates-chip profile using the Fusion kit, FIG. 7C illustrates an on-chip profile using a modified Powerplex 18D kit, FIG. 7D illustrates an on-chip profile using Splex primers and rapid conditions in a 21 minute PCR, in accordance with at least one example of this disclosure. FIGS. 7A-D. A) On-chip profile using 6-plex STR kit. B) On-chip profile using the Fusion kit. C) On-chip profile using the modified Powerplex 18D kit. D) On-chip profile using Splex primers and rapid conditions in a 21 minute PCR.

The use of the DIPSS system was demonstrated with several STR-based PCR kits, including a custom-designed 6-plex, Powerplex Fusion, and a modified Powerplex 18D kit. Full on-chip profiles may be obtained in 21 minutes using a 5-plex primer combination (FIG. 7).

Example 2

Figure 8A:
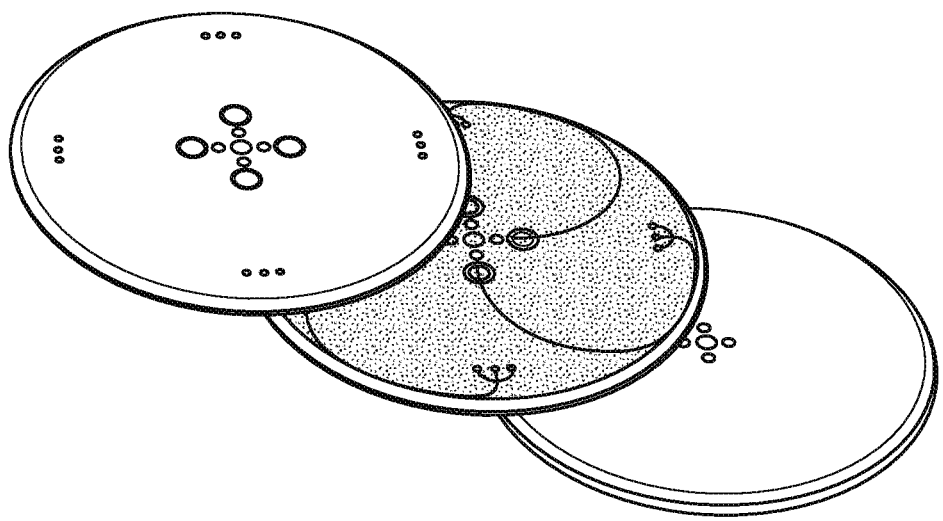
FIG. 8A illustrates an isometric view of a separation device, in accordance with at least one example of this disclosure.
Figure 8B:
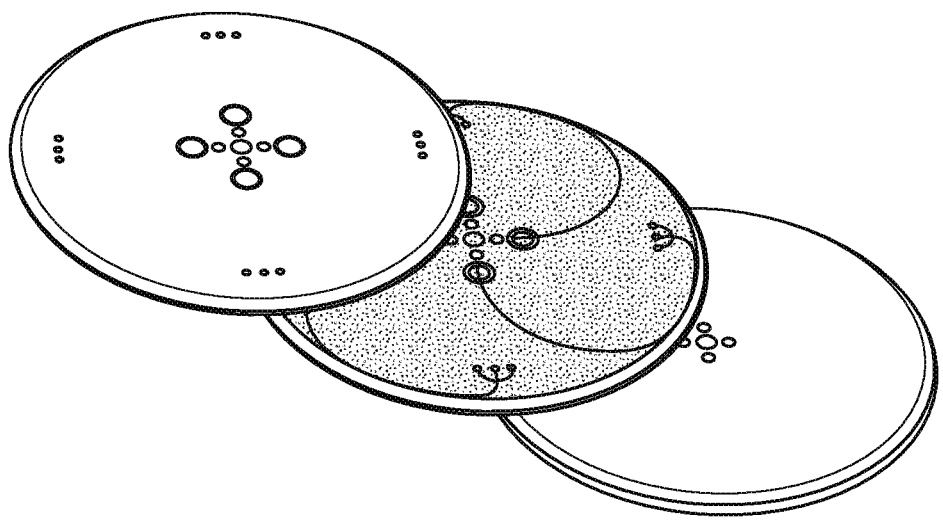
FIG. 8B illustrates an isometric view of another separation device, in accordance with at least one example of this disclosure.

FIG. 8A illustrates an isometric view of a separation device, in accordance with at least one example of this disclosure. FIG. 8B illustrates an isometric view of another separation device, in accordance with at least one example of this disclosure. FIGS. 8A-B. A) Schematic of a three-layer separation device made of COC-Pe-COC B) Schematic of a three-layer separation device made of COC-PSA-COC.

In one embodiment, methods and devices for DNA Separation on a Rotationally Driven Microdevice are provided, e.g., a centrifugal microfluidic device using a combination of inexpensive materials including, in one embodiment, cyclic olefin copolymer (COC), polyester (Pe), and pressure-sensitive adhesive (PSA), for the separation of DNA (FIG. 8). Devices are fabricated using a print-cut-laminate (PCL) technique, where the toner-coated middle layer limits the detection of background autofluorescence around the channel.

Figure 9:
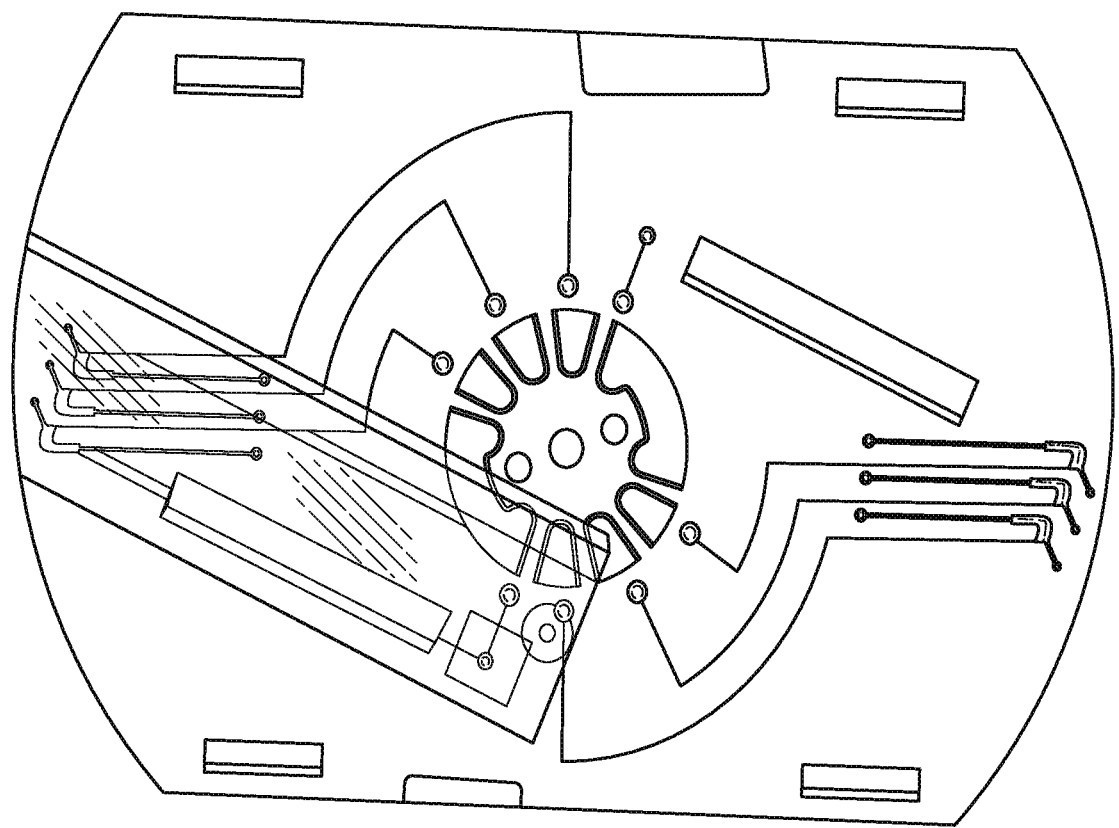
FIG. 9 illustrates a plan view of an injection molded separation device mounted to a chip, in accordance with at least one example of this disclosure.

FIG. 9 illustrates a plan view of an injection molded separation device mounted to a chip, in accordance with at least one example of this disclosure. FIG. 9. Image of an injection molded separation device mounted to an integrated fluidic and reagent storage architecture. In addition, injection molded separation devices are mounted to PCL-fabricated fluidic layers to create an integrated device that reduces overall injection molding/fabrication challenges (FIG. 9). The separation chip is bonded to the fluidic and reagent storage architecture through the use of adhesive.

Figure 10A:
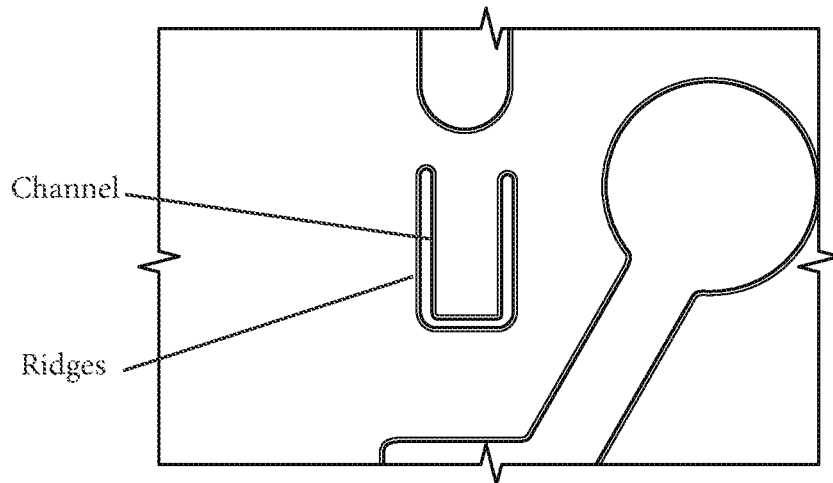
FIG. 10A illustrates a focused view of a chip showing ridges in channels caused by an ablation process, in accordance with at least one example of this disclosure.
Figure 10B:
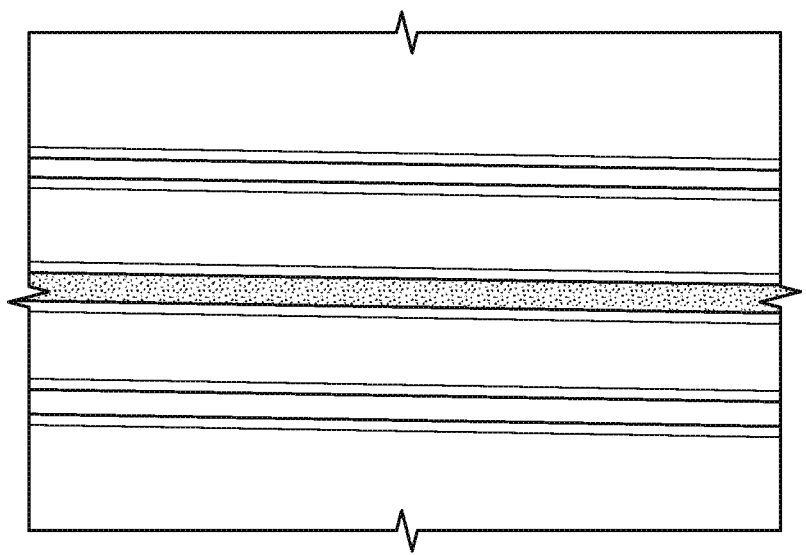
FIG. 10B illustrates a focused view of the chip after a pre-lamination procedure and final bonding, in accordance with at least one example of this disclosure.

FIG. 10A illustrates a focused view of a chip showing ridges in channels caused by an ablation process, in accordance with at least one example of this disclosure. FIG. 10B illustrates a focused view of the chip after a pre-lamination procedure and final bonding, in accordance with at least one example of this disclosure. FIGS. 10A-B. A) Image of ridges caused by melting of toner and Pe during the ablation process. B) An image of a device after the pre-lamination procedure and final bonding. During the PCL fabrication, ridges of melted toner and Pe adhesive form from the ablation of the material during the cutting process. These ridges may have negative impacts when bonding, causing leaking and eventually leading to delamination (FIG. 10A). To fix this issue, a 'pre-lamination' step is employed prior to final bonding, in which the cut toner layers are placed between two non-bonding materials and introduced into the bonding laminator. This step smooths all of the formed ridges and promotes more complete bonding of the final devices (FIG. 10B).

Figure 11:
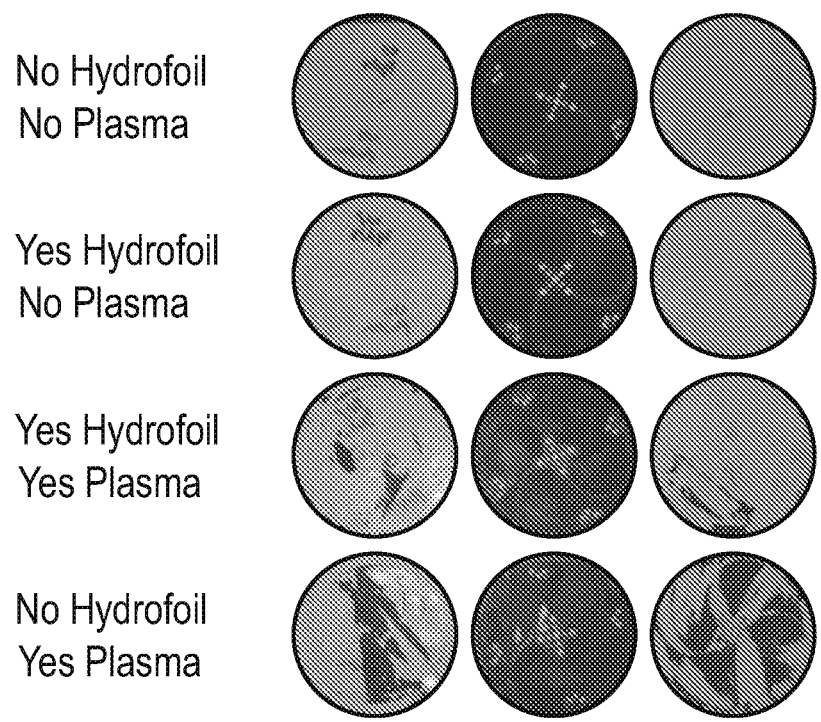
FIG. 11 illustrates several examples of chip layer bonding before and after plasma oxidation, in accordance with at least one example of this disclosure.

FIG. 11 illustrates several examples of chip layer bonding before and after plasma oxidation, in accordance with at least one example of this disclosure. FIG. 11. After 7 minutes of plasma oxidation, the COC layers are shown to bond more efficiently to the COC layers, as indicated by the transfer of toner. When introducing COC as top and bottom layers of the devices, it was noted that the toner did not provide for adhesion for strong bonding between layers, and delamination was observed. To overcome this issue, each surface was plasma oxidized for 7 minutes prior to the final lamination step. The plasma oxidation improves the interaction of the toner with the COC layers and delamination was no longer observed (FIG. 11).

Figure 12:
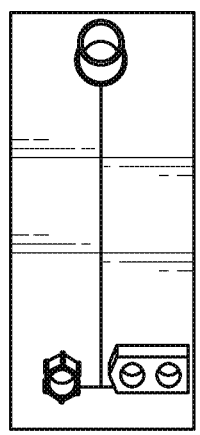
FIG. 12 illustrates a top view of a separation device, in accordance with at least one example of this disclosure.

FIG. 12 illustrates a top view of a separation device, in accordance with at least one example of this disclosure. FIG. 12. A three-layer separation device made of COC-PSA-COC using a PCL fabrication method.

Previously, channel dimensions in separation devices using similar materials were limited to the number of toner layers printed on the substrate. As mentioned above, the PCL method was used, which involves cutting through the middle layer and using the thickness of the layer to determine the channel dimensions (FIG. 12).

Figure 13:
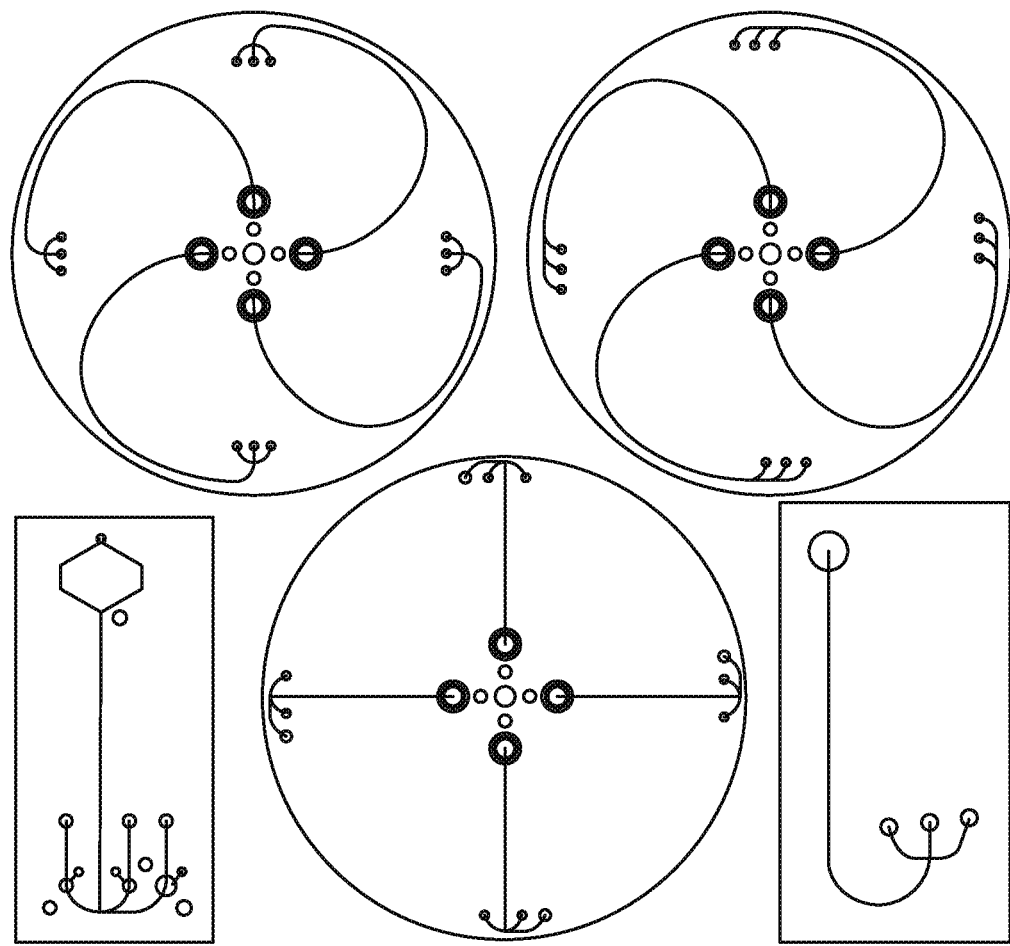
FIG. 13 illustrates a plan schematic view series of several separation channel and reservoir designs on a chip, in accordance with at least one example of this disclosure.

FIG. 13 illustrates a plan schematic view series of several separation channel and reservoir designs on a chip, in accordance with at least one example of this disclosure. FIG. 13. A series of exemplary separation channel and reservoir designs used to facilitate polymer loading via centrifugation.

The viscosity of the sieving polymer makes loading long, narrow channels difficult and time consuming. Polymer reservoirs and separation channel shapes were designed to facilitate the ease of polymer loading. These designs follow the direction of the rotation and take advantage of both the radial force and the drag force (FIG. 13).

FIG. 14 illustrates images of polymer loading via centrifugation, in accordance with at least one example of this disclosure. FIG. 14. Images of polymer loading via centrifugation.

FIG. 14 illustrates the loading of a 4% sieving polymer via centrifugation in these various designs.

FIG. 15A illustrates bubble formation in a separation channel seen when initially heating a device, and FIG. 15B illustrates the separation channel after heating and spinning the device, where bubbles are removed, in accordance with at least one example of this disclosure. FIGS. 15A-B. A) Bubble formation in the separation channel seen when initially heating the device. B) After heating and spinning the device, bubbles are removed.

The toner used on the middle layer of the device is porous in nature and results in bubble formation in the channels when the device is heated (FIG. 15A). Thus, bubbles are removed, which prevents further creation of bubbles, by heating and spinning the device pre- and post-loading of polymer, prior to separation (FIG. 15B)

Figure 16A:
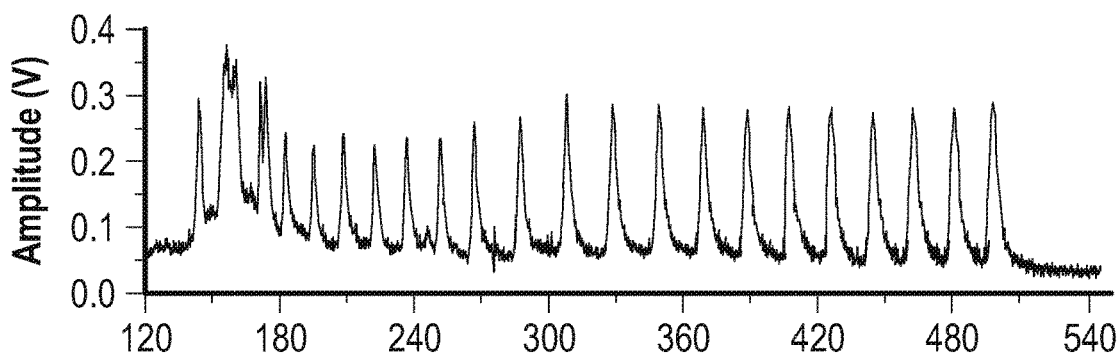
FIGS. 16A and 16B illustrate separation of internal lane standard (ILS) on both COC-PeT-COC (A) and COC-PSA-COC (B), in accordance with at least one example of this disclosure.
Figure 16B:
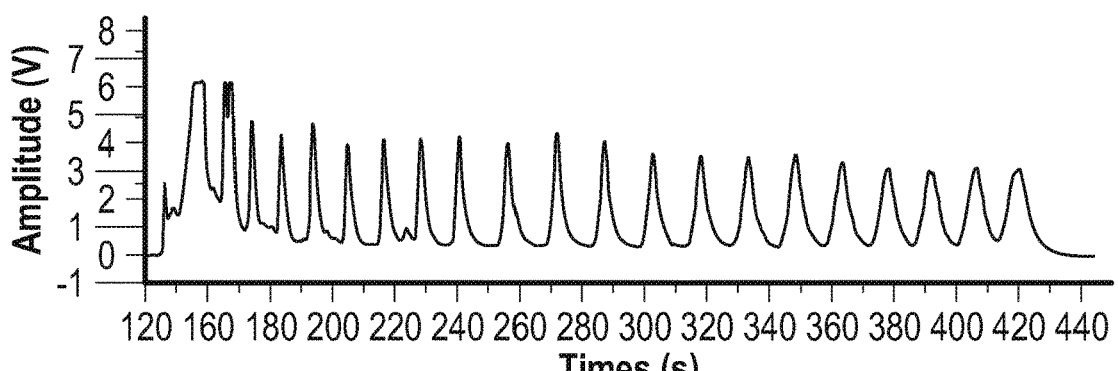
Figure 16C:
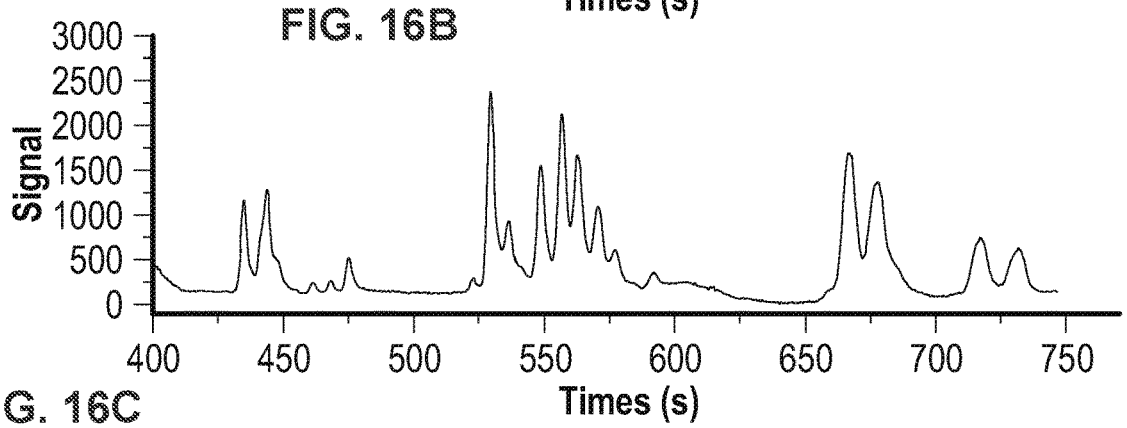
FIGS. 16C and 16D illustrate initial separation of amplified DNA fragments on a COC-PeT-COC device (C) compared to a conventional separation (D), in accordance with at least one example of this disclosure.
Figure 16D:
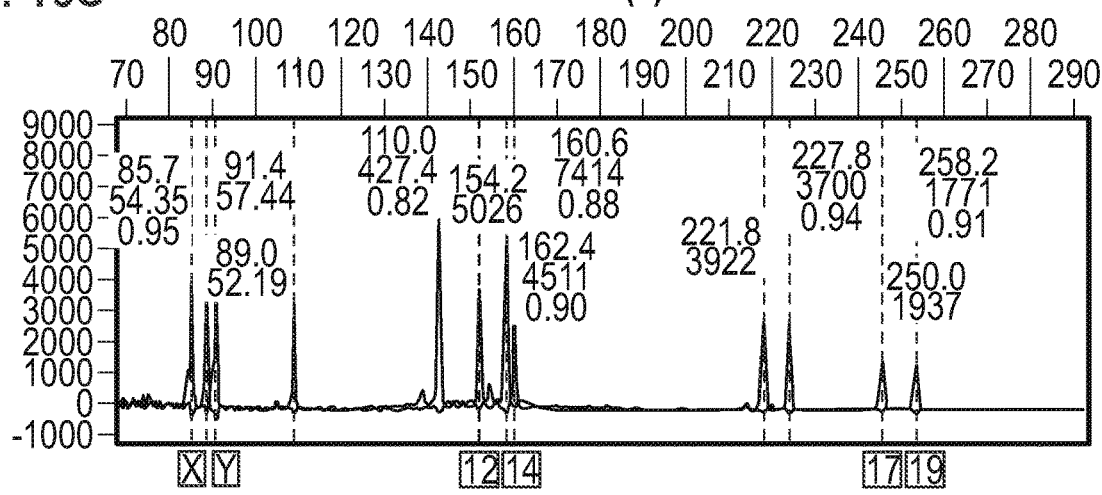

FIGS. 16A and 16B illustrate separation of internal lane standard (ILS) on both COC-PeT-COC (A) and COC-PSA-COC (B), in accordance with at least one example of this disclosure. FIGS. 16C and 16D illustrate initial separation of amplified DNA fragments on a COC-PeT-COC device (C) compared to a conventional separation (D), in accordance with at least one example of this disclosure. Using the methods above, the separation of DNA fragments was achieved at a resolution of >0.11 (see FIG. 16).

A centrifugal microfluidic device configured for separation of nucleic acids can include a top layer, a middle layer, and a bottom layer. The top layer can be comprised of cyclic olefin copolymer. The top layer can include a first top layer side and a second top layer side opposing the first top layer side. The middle layer can include a first middle layer side that can be configured to mate to the second top layer side, and a second middle layer side opposing the first middle layer side. The bottom layer can be comprised of cyclic olefin copolymer. The bottom layer can include a first bottom layer side that can be configured to mate to the second middle layer side, and a second bottom layer side opposing the first bottom layer side.

In some examples, the middle layer can be comprised of a pressure sensitive adhesive. In some examples the middle layer is comprised of toner-printed polyethylene terephthalate.

In some examples, the first middle layer side and the second middle layer side can each be plasma oxidized. In some examples, the first middle layer side and the second middle layer side can each be plasma oxidized for about five to about ten minutes.

In some examples, the centrifugal microfluidic device can include an injection molded separation device that can be mounted to one of the top layer, the middle layer, and the bottom layer. In some examples, the injection molded separation device can be secured using an adhesive.

In some examples, the middle layer can include a sample reservoir that can be disposed near a center of the middle layer and a plurality of polymer reservoirs that can be disposed near a periphery of the middle layer. The middle layer can further include a separation channel that can extend radially outward from the sample reservoir, and can include plurality of polymer reservoir channels, each connectable to the separation channel and can extend radially beyond the plurality of polymer reservoirs and can each turn inward to connect to one of the plurality of polymer reservoirs.

In some examples, the separation channel can extend circumferentially and radially from the sample reservoir to the periphery of the middle layer and then can extend substantially circumferentially before connecting to the plurality of polymer reservoir channels.

In some examples, the separation channel can extend radially inward before connecting to the plurality of polymer reservoir channels.

In some examples, the middle layer can include a plurality of sample reservoirs including the sample reservoir, where each of the plurality of sample reservoirs can be disposed near a center of the middle layer. In some examples, the middle layer can include a plurality of separation channels including the separation channel, where each of the plurality of separation channels can extend radially outward from the sample reservoir.

A method of creating a centrifugal microfluidic device configured for separation of nucleic acids can include forming a top layer, forming a middle layer, and forming a bottom layer. Channels and chambers can be ablated into the middle layer. The middle layer can be surrounded with non-bonding layers. Ridges adjacent the channels and the chambers can be re-profiled after ablating the channels and chambers by introducing the middle layer surrounded by the non-bonding layers into a bonding laminator. The top layer and the bottom layer can be bonded to the middle layer.

In some examples, top layer and the bottom layer can be comprised of cyclic olefin copolymer. In some examples, the middle layer can be comprised of a toner-printed polyethylene terephthalate.

In some examples, the method of creating a centrifugal microfluidic device can include plasma oxidizing a first side of the middle layer prior to boding one of the top layer and the bottom layer to the middle layer. In some examples, the method of creating a centrifugal microfluidic device can include plasma oxidizing a second side of the middle layer prior to boding one of the top layer and the bottom layer to the middle layer.

In some examples, the ablating process can cut entirely through the middle layer to create the channels and chambers.

Example 3

Figure 17A:
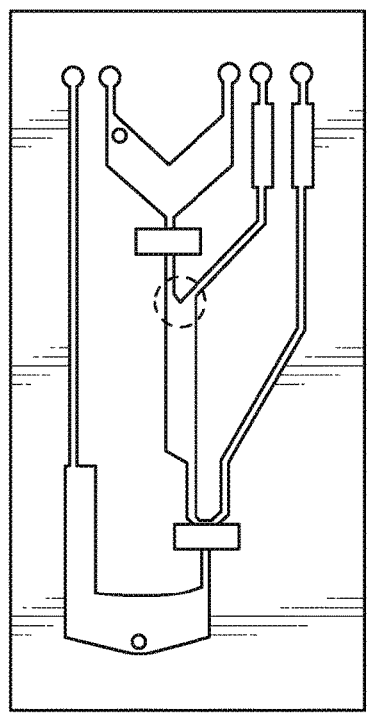
FIG. 17A illustrates a plan schematic view of a chip, in accordance with at least one example of this disclosure.
Figure 17B:
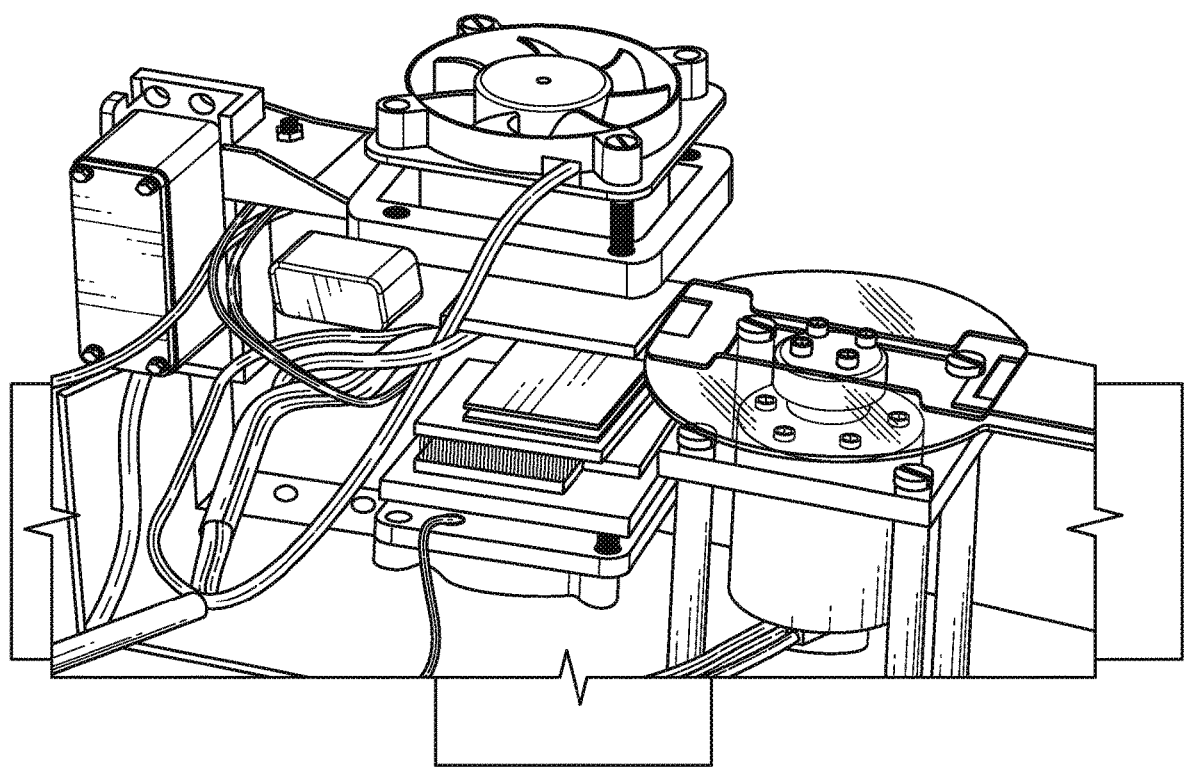
FIG. 17B illustrates a rotational system utilized for fluidic movement, in accordance with at least one example of this disclosure.
Figure 17C:
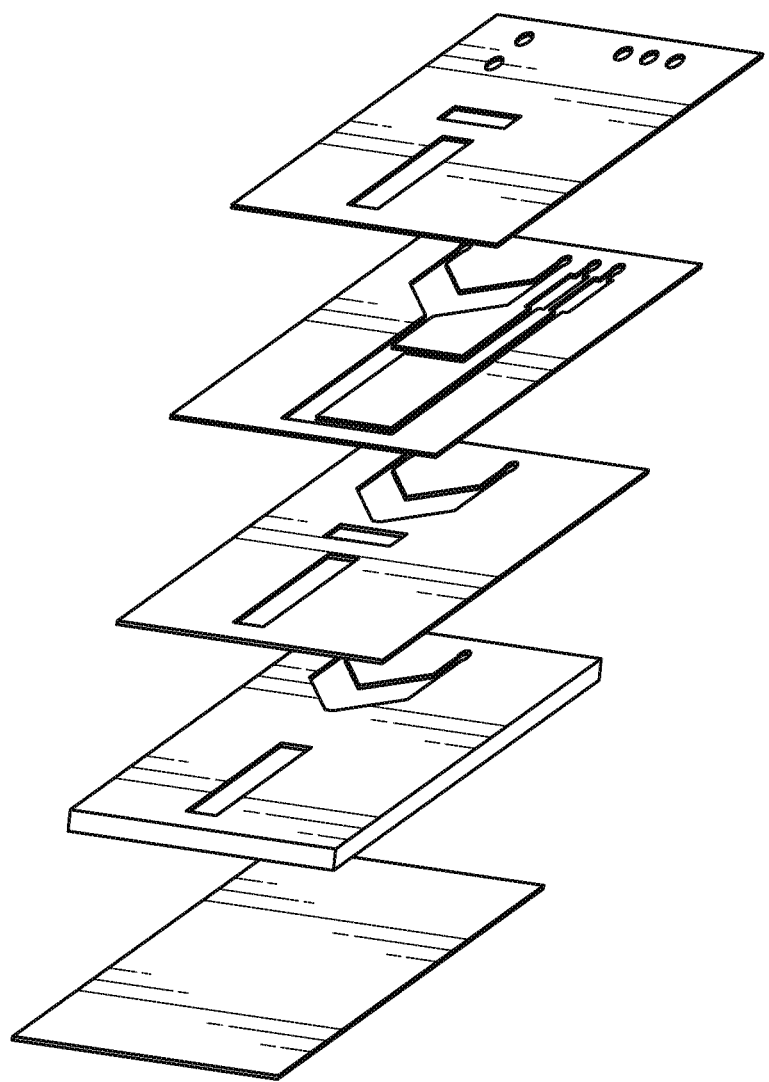
FIG. 17C illustrates an isometric view and a top view of a chip design, in accordance with at least one example of this disclosure.

FIG. 17A illustrates a plan schematic view of a chip, in accordance with at least one example of this disclosure. FIG. 17B illustrates a rotational system utilized for fluidic movement, in accordance with at least one example of this disclosure. FIG. 17C illustrates an isometric view and a top view of a chip design, in accordance with at least one example of this disclosure. FIGS. 17A-C. A) Exemplary device design. B) An exemplary rotational system utilized for fluidic movement. C) A design without laser-actuated valves or the recovery chamber.

One embodiment provides a device and method for DNA liberation with EA1. An aspect of an embodiment provides, among other things, a centrifugal microfluidic device and related method (FIG. 17) for DNA liberation with EA1 enzyme (from MicroGEM), consisting of a reagent storage chamber, a liberation chamber, and a product recovery chamber that are connected with laser-actuated valves.

FIGS. 18A-D: A) Red dye stays in the liberation chamber when heated at 75° C.; B) Sideview of the red dye in the liberation chamber; C) Microscopic image of an opened valve; and, D) Red dye in the recovery chamber, in accordance with at least one example of this disclosure.

A user only needs to load a buccal swab into the liberation chamber and seal the chamber. The valve of the storage chamber is opened, after which the device is spun at a certain speed to release the enzyme pre-loaded in the storage chamber. The device is then aligned to a heater for the enzymatic DNA liberation (heating at 75° C. for 2 min and 95° C. for 0.5 min). After the heating process, the valve of the recovery chamber is opened, and the device is spun at a certain speed to separate the product from the swab (FIG. 18).

Figure 19A:
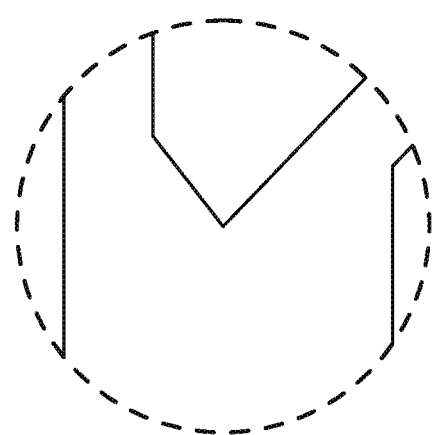
FIG. 19A illustrates a focused view of a ventilation of a chip, in accordance with at least one example of this disclosure.
Figure 19B:
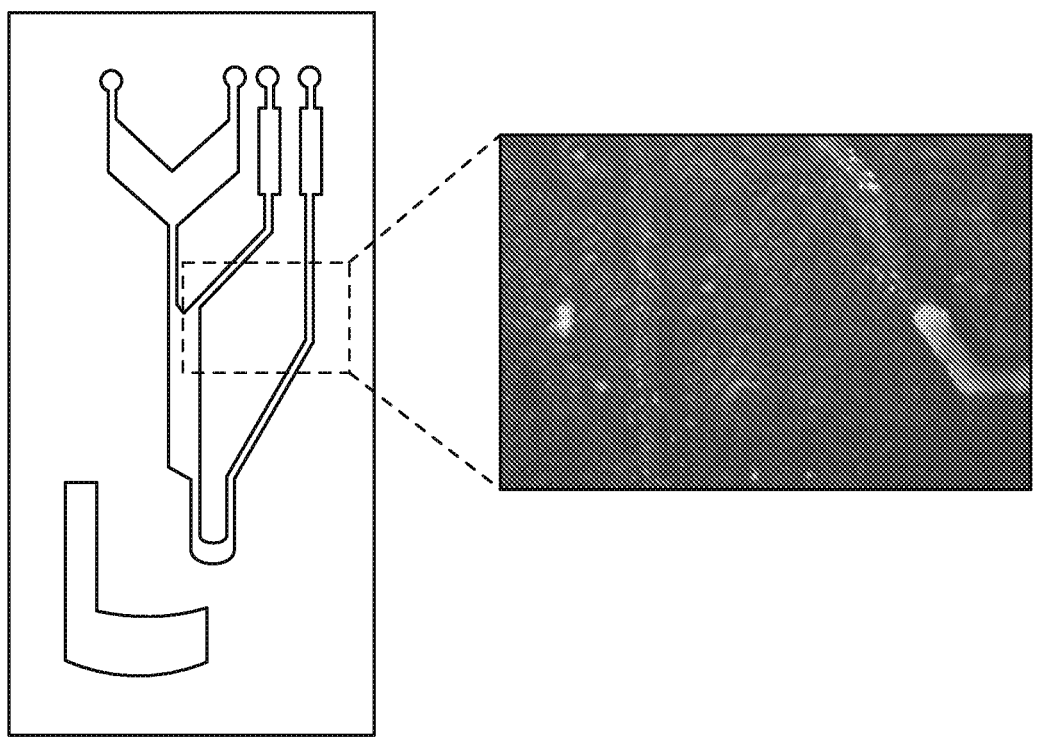
FIG. 19B illustrates a chip without the V shape design, where liquid fills the vent line other than the liberation chamber due to capillary force.
Figure 20A:
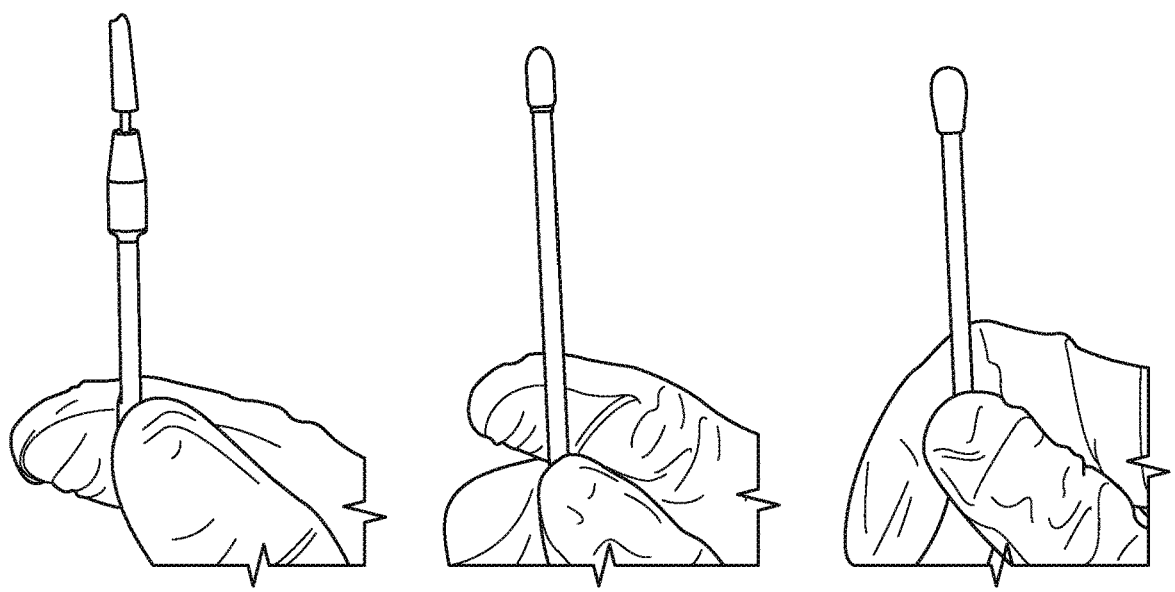
FIGS. 20A-20B: images of three different swab types for DNA collection and liberation: A) the images above display the three brushes; and, B) the graph compare each swab (n=4) and the concentration of DNA that was obtained from each, in accordance with at least one example of this disclosure.
Figure 20B:
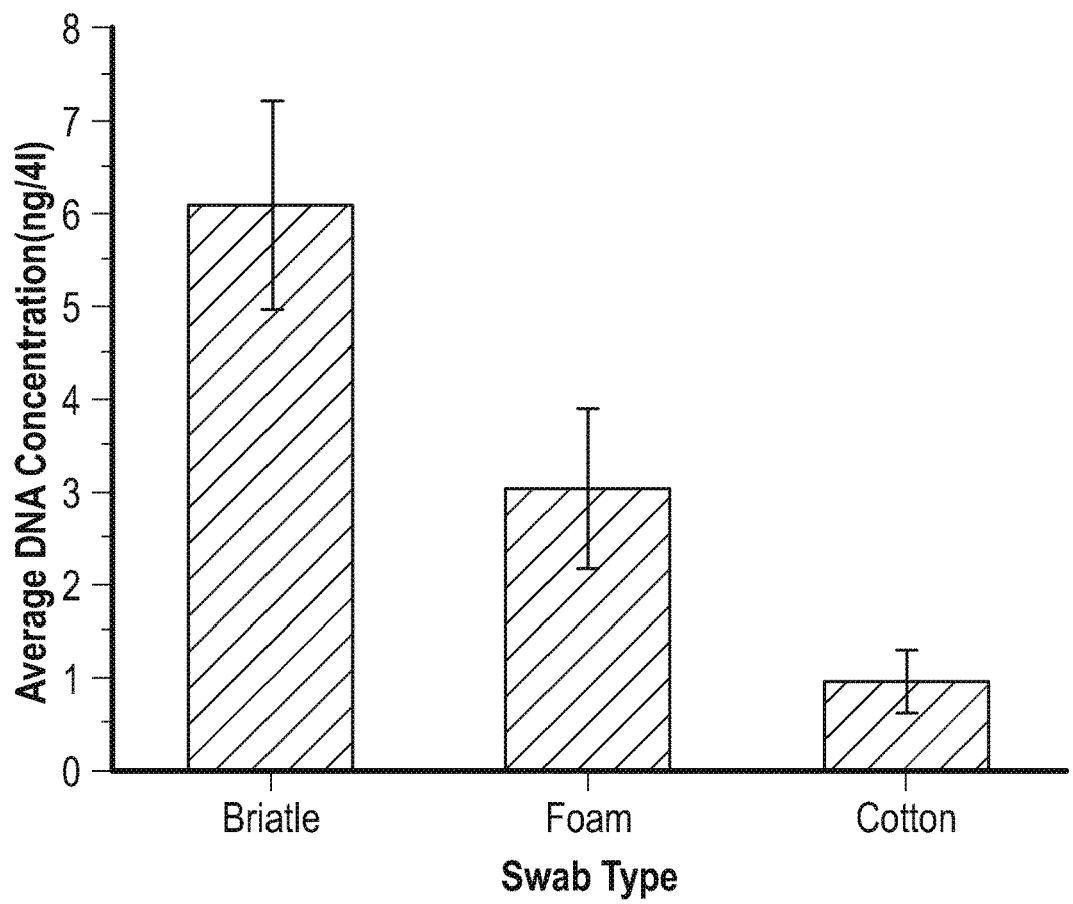

FIG. 19A illustrates a focused view of a ventilation of a chip, in accordance with at least one example of this disclosure. Figure B illustrates a chip without the V shape design, where liquid fills the vent line other than the liberation chamber due to capillary force. FIGS. 19A-B. A) Exemplary design for proper ventilation. B) Without the V shape design, liquid fills the vent line other than the liberation chamber due to capillary force. FIGS. 20A-B: images of three different swab types for DNA collection and liberation: A) the images above display the three brushes; and, B) the graph compare each swab (n=4) and the concentration of DNA that was obtained from each, in accordance with at least one example of this disclosure.

Figure 18A:
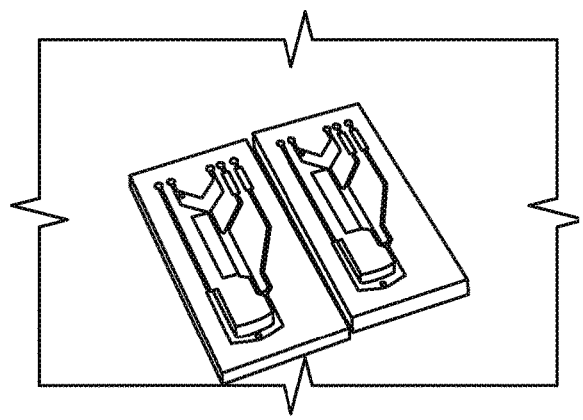
FIG. 18A) Red dye stays in the liberation chamber when heated at 75° C.
Figure 18B:
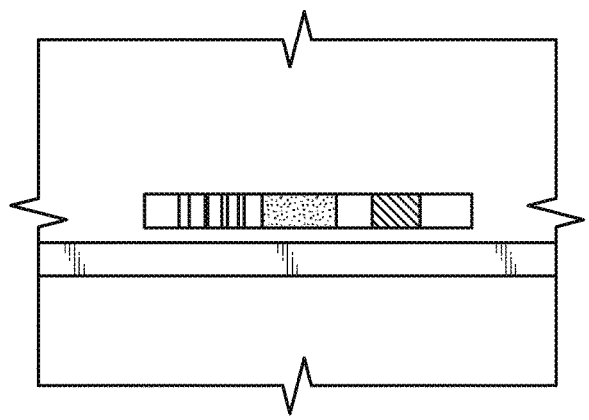
FIG. 18B) Sideview of the red dye in the liberation chamber.
Figure 18C:
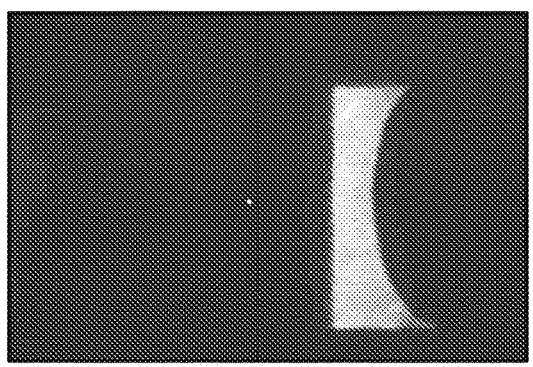
FIG. 18C) Microscopic image of an opened valve; and, FIG. 18D) Red dye in the recovery chamber, in accordance with at least one example of this disclosure.
Figure 18D:
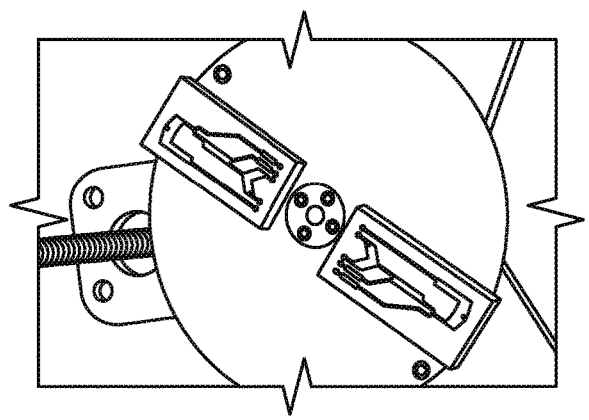

One of the aspects of the device design, among other things, lies in the liberation chamber. (1) Two vent lines are connected to the liberation chamber to prevent air from being trapped in the liquid, which allows the liquid to stay in the chamber when heated (FIG. 18A). (2) The channel wall highlighted in the dotted circle is design to be in a "V" shape (FIG. 19A), which facilitates ventilation and prevents liquid from filling the vent line (FIG. 18A).

DNA is collected, for example, using a cotton swab, foam swab, or bristle brush, and the liberation yield for each was assessed (FIG. 19). To collect DNA, each participant rinsed their mouth with water and then gently rotated a swab around their cheek for 30 seconds. The bristle brush resulted in a high DNA yield.

A series of samples were tested with the device, and the liberation yields are listed in the tables below. Overall, the device produced 5.85 ng/μL of DNA on average with 100% success rate.

TABLE 1

DNA liberation of 4 samples from 3 participants with an overall average DNA concentration of 6.20 ± 1.53 ng/μL.

| Sample | DNA Conc. 1 (ng/μL) | DNA Conc. 2 (ng/μL) | DNA Conc. 3 (ng/μL) | DNA Conc. 4 (ng/μL) | Average (ng/μL) | Std. Dev. |
|---|---|---|---|---|---|---|
| Participant 1 | 3.48 | 3.02 | 9.52 | 3.01 | 4.76 | 3.18 |
| Participant 2 | 7.59 | 5.85 | 5.97 | 4.81 | 6.06 | 1.15 |
| Participant 3 | 10.27 | 10.98 | 6.29 | 3.65 | 7.80 | 3.45 |

TABLE 2

Overall average DNA concentration from 20 samples collected from 10 different participants using the Polyester-PMMA microdevice and ZyGEM solution.

| Number of Samples | Overall Average DNA Conc. (ng/μL) | Std. Dev. |
|---|---|---|
| 20 | 5.85 | 2.41 |

Figure 21:
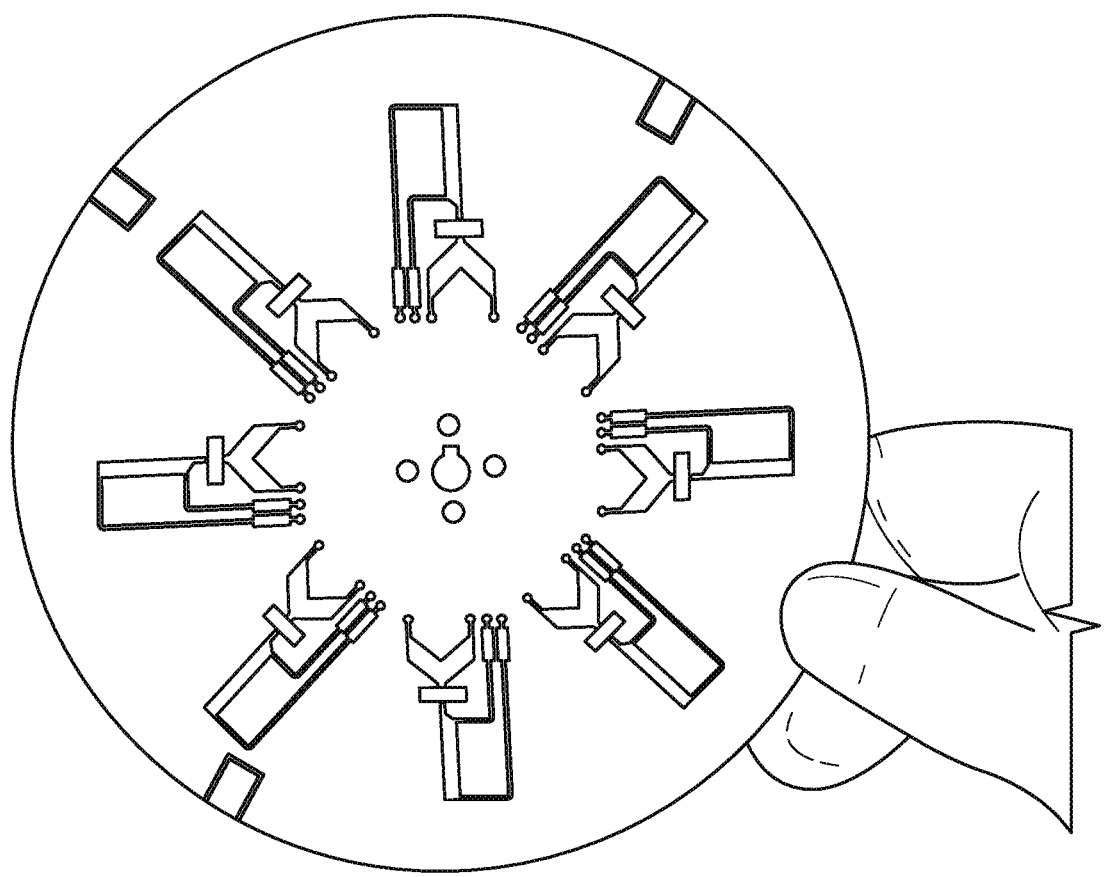
FIG. 21 illustrates a multiplexed disc containing an array of liberation chambers, in accordance with at least one example of this disclosure.

FIG. 21 illustrates a multiplexed disc containing an array of liberation chambers, in accordance with at least one example of this disclosure.

Figure 22:
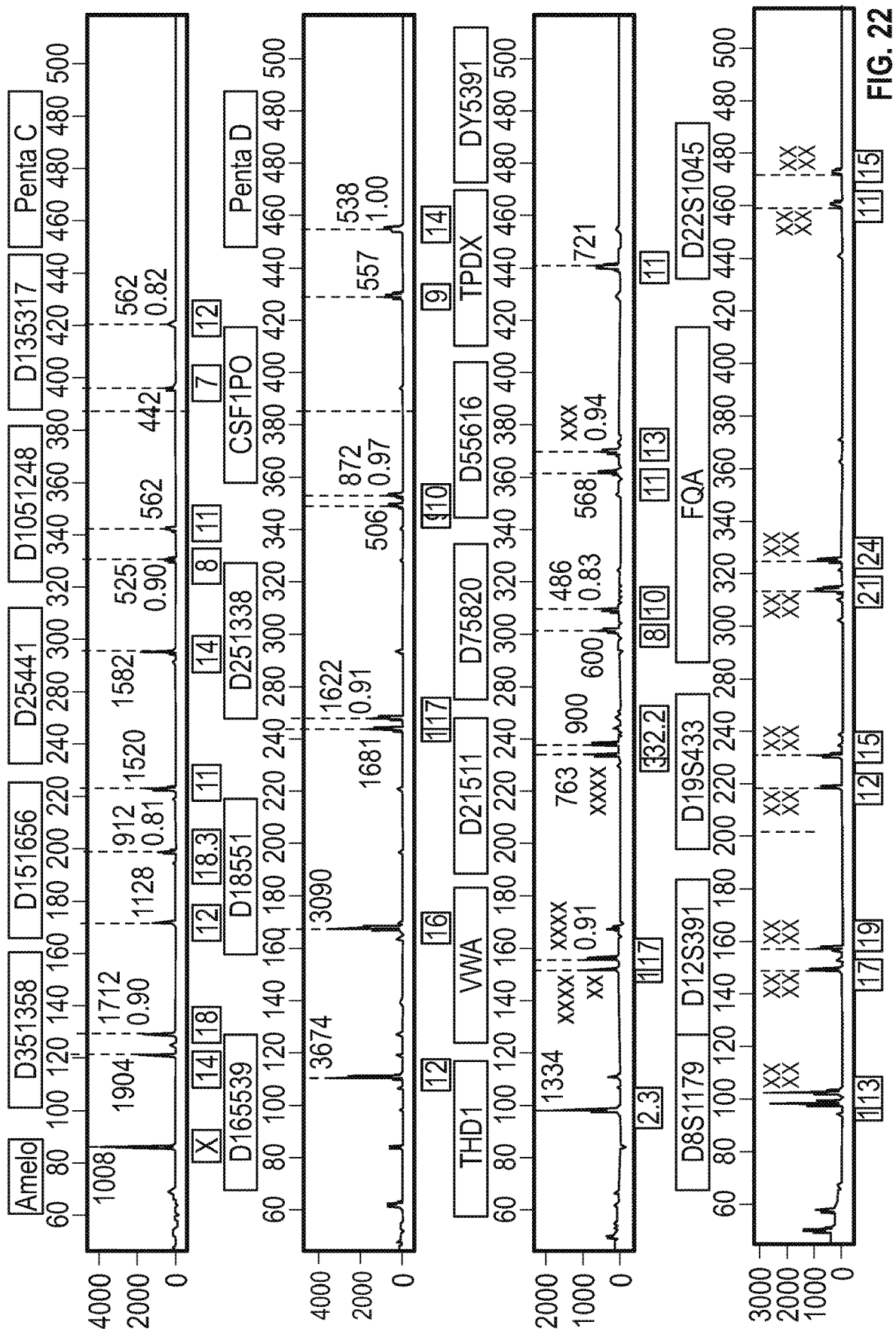
FIG. 22. A STR profile obtained after PCR with a DNA sample liberated using the device shown in FIG. 21, in accordance with at least one example of this disclosure.

FIG. 22. A STR profile obtained after PCR with a DNA sample liberated using the device shown in FIG. 21, in accordance with at least one example of this disclosure.

FIG. 21 shows a multiplexed device that can accommodate 8 samples. Simultaneous liberation was performed within 3 min, yielding 3.24±2.62 ng DNA per sample. A strong full 24-plex was obtained with all the peaks above a 200-RFU threshold (FIG. 22).

A chip configured to liberate nucleic acid through a centrifugal process can include a main vent, a recovery vent, a liberation vent, a plurality of storage vents, a first and second valve, a reagent chamber, a liberation chamber, and a recovery chamber. Each vent can be configured to vent gas. The reagent chamber can be connected to the plurality of storage vents and connected to the first valve. The liberation chamber can include a first liberation chamber end connected to the first valve and connected to a liberation vent, and can include a second liberation chamber end connected to the second valve, where the second valve can be connected to the recovery vent. The recovery chamber can include a first recovery side that can be connected to the main vent and a second recovery side that can be connected to the second valve.

In some examples, the chip can be formed of a plurality of polyester layers. In some examples, the first valve and the second valve are one of laser-actuated valves and hydrophobic valves. In some examples, the liberation chamber is configured receive a sample and configured to mix a reagent with the sample.

In some examples, the chip can include a liberation vent channel that can be connected to the first liberation chamber end and can be connected to the liberation vent and can form a vent connection between the liberation vent channel and the first liberation chamber end. The chip can also include a liberation first valve channel that can be connected to the first valve and can be connected to the first liberation chamber end and can form a valve connection between the liberation first valve channel and the first liberation chamber end.

In some examples, the vent connection and the valve connection can connect to the liberation chamber adjacently.

In some examples, the chip can include a transition between the vent connection and the valve connection that can comprise a V shape In some examples the plurality of chips can be circumferentially distributed around the chip such that a centrifugal process can be performed on each chip simultaneously.

A method of liberating a product using a chip can include pre-loading a reagent into a storage chamber of the chip and opening a liberation chamber of the chip. A swab can be loaded into the liberation chamber and the liberation chamber can be sealed. A storage valve of the chip can be opened and the chip can be spun to release the reagent from the storage chamber into the liberation chamber. The chip can be aligned to a heater and can be heated liberate the product. The recovery valve can be opened and the chip can be spun to separate product from the swab.

In some examples, the swab can be one of a bristle swab, a foam swab, and a cotton swab. In some examples the chip can be heated to about 75 degrees Celsius for about 2 minutes and about 95 degrees Celsius for about 30 seconds.

Example 4

DNA Analysis (Extraction, PCR, and Separation) Via Centrifugal Means

Separation

The typical thickness of a polyethylene terephthalate sheet used in the "laser print, cut and laminate" method is around 100 micrometers, and in a five-layer device, the maximum depth of a microfluidic architecture is around 300 micrometers (three sheets plus adhesives). In order to create a 100-microliter chamber, one would need the footprint to be 330 mm$^2$ (roughly 18 mm×18 mm) which may be (1) too big for a microfluidic device and (2) difficult to laminate without sagging. Moreover, it is sometimes desired to create a chamber deeper than 300 micrometers, e.g., to accommodate a buccal swab for DNA liberation/extraction. For those reasons, PMMA was added as an additional layer. Besides minimizing footprint and accommodating large objects, PMMA balances the weight of the whole device.

Heat sensitive adhesive (HSA) was added to the disc fabrication process to facilitate an easier alignment process, as the complete device is comprised of many layers. The use of pressure sensitive adhesive only allows a user one chance to successfully align a piece of the device before it is permanently adhered. Introducing HSA allows a user to correctly confirm the appropriate position of the layers without a "one shot chance", because the adhesive properties of the HSA are only activated upon heat. As heat and pressure are the only requirements to active the adhesive, the current lamination process already implemented in the fabrication process (one pass through a pouch thermal laminator at 200° C. with a roller speed of 8 mm/s) is suitable to complete the bonding of the device without alteration to the method or additional/different heating equipment. In addition, the HSA properties allow it to be used in the laser cutting protocol, with optimized power and speed parameters (15% power, 10% speed) found to be capable of vector ablation on the 50 Watt $CO_2$ VersaLaser system, which, ultimately together, create the microfluidic architecture.

Electrodes

Figure 23C:
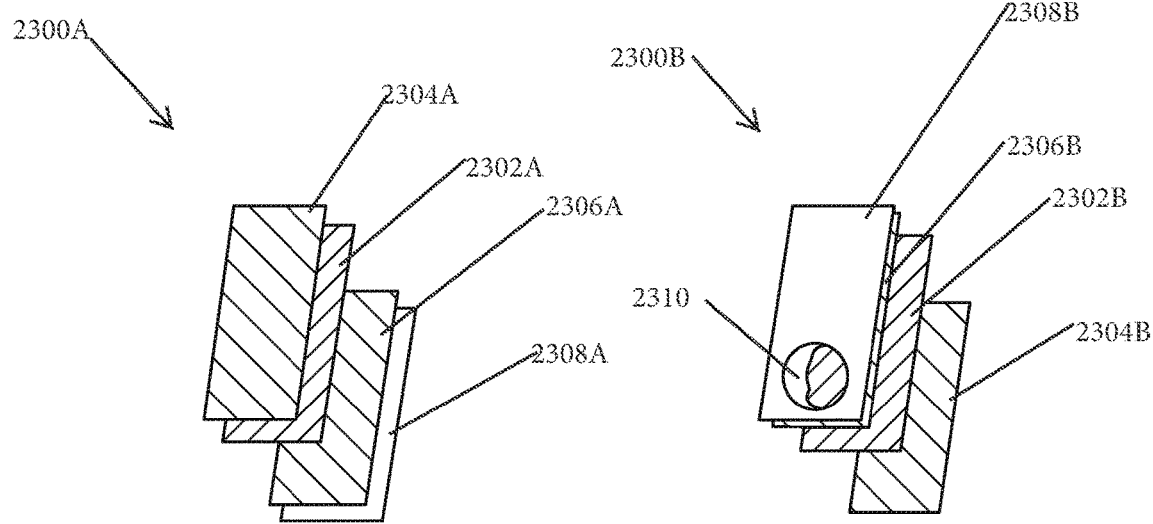
FIG. 23C illustrates multiple isometric views of two examples of gold electrodes in use.
Figure 23C:
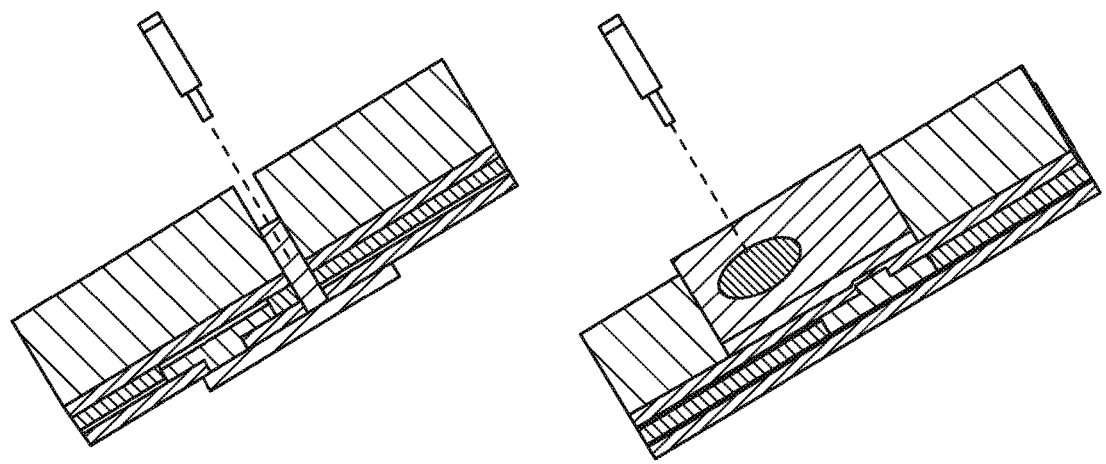

FIG. 23A illustrates an exploded view of a gold electrode, in accordance with at least one example of this disclosure. FIG. 23B illustrates an exploded view of a gold electrode, in accordance with at least one example of this disclosure. FIG. 23. Type I: The gold electrode is attached to the bottom of the device making contact with the internal fluidics via an opening on the underside. The pogo pin then makes connection with the gold electrode from above through a hole in the microdevice. Type II: The electrode is attached to the top of the device, makes contact with the internal fluidics via an opening in the top layer.

Gold electrodes are fabricated using a combination of polyester transparency sheets (PTS), double sided pressure sensitive adhesive (PSA) and commercially-purchased gold leaf. Electrodes consist of two key types. Type 1 electrodes are fabricated by adhering a PSA and PTS two layer construct onto an exposed sheet of gold leaf. The electrode design's outer shape is then ablated into this piece using a $CO_2$ laser. The gold electrode is attached to the bottom of the device making contact with the internal fluidics via an opening on the underside. A pogo pin then makes connection with the gold electrode from above through a hole in the microdevice.

Type 2 electrodes were fabricated by $CO_2$ laser ablating the internal electrode features in to two layer constructs of PTS and double sided PSA layer. This two-layer piece was then laid onto a sheet of exposed gold leaf, forming three-layer construct of PTS, PSA and gold leaf, Into this, the outer shape of the electrode design was ablated using the $CO_2$ laser system. The Type 1 electrode is attached to the top of a microfluidic device, making contact with the internal fluidics via an opening in the top layer. A pogo pin then makes connection with the gold electrode through the exposed region of the electrode.

FIG. 23A shows gold electrode 2300A, which can include gold leaf layer 2302A having paper backing layer 2304A that can be peeled away from gold leaf layer 2302A prior to use. Gold electrode 2300A can also include transparent layer 2308A, which can be adhered to gold leaf layer 2302A using adhesive layer 2306A.

FIG. 23B shows gold electrode 2300B, which can include gold leaf layer 2302B having paper backing layer 2304B that can be peeled away from gold leaf layer 2302B prior to use. Gold electrode 2300B can also include transparent layer 2308B, which can be adhered to gold leaf layer 2302B using adhesive layer 2306B. Gold electrode 2300B can include window 2310 through transparent layer 2308B and adhesive layer 2306B.

In some examples, adhesive layers 2306A and 2306B can be pressure sensitive adhesives, but can be other types of adhesives, such as heat sensitive adhesives, in other examples.

Until use, the gold leaf on both electrode types is protected by a paper backing. The electrodes are designed to be incorporated in a microfluidic device using double-sided PSA, such that a voltage can be applied to the internal reagents, while keeping them insulated from outside contamination. This innovation is important, as it had not been previously shown that gold leaf manufactured in this could be utilized due to its inherent fragility. This technique allows the user to stabilize and implement the gold leaf with relative ease. The method is also complementary to the print, cut and laminate fabrication methodologies, as it adopts the same design software (AutoCAD/Coreldraw), materials (PTS) and manufacture techniques ($CO_2$ laser). This has facilitated a holistic approach to fabricating devices in which the described electrodes are incorporated. This has, so far, been demonstrated with electrophoretic separation of DNA fragments. It is foreseen that the electrodes could be used for a wide range of electrophoretic separation applications, including clinical, forensic, and rural water analysis. In addition, the electrodes would potentially be applicable to electrochemistry applications. The main advantages of the materials described here are low cost, ease of manufacture and scalability.

A sole 638 nm laser diode was used with a 700 mW power setting.

One feature of the microdevice is the fact that it is a true hybrid. It is an octet hybrid, formed of polymethylmethacralate (PMMA), pressure sensitive adhesive (PSA), heat sensitive adhesive (HSA), polyethyl therephlalate, cyclic olefin copolymer, toner, polytetrafluoroethylene (PTFE) hydrophobic membrane filter, and gold leaf.

Overall, embodiments described herein provide for a method and a centrifugal microfluidic device that integrates reagent storage, nucleic acid liberation/extraction, multiplexed PCR amplification, electrophoretic separation, and fluorescent detection for rapid and portable nucleic acid analysis. Integrated nucleic acid analysis has been taught by U.S. Pat. No. 8,916,375B2, EP2817098A2, U.S. Pat. No. 8,018,593B2, etc. Nucleic acid extraction and amplification on a centrifugal microfluidic device have been taught by U.S. Pat. No. 8,303,911B2, CN205347420U, etc. Polymer loading for electrophoretic separation via centrifugal force has been taught by WO2003058224 A1. Reagent storage and release using blisters have been taught by US 20070263049 A1. Laser-actuated valves have been taught by WO 2010084190 A1. The reagents used for extraction, amplification, and separation are developed by MicroGEM, Promega, etc.

Thus, what is described herein is a portable and rapid nucleic acid analysis by integrating the above mentioned technologies on a single centrifugal microfluidic device with reagent storage and electrophoretic separation on the same centrifugal devices.

Figure 24A:
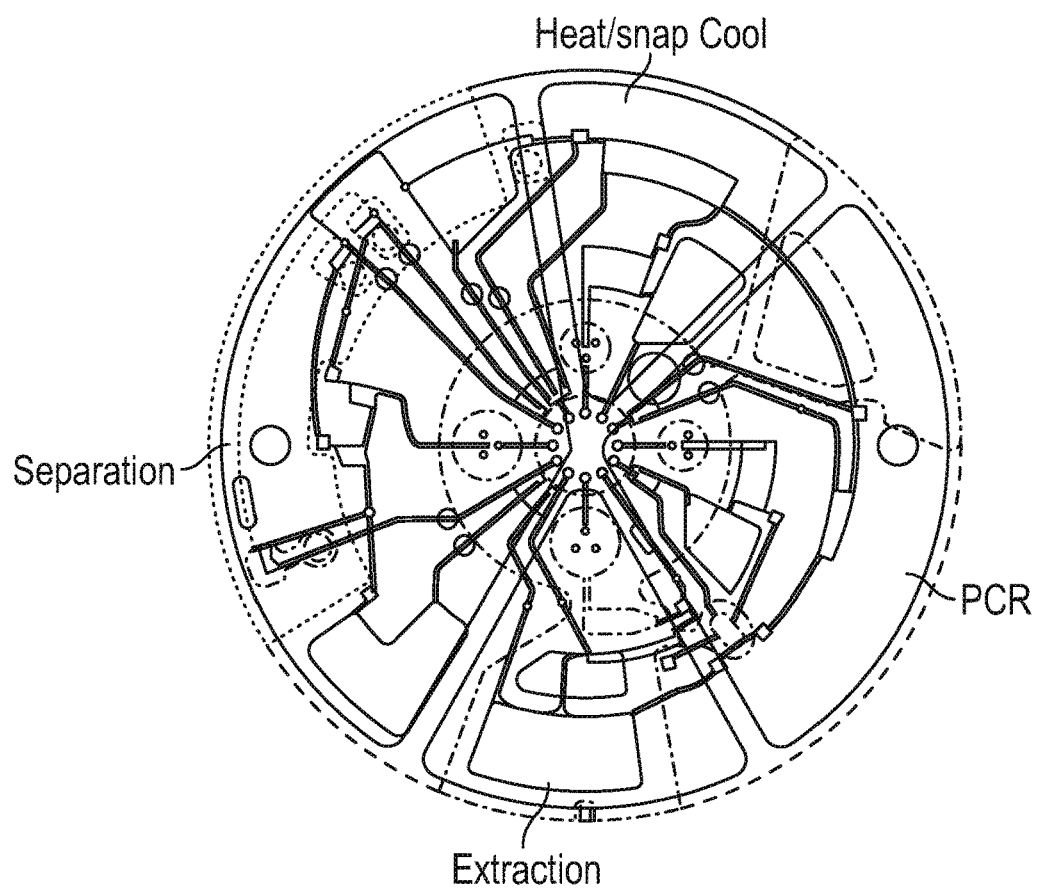
FIG. 24A illustrates a schematic view of an exemplary design of a disc, in accordance with at least one example of this disclosure.
Figure 24B:
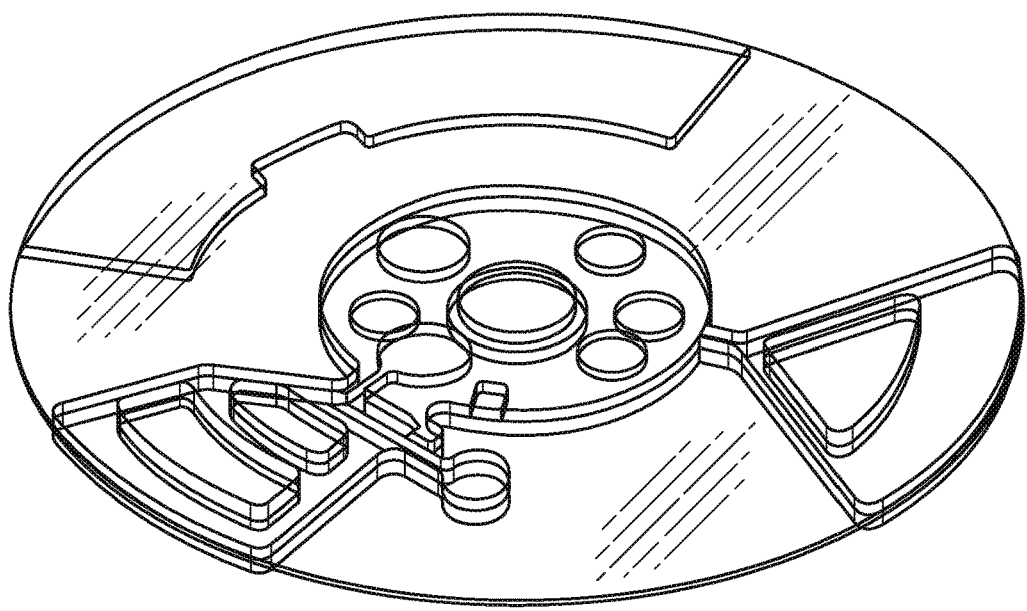
FIG. 24B illustrates a schematic view of a disk, in accordance with at least one example of this disclosure.
Figure 24C:
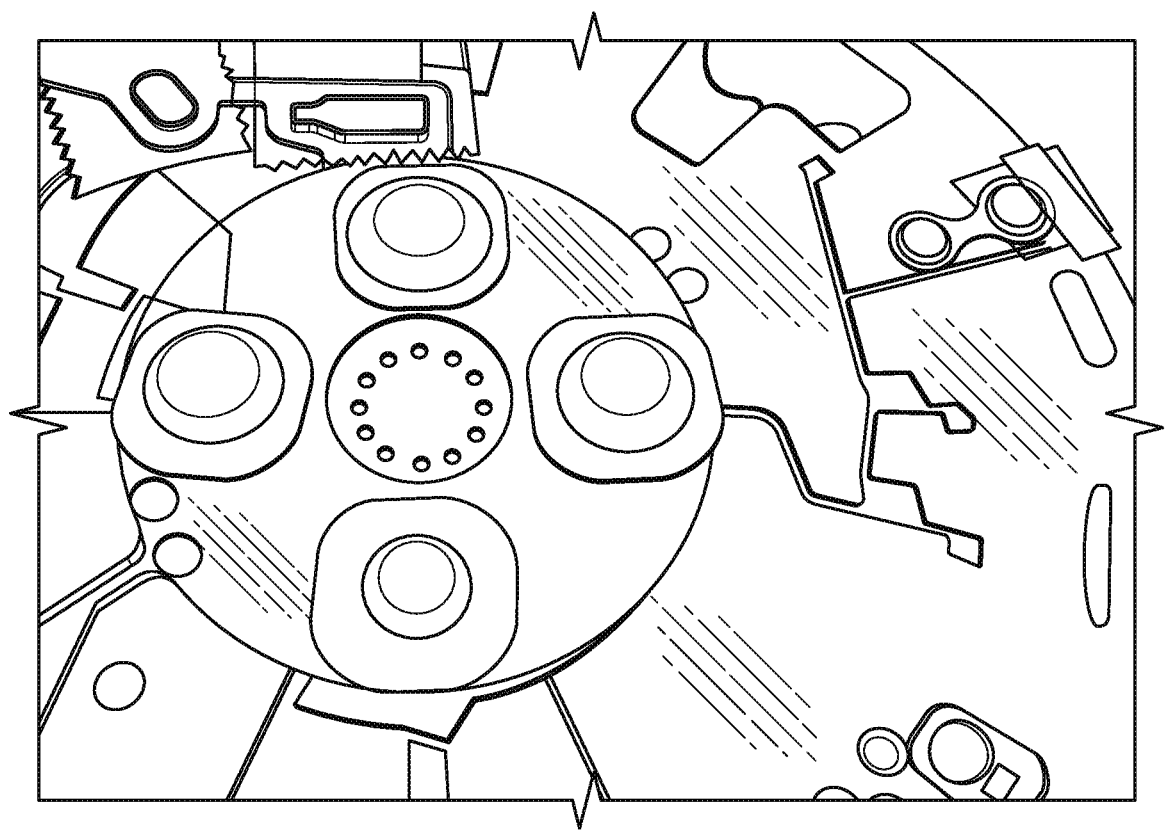
FIG. 24C shows an image of a chip with blisters and electrodes attached, in accordance with at least one example of this disclosure.

FIG. 24A illustrates a schematic view of an exemplary design of a disc, in accordance with at least one example of this disclosure. FIG. 24B illustrates a schematic view of a disk, in accordance with at least one example of this disclosure. FIG. 24C shows an image of a chip with blisters and electrodes attached, in accordance with at least one example of this disclosure. FIGS. 24A-C. A) Exemplary design of a FaSTR disc. B) 3D schematic of the design. C) Photo of the actual chip with blisters and electrodes attached.

FIG. 24 shows one embodiment of disc 2400. There are four domains on the disc—extraction 2402, PCR 2408, heat/snap cool 2406, and separation 2404. The input and output of each domain are shown in Table 3, and the operation protocol is shown in Table 4 and FIG. 24. FIG. 2529 are some specific designs.

TABLE 3

Input and output of each domain on FaSTR Disc

| | Domain/Step | Extraction | PCR | Heat/snap cool | Separation |
|---|---|---|---|---|---|
| Input | Reagents stored in blisters | EA1 enzyme | Water and PCR reagents | Water and ILS | Polymer |

TABLE 3-continued

Input and output of each domain on FaSTR Disc

| | Domain/Step | Extraction | PCR | Heat/snap cool | Separation |
|---|---|---|---|---|---|
| | | DNA in various forms | Buccal swab (1) | An aliquot of extracted DNA (2) | PCR product (3) | Denatured PCR product and ILS (4) |
| Output | | DNA in various forms | An aliquot of extracted DNA (2) | PCR product (3) | Denatured PCR product and ILS (4) | DNA profile |

TABLE 4

Current operation protocol of the FaSTR Disc

| Step | Speed(RPM) | Time (s) |
|---|---|---|
| 1) Move fluid from zygem chamber to swab chamber | 1000 | 30 |
| 2) Extraction protocol | | |
| 3) Laser valve 1 | | |
| 4) Move fluid to aliquot chamber | 2000 | 60 |
| 5) Laser valve 2 | | |
| 6) Move aliquot to mixing chamber | 2000 | 20 |
| 7) Move PCR reagent from blister to meter chamber | 1000 | 30 |
| 8) Laser valve a | | |
| 9) Move PCR reagent to mixing chamber | 1500 | 5 |
| 10) Laser valve 4 | | |
| 11) Move mixed reagents to PCR chamber | 2000 | 20 |
| 12) Degas step protocol | 2500 | 10 |
| 13) PCR step (30 cycles) | | |
| 14) Laser valve 5 | | |
| 15) Move PCR excess to waste | 2500 | 20 |
| 16) Laser valve 6 | | |
| 17) Transport PCR mix through snap cool | 2000 | 20 |
| 18) Release ILS from blister | | |
| 19) Laser valve 7 | | |
| 20) Transport snap cool (ILS) to chamber | 1000 | 5 |
| 21) Degas step protocol | 2500 | 10 |
| 22) Polymer load | 2500 | 300 |
| 23) Laser valves 8 + 9 | | |
| 24) Remove polymer excess and move sample to separation arm | 2500 | 30 |
| 25) Laser valve 10 + 11 | | |
| 26) Fill remaining separation arms | 2500 | 30 |

Through the addition of a flocked swab (Copan Diagnostic custom made swab), liquid and cells collected from a participant are easily stored through capillary action in the nylon strands of the swab head. This storage is sufficient enough to allow the zygem enzyme and buffer to encapsulate the cells and then allow the internal contents (DNA) of the cells to be released during heating at 75° C. for 2.5 minutes. As the ruptured cells, and now DNA, are loosely held between these fibers, centrifugal forces are great enough to easily drive the fluid and DNA to chambers downstream that allow proper metering to occur for PCR amplification. The addition of PMMA to this extraction process, allows room for a flocked swab to be included in the device with a small footprint, but also allows the proper volumes of enzyme, buffer, and water, for sufficient concentrations of DNA for PCR amplification. As the PMMA allows these volumes to be utilized with the device, no optimization of the extraction chemistry had to be done.

Figure 25:
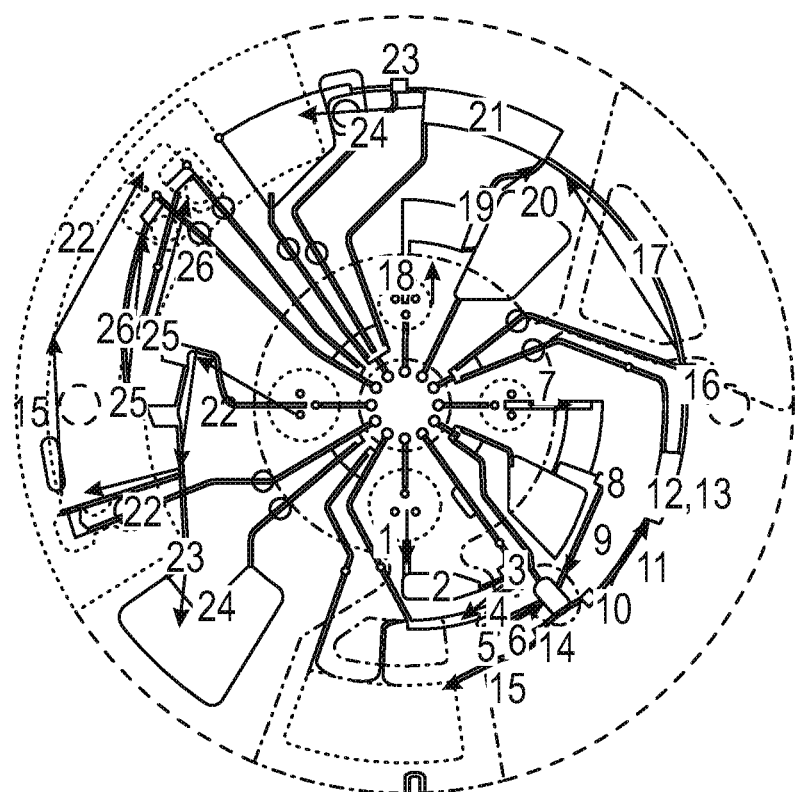
FIG. 25 illustrates a fluidic flow schematic corresponding to the steps listed in Table 4, in accordance with at least one example of this disclosure.

FIG. 25 illustrates a fluidic flow schematic corresponding to the steps listed in Table 4, in accordance with at least one example of this disclosure.

FIG. 25 and Table 5, demonstrate the introduction of the PMMA into the microfluidic device, as well as data showcasing the reproducibility and extraction efficiency of the proposed method.

TABLE 5

| Sample | DNA Conc. 1 (ng/µL) | DNA Conc. 2 (ng/µL) | DNA Conc. 3 (ng/µL) | DNA Conc. 4 (ng/µL) | Average (ng/µL) |
|---|---|---|---|---|---|
| Participant 1 | 3.48 | 3.02 | 9.52 | 3.01 | 4.76 ± 3.18 |
| Participant 2 | 7.59 | 5.85 | 5.97 | 4.81 | 6.06 ± 1.15 |
| Participant 3 | 10.27 | 10.98 | 6.29 | 3.65 | 7.80 ± 3.45 |

| Number of Samples | Overall Average DNA Conc. (ng/µL) |
|---|---|
| 20 | 5.85 ± 2.41 |

Figure 26:
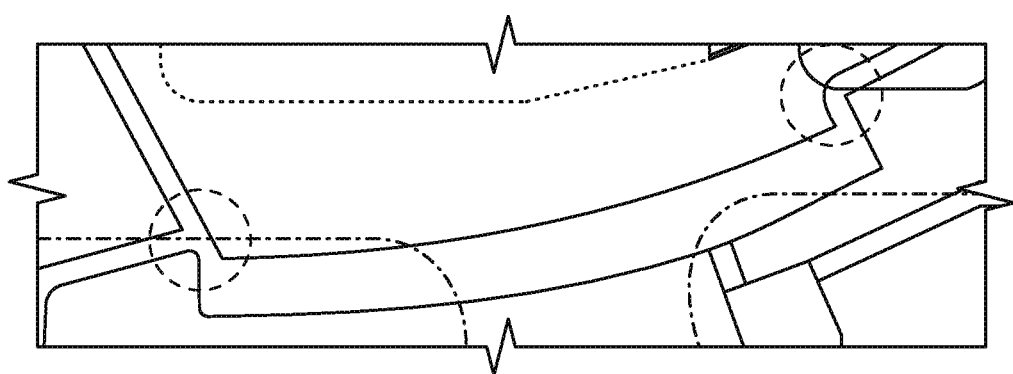
FIG. 26 illustrates a schematic view of channels of an aliquot chamber, in accordance with at least one example of this disclosure.

FIG. 26 illustrates a schematic view of channels of an aliquot chamber, in accordance with at least one example of this disclosure. FIG. 26. The channels of the aliquot chamber (shown in red circles) in one embodiment are designed to minimize the air/liquid interface to allow for more precise metering.

FIG. 26 displays the ability to use DNA extracted from our method for STR PCR and analysis. From this figure it can be concluded that the extracted DNA is in the correct mass and condition to be used for STR analysis and human identification.

Figure 27:
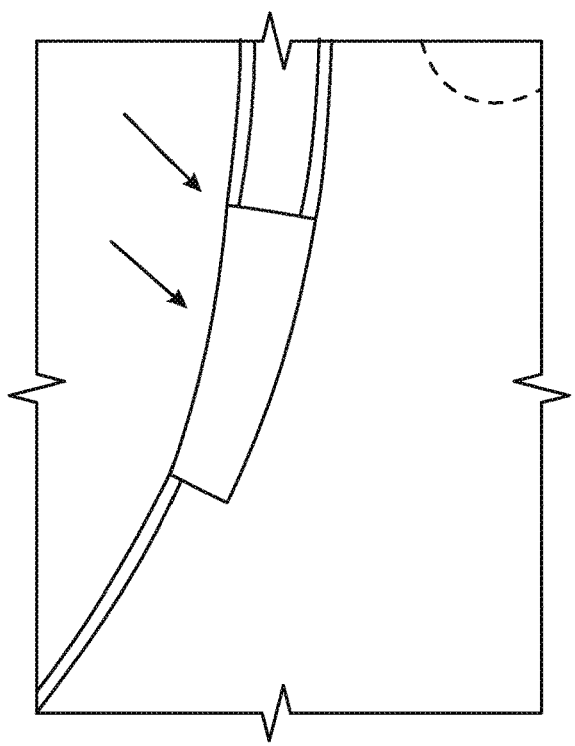
FIG. 27 illustrates a schematic view of a polymerase chain reaction chamber wall of a chip, in accordance with at least one example of this disclosure.

FIG. 27 illustrates a schematic view of a polymerase chain reaction chamber wall of a chip, in accordance with at least one example of this disclosure. FIG. 27. The slope of the PCR chamber wall in one embodiment is tuned to allow air to escape from the vent line, which allows for degassing.

Figure 28:
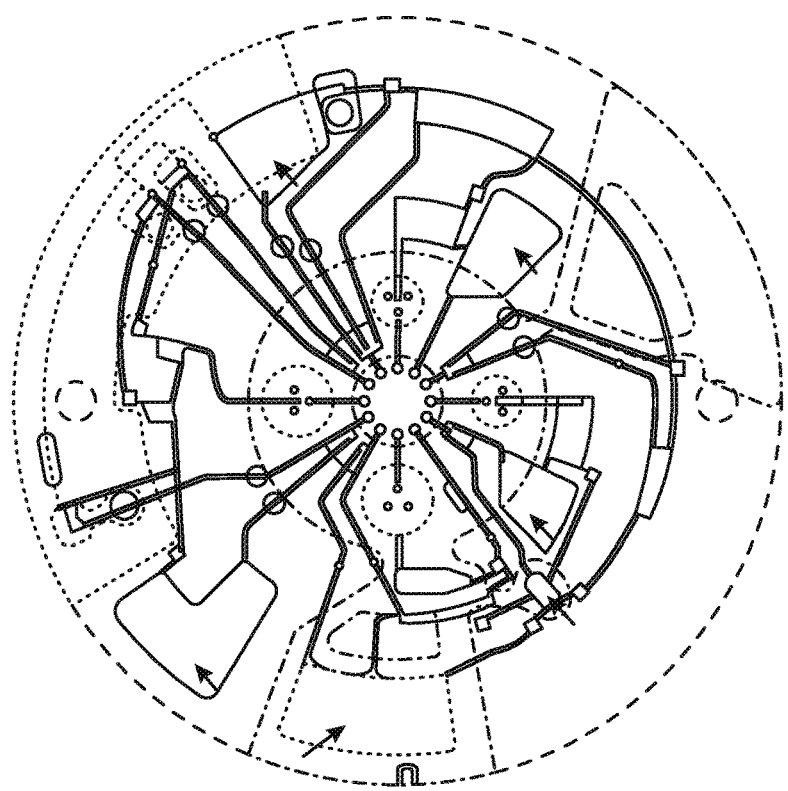
FIG. 28 illustrates a schematic view of chambers of a chip, in accordance with at least one example of this disclosure.

FIG. 28 illustrates a schematic view of chambers of a chip, in accordance with at least one example of this disclosure. FIG. 28. Liquid tends to fill narrow channels such as vent lines due to capillary force, which causes problems in fluidic flow. To solve this problem, the volumes of the arrowed chambers are designed to be much larger than liquid volumes to create an empty space between the liquid and vent line.

Figure 29:
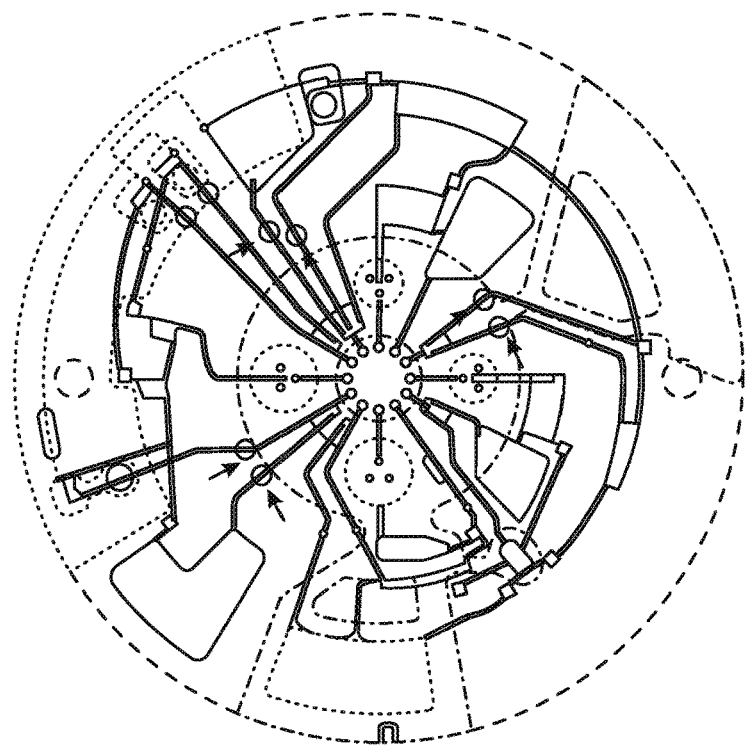
FIG. 29 illustrates a schematic view of surface-tension valves and overflow reservoirs of a chip, in accordance with at least one example of this disclosure.

FIG. 29 illustrates a schematic view of surface-tension valves and overflow reservoirs of a chip, in accordance with at least one example of this disclosure. FIG. 29. As another measure to prevent liquid from filling vent lines, these arrowed chambers are created as surface-tension valves and overflow reservoirs to stop the liquid.

Figure 30:
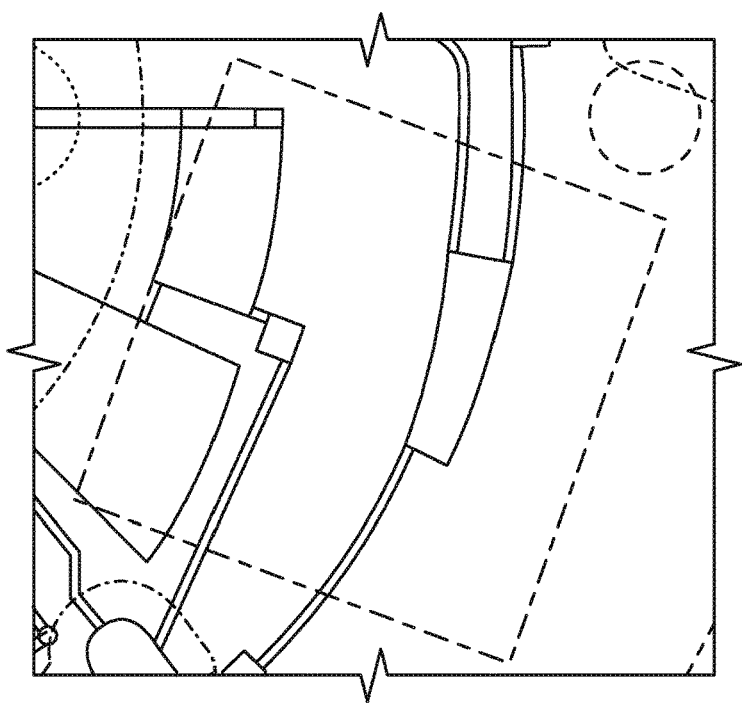
FIG. 30 illustrates a schematic view of a heated area during a polymerase chain reaction, in accordance with at least one example of this disclosure.

FIG. 30 illustrates a schematic view of a heated area during a polymerase chain reaction, in accordance with at least one example of this disclosure. FIG. 30. The white square represents the heated area during PCR. To prevent evaporation, in one embodiment the volume of the PCR chamber and the angles of the channels are tuned so that the liquid/air interface is located close to but outside the heated area.

Figure 31:
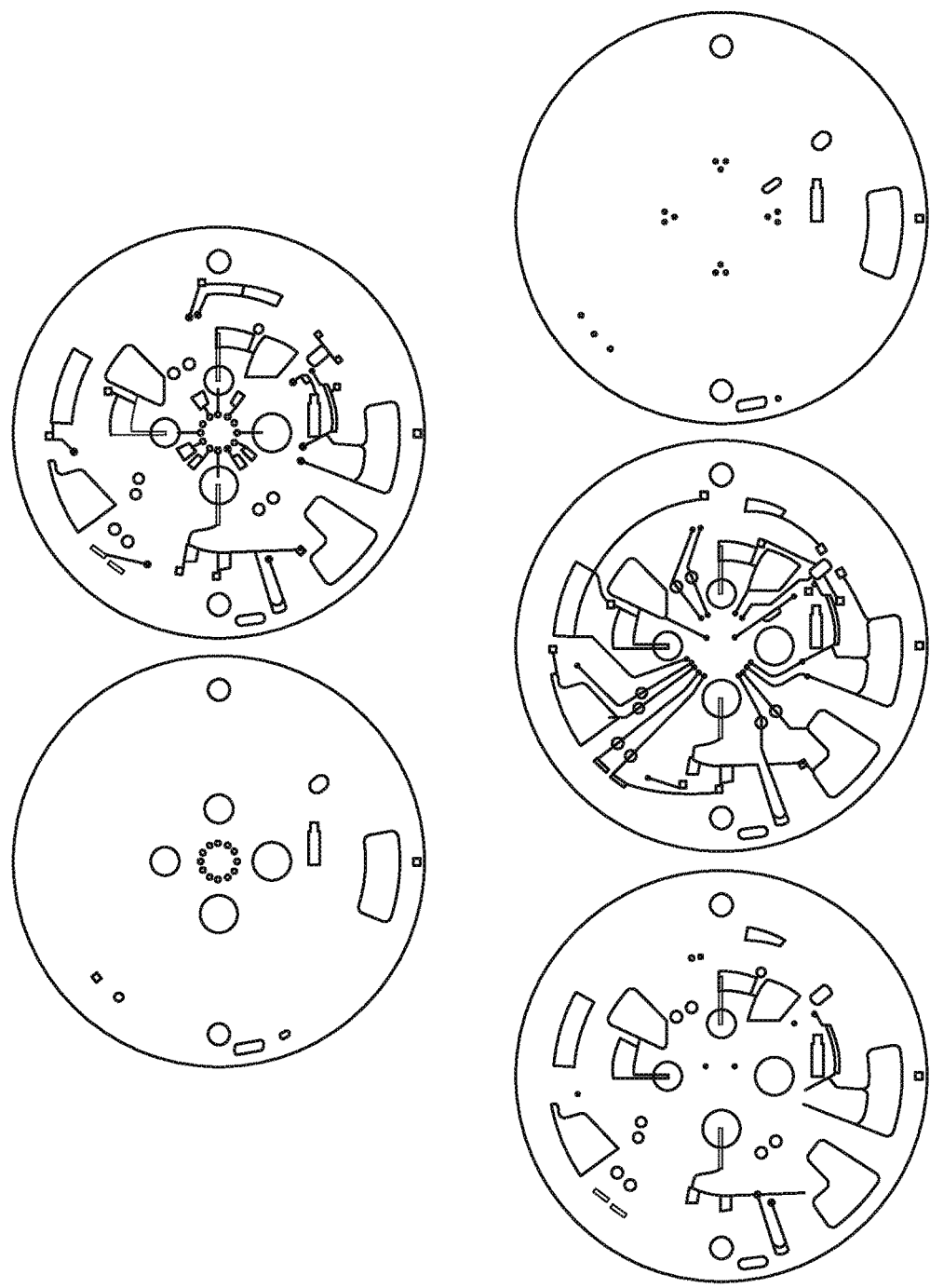
FIG. 31 illustrates several schematic views of a multilayer architecture for a chip, in accordance with at least one example of this disclosure.

FIG. 31 illustrates several schematic views of a multilayer architecture for a chip, in accordance with at least one example of this disclosure. FIG. 31. Exemplary multilayer architecture for the faSTR disc.

Figure 32:
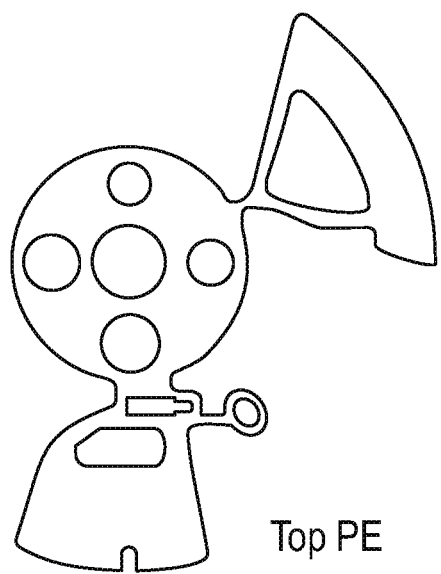
FIG. 32 illustrates a schematic view of PMMA layers, in accordance with at least one example of this disclosure.
Figure 32:
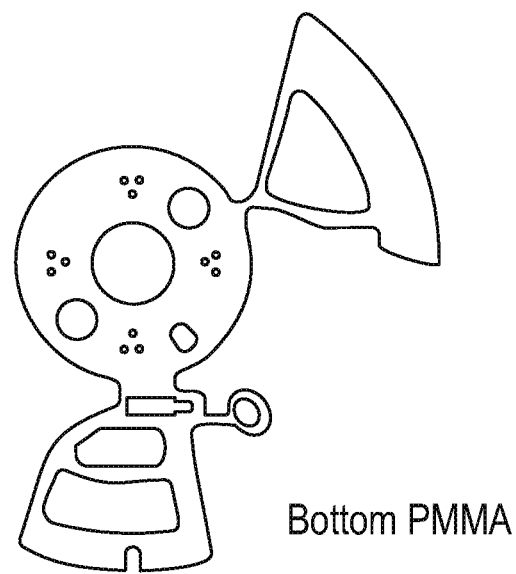
Figure 32:
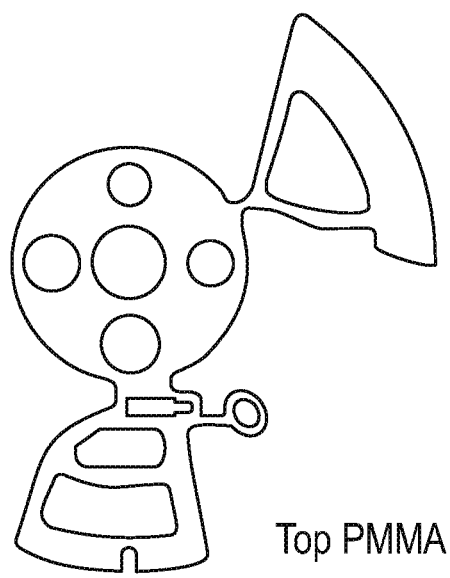
Figure 32:
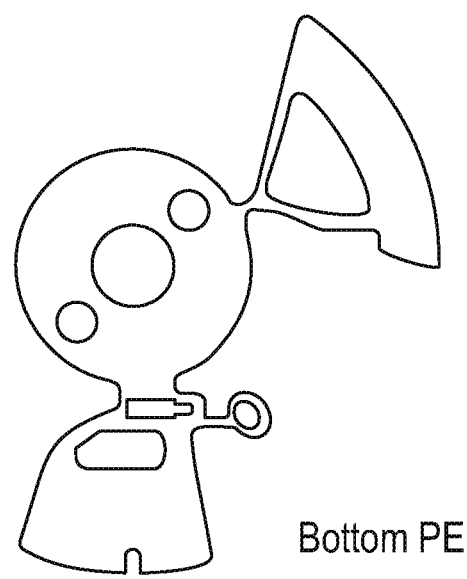

FIG. 32 illustrates a schematic view of PMMA layers, in accordance with at least one example of this disclosure.

Figure 33:
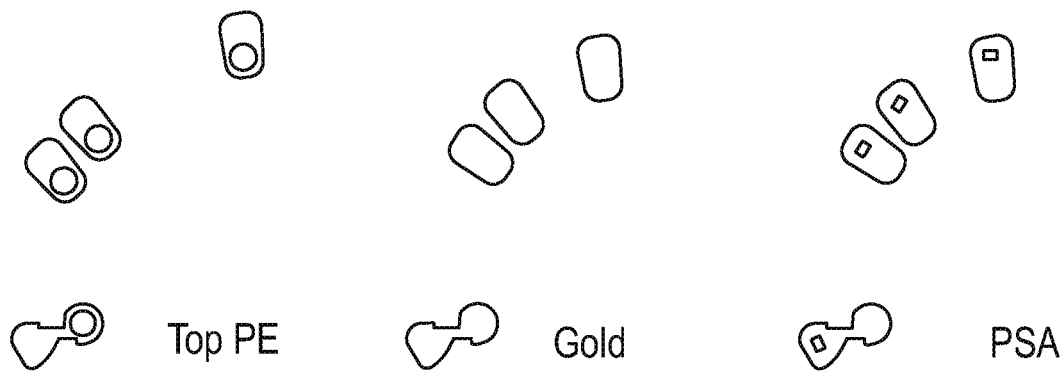
FIG. 33 illustrates a schematic showing a design of electrodes, in accordance with at least one example of this disclosure.

FIG. 33 illustrates a schematic showing a design of electrodes, in accordance with at least one example of this disclosure.

Figure 34:
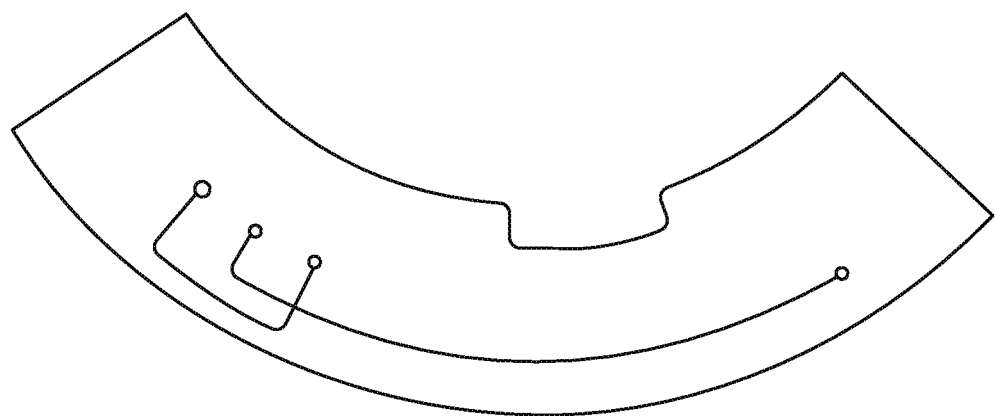
FIG. 34 illustrates a schematic view of a chip for separation, in accordance with at least one example of this disclosure.

FIG. 34 illustrates a schematic view of a chip for separation, in accordance with at least one example of this disclosure. FIG. 34. Exemplary design of COC chip for separation.

Figure 35:
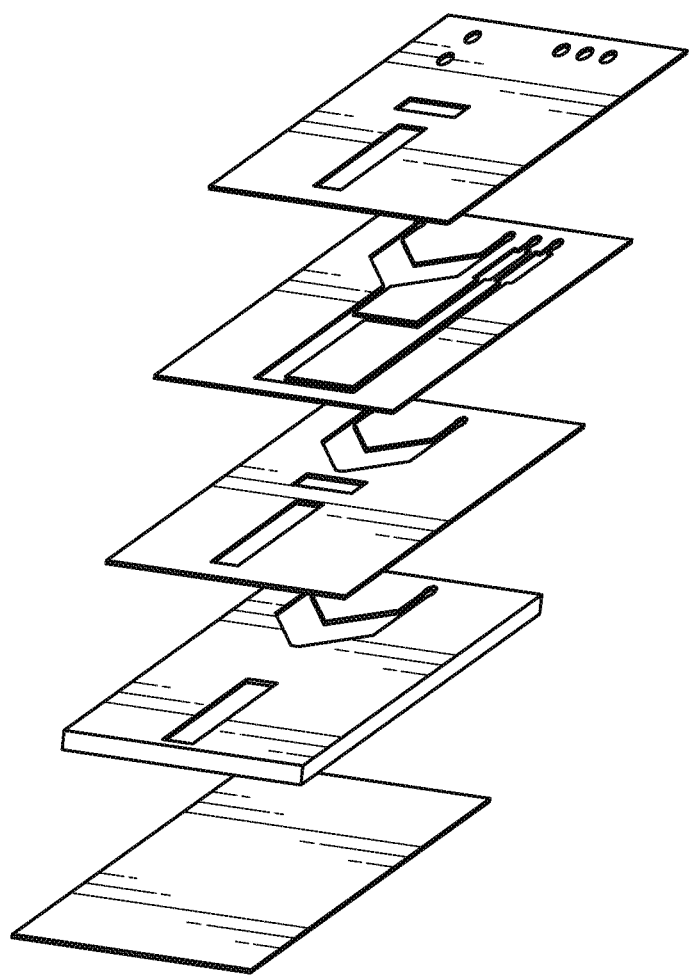
FIG. 35 illustrates a schematic of layers of an extraction microdevice, in accordance with at least one example of this disclosure.

FIG. 35 illustrates a schematic of layers of an extraction microdevice, in accordance with at least one example of this disclosure. FIG. 35. Schematic of the various layers required to create a DNA extraction microdevice.

Extracted DNA is spun out of the extraction chamber and aliquoted prior to PCR amplification. Centrifugal force is used to control the fluid flow and metering. During PCR thermocycling, the disc is stationery and clamped between the dual Peltier apparatus. Following PCR, the product is moved (via centrifugal force) into the heat snap cool chamber for sample preparation prior to microchip electrophoresis.

The thin nature of the device (e.g., due to materials used) allows for rapid heat transfer, while simultaneously allowing for a higher surface area of the PCR chamber that is in contact with the dual Peltier during heating/cooling. Likewise, the use of a dual Peltier allows for more rapid heat transfer since it is in contact with the top and bottom of the PCR chamber.

After the separation (the sample has undergone heat, snap cool), the HMPAM polymer that was released by blister actuation at the beginning of the run, is spun into the COC separation channel at 2,500 rpm for 10 minutes. Polymer concentration was optimized at 1% of high molecular weight HMPAM to 4% low molecular weight HMPAM. As the polymer can become too viscous to allow proper centrifugal loading, this concentration was chosen to allow rapid centrifugal polymer filling (<10 minutes), but also allow the appropriate separation resolution (2 base resolution) for STR Human ID analysis. The sample, buffer, and sample waste chambers remain empty during channel filling to allow proper air displacement to occur to facilitate bubble-less loading. In order to complete the filling, the sample chamber is first filled at 2,500 rpm for 30 seconds, allowing contact between the DNA sample and the polymer in the separation channel. The sample chamber is designed in a way that allows any formation of air bubble's to displace at the top of the chamber, ultimately allowing fluid connection between COC channel inlet and gold leaf electrode. A valve is then opened to allow excess polymer to flow into a waste chamber, thereby, metering two chambers with additional polymer (2,500 rpm for 30 seconds, done at same time as sample loading). The addition of an excess waste chamber was due to the large volume of polymer (100 µL) required to generate enough pressure to load the channel through centrifugal means. Polymer connections (touching) with adjacent chambers may cause fluctuations in electrical connectivity that ultimately result in an improper DNA separation. The aliquoted polymer after excess polymer removal is then used for sample waste and buffer chamber filling at 2,500 rpm for 30 seconds, allowing contact with the polymer located in the outlets of the separation channel. These chambers were designed to fill with a sufficient volume of polymer (>10 µL) to facilitate proper connection between electrode and polymer located in the separation channel. This filling process was paramount to providing appropriate DNA separation, as it eliminated any possible bubble formation, which can cause complications in electrical connection necessary for electrophoresis.

FIG. 37 displays a schematic demonstrating various layers of a sole separation device that is comprised of polyethylene terephthalate, toner, a cyclic olefin copolymer separation chip, pressure sensitive adhesive, and gold leaf. FIG.

Figure 39:
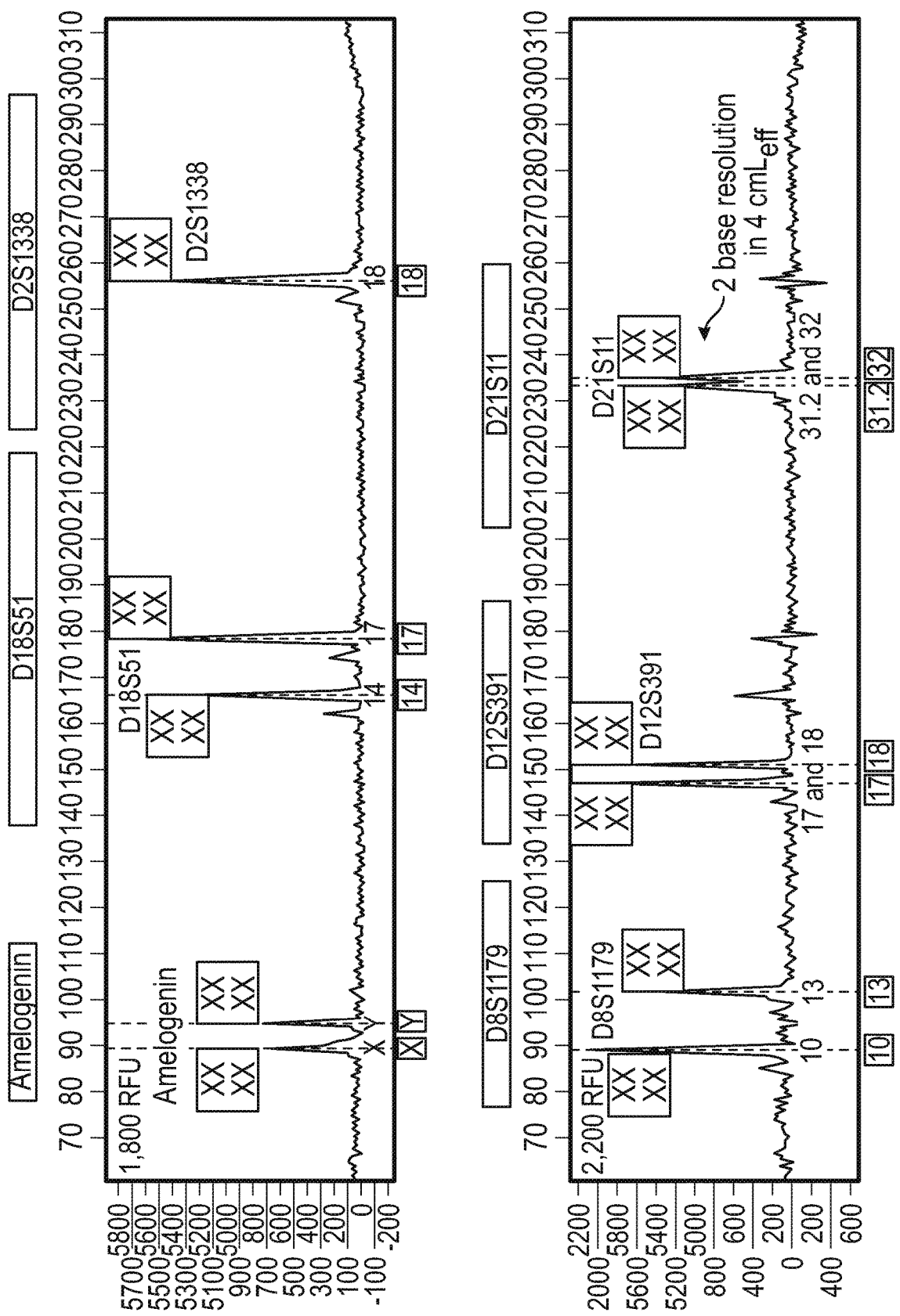
FIG. 39 illustrates an STR profile after separation on a fully integrated device at 6 different loci using a multi-colored detection system. The strong profile identified all loci correctly, when compared to a separation performed on an ABI 310 instrument of the same sample, in accordance with at least one example of this disclosure.

38 has images showcasing the addition of the gold electrodes and architectural features utilized in our integrated device. Finally, FIG. 39 is a 6 loci STR profile that was obtained through the use of a hybrid separation device (materials listed above), where electrical current and connection was obtained through use of gold leaf electrodes.

Once the PCR amplification is completed, the product volume is spun down to another chamber, where the internal lane standard and water, are then subsequently added. The sandwich Peltier system then completely covers the chamber and heats to 95° C. for 1 minute. The Peltiers are then opened and the disc is spun at 1,000 rpm for 10 seconds. This unique "degassing" step was included to remove bubbles that are a common occurrence in centrifugal microfluidic processes, especially when heating is included in the process. By eliminating bubbles, there is no air expansion, which decreases unwanted fluid movement as well as sample evaporation. The chamber is then heated to 95° C. for 3 minutes, ultimately denaturing the DNA, and then is rapidly cooled to 10° C. to keep single stranded DNA from reannealing. The cooling rate of the Peltier system, which is dictated by our optimized PID parameters and code, is fast enough to perform a successful heat, snap cool, which allows for downstream DNA electrophoresis to occur properly.

Figure 40:
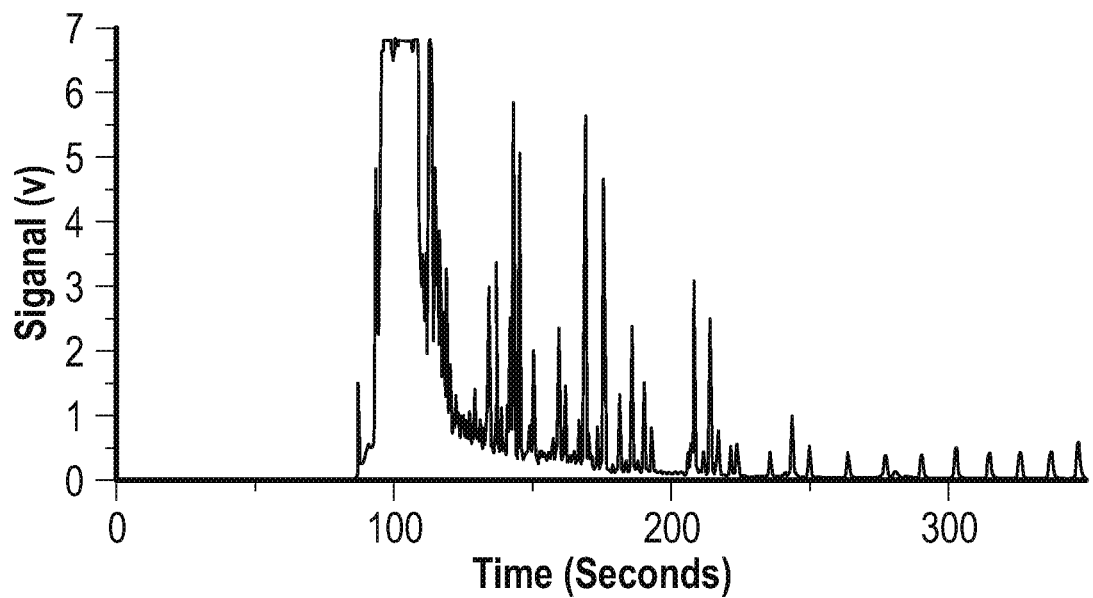
FIG. 40 illustrates an electropherograms demonstrating the similarity between the heat and snap-cool method versus the traditional (literature) method, in accordance with at least one example of this disclosure.
Figure 40:
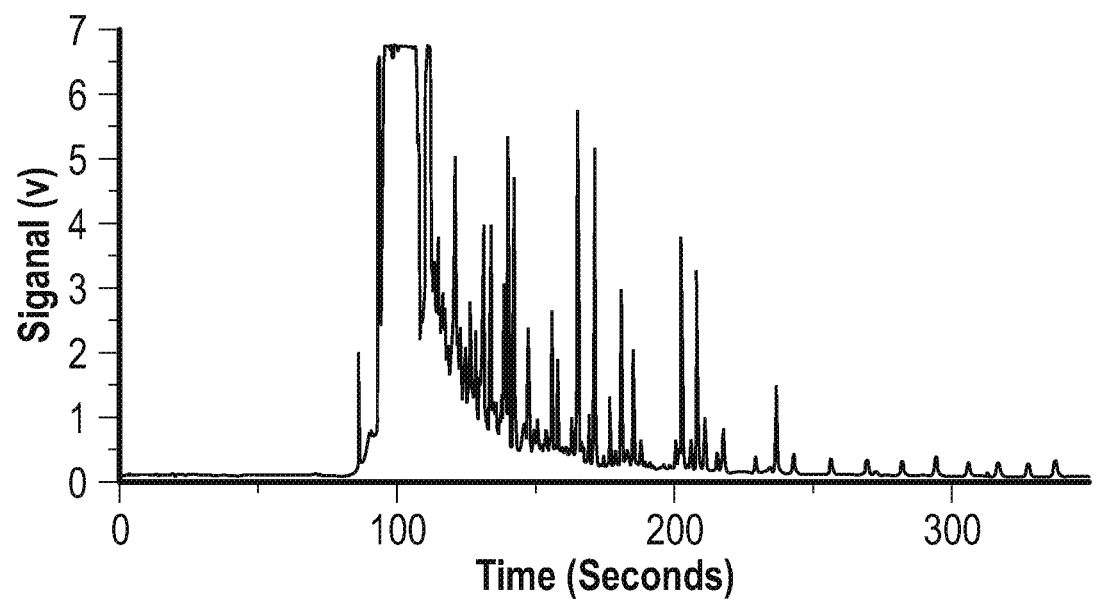

FIG. 40 demonstrates an electrophoretic separation with a sample that was heat, snap cooled (HSC) in tube, in the traditional manner, with a commercial thermocycler. The electropherogram displays an electrophoretic separation on a sample that was heat, snap cooled with the method described above using a Peltier system. The agreement between the two electropherograms, as far as the peak spacing, shows the ability to obtain a denatured DNA sample from the discussed method in the same manner the traditional way would offer.

A centrifugal microfluidic device can be configured to prepare a sample for nucleic acid analysis. The centrifugal microfluidic device can include a body, an extraction portion of the body, a polymerase chain reaction portion of the body, a heat and snap-cool portion of the body, and a separation portion of the body. The body can be formed from of a plurality of layers. The extraction portion of the body can include a first reagent storage chamber and a liberation chamber. The polymerase chain reaction portion of the body can include a mixing chamber and a second reagent chamber connected to the mixing chamber, the second reagent chamber having a volume that is larger than a volume of a second reagent. The separation portion of the body can include a polymer loading reservoir and polymer channels and a separation channel connected to the polymer channels and connected to an electrode.

In some examples, the liberation chamber can be configured to receive a sample and configured to receive a first reagent from the first reagent storage chamber and configured to produce a first fluid. In some examples, the mixing chamber can be configured to mix the first fluid with a second reagent to create a second fluid and configured to degas the second fluid.

In some examples, the heat and snap-cool portion can be configured to mix the second fluid with a third reagent to create a third fluid, and can be configured to heat and snap-cool the third fluid. In some examples, the polymer loading reservoir and polymer channels can be configured to load a polymer, and the separation channel can be configured to conduct electrophoretic separation on a mixture of the polymer and the third fluid to create a fourth fluid.

In some examples, at least one of the plurality of layers can be comprised of poly methyl methacrylate. In some examples, the plurality of layers can be adhered by a heat sensitive adhesive.

In some examples, the electrode can include a gold leaf layer, an adhesive layer adhered to the gold leaf layer, and a transparent layer adhered to adhesive layer.

A method of preparing nucleic acid for analysis using a centrifugal microfluidic device can include moving a first reagent from a first reagent chamber to an extraction chamber using centrifugal force. A first fluid can be moved to a mixing chamber using centrifugal force. A second reagent can be released into the mixing chamber through a metering chamber using centrifugal force. The first fluid can be mixed with the second reagent to create a third fluid.

The third fluid can be moved to a polymerase chain reaction chamber using centrifugal force. The third fluid can be degassed using centrifugal force. The third fluid can be moved to a snap-cool chamber using centrifugal force. A third reagent can be transported using centrifugal force to the snap-cool chamber to form a fourth fluid. A polymer can be loaded into a polymer chamber using centrifugal force. The fourth fluid can be mixed with the polymer to create a fifth fluid.

In some examples, the first fluid can be extracted from a sample by heating the sample and the first fluid can be moved to an aliquot chamber using centrifugal force In some examples, the third fluid can be cyclically heated and cooled, and the third fluid can be snap-cooled. In some examples, the fourth fluid can be degassed using centrifugal force and the fourth fluid can be moved to a separation chamber using centrifugal force. In some examples, nucleic acid can be separated from the fifth fluid through electrophoretic separation. A method to extract, amplify and separate nucleic acid in a microfluidic device having a plurality of chambers and channels can include a) introducing cells having nucleic acid to a first chamber (such as an extraction chamber) of the microfluidic device and subjecting the cells in the first chamber to conditions that lyse the cells. The method can further include b) subjecting the first chamber to centrifugal force, thereby allowing the lysate or a portion thereof having nucleic acid to be distributed to a second chamber (such as a polymerase chain reaction chamber) through a first channel in the microfluidic device. The method can also include c) combining the lysate or portion thereof and reagents for amplification of the nucleic acid, thereby providing a second mixture. The method can also included) subjecting the second chamber to centrifugal force, thereby allowing gas to be expelled from the second mixture. The method can include e) subjecting the second mixture in the second chamber to cyclic amplification, thereby providing amplified nucleic acid. The method can further include f) subjecting the second mixture having the amplified nucleic acid to centrifugal force, thereby allowing the amplified nucleic acid to be distributed to a third chamber (such as a snap-cool chamber) in the microfluidic device through a second channel, which third chamber reduces the temperature of the amplified nucleic acid to provide denatured nucleic acid. The method can also include g) subjecting the third chamber to centrifugal force, thereby allowing gas to be expelled from the second mixture. The method can additionally include h) combining the amplified nucleic acid in the third chamber with a polymer, thereby providing a fourth mixture. The method can also include i) introducing the fourth mixture into a separation channel (such as a polymer chamber) using centrifugal force.

In some examples, that the conditions in a) can be exposure to enzyme, a chaotropic solution or heat. In some examples, the reagents for amplification prior to combining can be in two or more separate storage chambers In some examples, one or more valves can separate the chambers. In some examples, a Peltier system can be employed for heating in the cyclic amplification. In some examples, the second chamber can be formed of Pe toner.

In some examples, the separation channel can be comprised of cyclic olefin copolymer, polyester, pressure sensitive adhesive, toner, or any combination thereof.

In some examples, the microfluidic device can include a gold electrode. In some examples, the microfluidic device can be formed of polytetrafluoroethylene (PFTE) hydrophobic membrane filter, gold leaf, polyethyl terephthalate, toner, polymethylmethacrylate (PMMA), heat sensitive adhesive, pressure sensitive adhesive, or any combination thereof.

In some examples, the polymer can include hydrophobically modified poly(acrylamide) HMPAM. In some examples, the separation channel can be comprised of gold leaf.

In some examples, the first chamber can include magnetic beads. In some examples, one or more of the valves can be passive valves.

Example 5

Separation

The disclosure provides, among other things, a centrifugal microfluidic device using a combination of inexpensive materials including cyclic olefin copolymer (COC), polyester (Pe), and pressure-sensitive adhesive (PSA), for the separation of DNA. Devices are fabricated using the previously described print-cut-laminate (PCL) technique, where the toner-coated middle layer limits the detection of background auto fluorescence around the channel.

Injection molded separation devices were mounted to PCL-fabricated fluidic layers to create an integrated device that reduces overall injection molding/fabrication challenges.

Manufacture

During the PCL fabrication method, ridges of melted toner and Pe adhesive form from the ablation of the material during the cutting process. These ridges can have negative impacts when bonding, causing leaking and eventually leading to delamination. To fix this issue, the present inventors employ a 'pre-lamination' step prior to final bonding, in which the cut toner layers are placed between two non-bonding materials and introduced into the bonding laminator. This step smooths all of the formed ridges and promotes more complete bonding of the final devices.

When introducing COC as top and bottom layers of the devices, it was noted that the toner did not provide adequate adhesion for strong bonding between layers, and delamination was observed. To overcome this issue, each surface was plasma oxidized for 7 minutes prior to the final lamination step. The plasma oxidation improves the interaction of the toner with the COC layers and delamination was no longer observed Previously, channel dimensions in separation devices using similar materials were limited to the number of toner layers printed on the substrate. As mentioned above, PCL method was used.

The viscosity of the sieving polymer makes loading long, narrow channels difficult and time consuming. Polymer reservoirs and separation channel shapes were designed to facilitate the ease of polymer loading. These designs follow the direction of the rotation and take advantage of both the radial force and the drag force. The successful loading of a 4% sieving polymer via centrifugation in these various designs was demonstrated.

The toner used on the middle layer of the device is porous in nature and results in bubble formation in the channels when the device is heated. The present inventors are able to remove bubbles and prevent further creation of bubbles by heating and spinning the device pre- and post-loading of polymer, prior to separation.

PMMA was added as an additional layer(s). Besides minimize footprint and accommodate large objects, we also use PMMA to balance the weight of the whole device.

Heat sensitive adhesive (HSA) was added to the disc fabrication process to facilitate an easier alignment process, as the complete device is comprised of many layers. The use of pressure sensitive adhesive only allows a user one chance to successfully align a piece of the device before it is permanently adhered. Introducing HSA allows a user to correctly confirm the appropriate position of the layers without a "one shot chance", because the adhesive properties of the HSA are only activated upon heat. As heat and pressure active the adhesive, the current lamination process already implemented in the fabrication process (one pass through a pouch thermal laminator at 200° C. with a roller speed of 8 mm/s) is suitable to complete the bonding of the device without alteration to the method or additional/different heating equipment. In addition, the HSA properties allow it to be used in the laser cutting protocol, with optimized power and speed parameters (15% power, 10% speed) found to be capable of vector ablation on the 50 Watt $CO_2$ VersaLaser system, which, ultimately together, create the microfluidic architecture.

Through the addition of a flocked swab (Copan Diagnostic custom made swab), liquid and cells collected from a participant are easily stored through capillary action in the nylon strands of the swab head. This storage is sufficient enough to allow the zygem enzyme and buffer to encapsulate the cells and then allow the internal contents (DNA) of the cells to be released during heating at 75° C. for 2.5 minutes. As the ruptured cells, and now DNA, are loosely held between these fibers, centrifugal forces are great enough to easily drive the fluid and DNA to chambers downstream that allow proper metering to occur for PCR amplification. The addition of PMMA allows room for a flocked swab to be included in the device with a small footprint, but also allows the proper volumes of enzyme, buffer, and water, for sufficient concentrations of DNA for PCR amplification. As the PMMA allows these volumes to be utilized with the device, no optimization of the extraction chemistry had to be done.

Data using PMMA in the microfluidic device showed the reproducibility and extraction efficiency of the method. The extracted DNA is the correct mass and in condition to be used for STR analysis and human identification.

Figure 36:
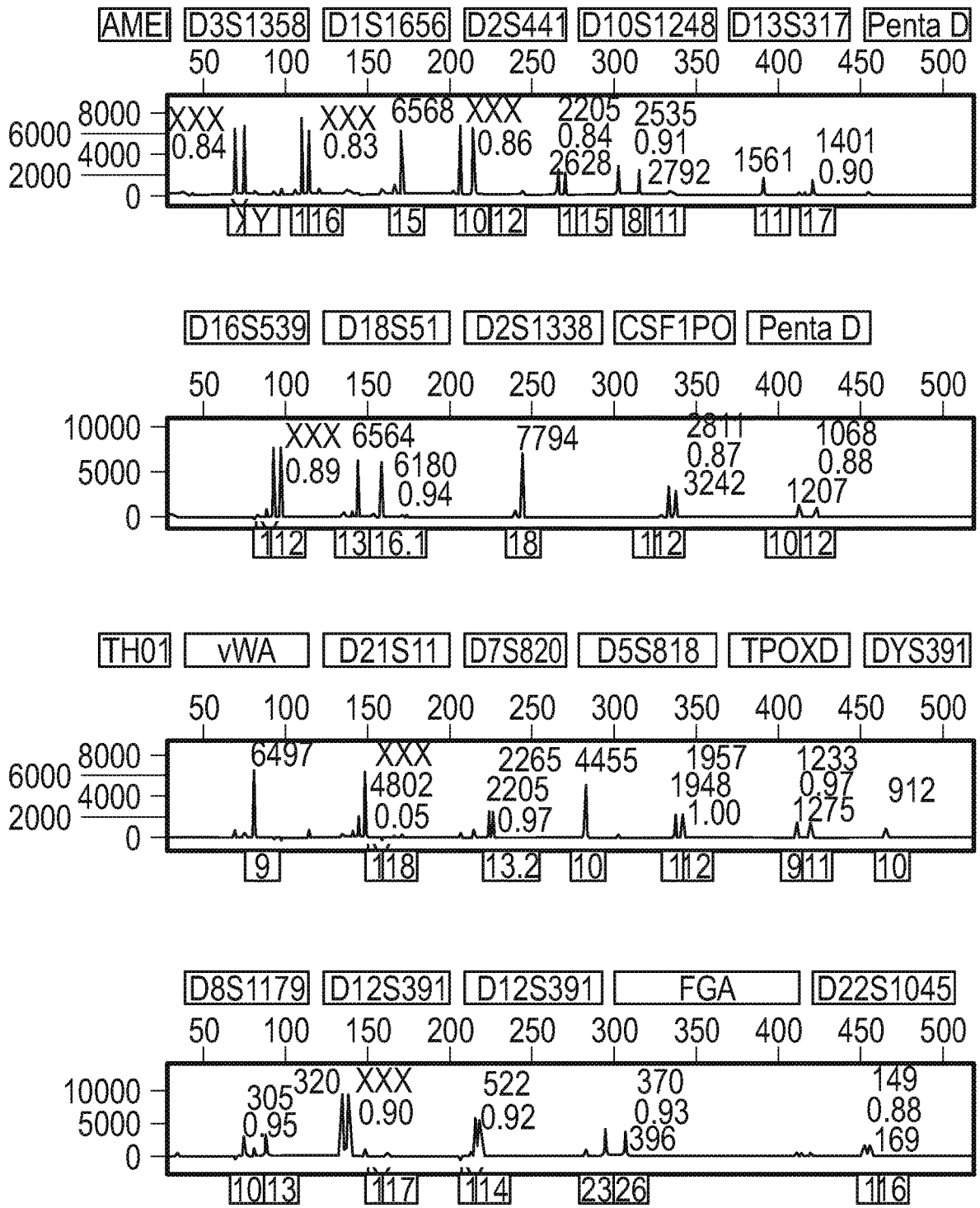
FIG. 36 illustrates STR electropherograms from two different individuals after DNA extraction using a PeT-PMMA microdevice, in accordance with at least one example of this disclosure.
Figure 36:
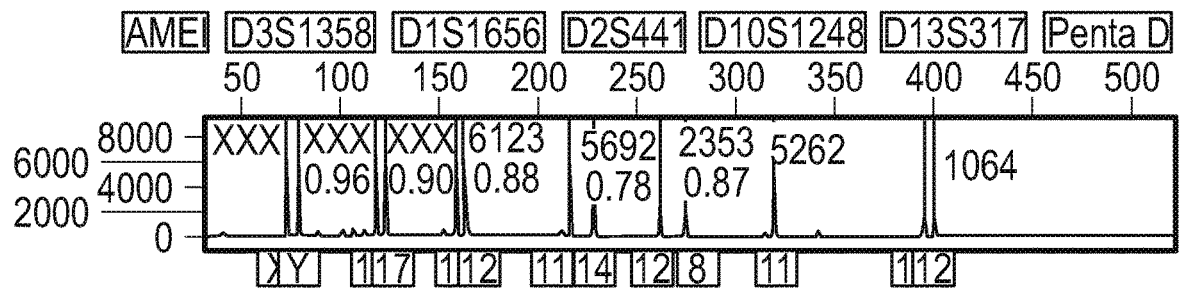
Figure 36:
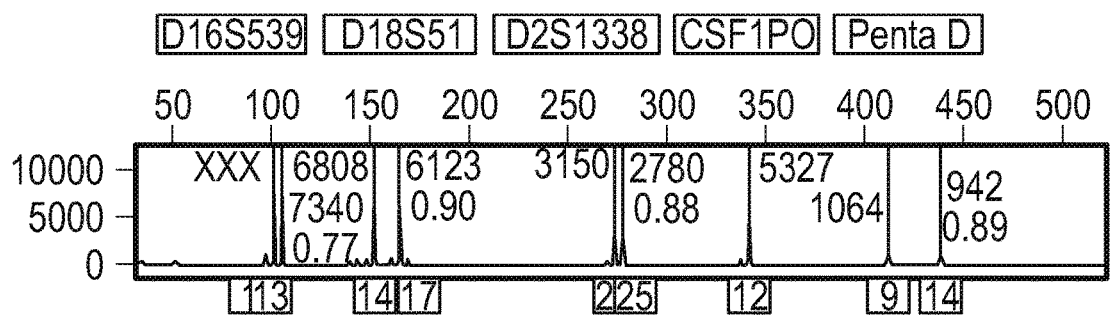
Figure 36:
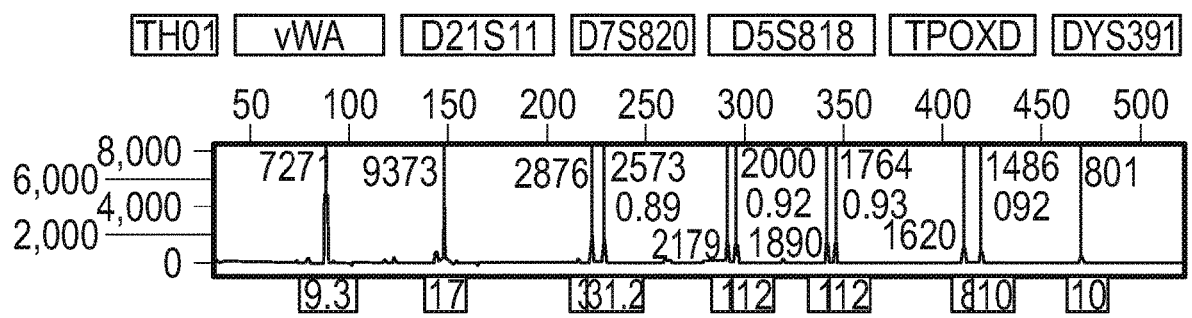
Figure 36:
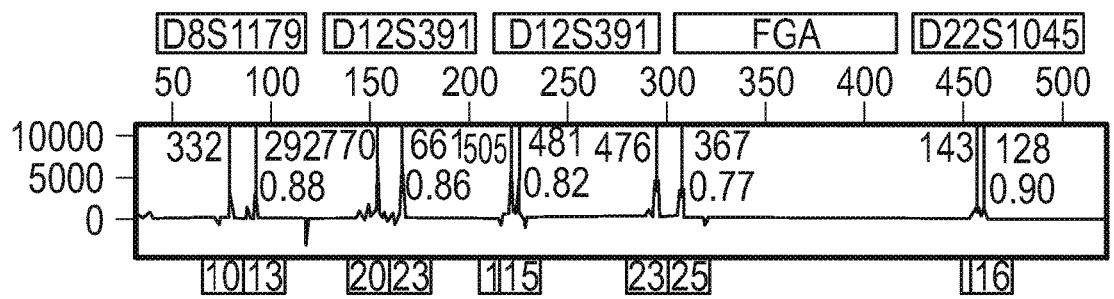

FIG. 36 illustrates STR electropherograms from two different individuals after DNA extraction using a PeT-PMMA microdevice, in accordance with at least one example of this disclosure. Gold electrodes are fabricated using a combination of polyester transparency sheets (PTS), double sided pressure sensitive adhesive (PSA) and commercially-purchased gold leaf. Electrodes consist of two key types. Type 1 electrodes are fabricated by adhering a PSA and PTS two layer construct onto an exposed sheet of gold leaf. The electrode design's outer shape is then ablated into this piece using a $CO_2$ laser. The gold electrode is attached to the bottom of the device making contact with the internal fluidics via an opening on the underside. A pogo pin then makes connection with the gold electrode from above through a hole in the microdevice. Type 2 electrodes were fabricated by $CO_2$ laser ablating the internal electrode features in to two layer constructs of PTS and double sided PSA layer. This two-layer piece was then laid onto a sheet of exposed gold leaf, forming three-layer construct of PTS, PSA and gold leaf, Into this, the outer shape of the electrode design was ablated using the $CO_2$ laser system. The Type 1 electrode is attached to the top of a microfluidic device, making contact with the internal fluidics via an opening in the top layer. A pogo pin then makes connection with the gold electrode through the exposed region of the electrode.

Until use the gold leaf on both electrode types is protected by a paper backing. The electrodes are designed to be incorporated in a microfluidic device using double-sided PSA, such that a voltage can be applied to the internal reagents, while keeping them insulated from outside contamination. This technique allows the user to stabilize and implement the gold leaf with relative ease. The method is also complementary to the print, cut and laminate fabrication methodologies, as it adopts the same design software (AutoCAD/Coreldraw), materials (PTS) and manufacture techniques ($CO_2$ laser). This has facilitated a holistic approach to fabricating devices in which the described electrodes are incorporated. This has, so far, been demonstrated with electrophoretic separation of DNA fragments. It is foreseen that the electrodes could be used for a wide range of electrophoretic separation applications, including clinical, forensic, and rural water analysis. In addition, the electrodes would potentially be applicable to electrochemistry applications. The main advantages of the materials described here are low cost, ease of manufacture and scalability.

In some examples, an electrode can include a gold leaf layer, an adhesive layer adhered to the gold leaf layer, and a transparent layer adhered to adhesive layer. In some examples, the transparent layer and the adhesive layer can each include comprise a window exposing the gold leaf layer.

System

The reagents for PCR (master mix, primers) and sample (template) are in separate chambers until PCR amplification is initiated, which involves housing the reagents in separate chambers, without the need for physical valves. This is accomplished by designing chambers with a volume capacity that is slightly larger than the reagent volume. Should the architecture require the use of valves to retain the reagents in their respective chambers, hydrophobic toner valves could also be used. Other types of valves, e.g., physical/mechanical valves that are opened (or closed) driven by some force (commonly pressure or vacuum) could also be used.

Of the chip-based PCR systems that have been described, the vast majority of these involve the application of heat to one side of the chip/chamber—this can lead to inefficient heating and cooling, but can also be addressed by slowing the temperature cycling to allow equilibrium at each temperature. With the need to carry out rapid temperature cycling, a Dual Integrated Peltier Spinning System (DIPSS) was used, which allow for heating from both sides of the chamber/chip simultaneously. A clamping system allows for contact between Peltier heaters and flat PCR chip.

Chip-based PCR systems often require manual alignment/adjustment. The present system has an optical alignment switch to allow for automated alignment of the PCR chip. This device allows for alignment of a circular PCR chip with 10° accuracy.

Peltiers tend to have temperature gradients that could affect accurate thermocycling of small volume liquids in micro-areas of the Peltier surface. The present inventor modified the dual Peltier system to reduce temperature gradients and maintain low thermal mass for rapid heating/cooling. This was accomplished by applying a thin layer of aluminum over the exposed surface of the Peltiers. The clamping system allows for effective contact between the Peltier heaters and flat PCR chip.

Chips with deeper chambers can be less efficient to heat using a dual heating system. To address this, the aspect ratio of the PCR chamber was modified to increase efficiency in heating and cooling by exploiting the thin nature of the Pe layer (about 100 μm) to achieve a PCR chamber with an increased exposed surface for contact with the heating elements. The length and width of the chamber were also increased to obtain the highest Peltier-exposed surface area relative to the volume in the chamber. In one embodiment, the aspect ratio (l, w, h) is approximately 6 mm, 5 mm, and 100 μm.

The DIPSS system was used with several STR-based PCR kits, including a custom-designed 6-plex, Powerplex Fusion, and a modified Powerplex 18D kit.

DNA Separation

After the separation sample has undergone heat, snap cool, the HMPAM polymer that was released by blister actuation at the beginning of the run, is spun into the COC separation channel at 2,500 rpm for 10 minutes. Polymer concentration was optimized at 1% of high molecular weight HMPAM to 4% low molecular weight HMPAM. As the polymer can become too viscous to allow proper centrifugal loading, this concentration was chosen to allow rapid centrifugal polymer filling (<10 minutes), but also allow the appropriate separation resolution (2 base resolution) for STR Human ID analysis. The sample, buffer, and sample waste chambers remain empty during channel filling to allow proper air displacement to occur to facilitate bubble-less loading. In order to complete the filling, the sample chamber is first filled at 2,500 rpm for 30 seconds, allowing contact between the DNA sample and the polymer in the separation channel. The sample chamber is designed in a way that allows any formation of air bubbles to displace at the top of the chamber, ultimately allowing fluid connection between COC channel inlet and gold leaf electrode. A valve is then opened to allow excess polymer to flow into a waste chamber, thereby, metering two chambers with additional polymer (2,500 rpm for 30 seconds, done at same time as sample loading). The addition of an excess waste chamber was due to the large volume of polymer (100 μL) required to generate enough pressure to load the channel through centrifugal means. It is important to get rid of such an excess, because any polymer connections (touching) with adjacent chambers will cause fluctuations in electrical connectivity that will ultimately result in an improper DNA separation. The aliquoted polymer after excess polymer removal is then used for sample waste and buffer chamber filling at 2,500 rpm for 30 seconds, allowing contact with the polymer located in the outlets of the separation channel. These chambers were designed to fill with a sufficient volume of polymer (>10 NL) to facilitate proper connection between electrode and polymer located in the separation channel. This filling process allows for appropriate DNA separation, as it eliminated any possible bubble formation, which can cause complications in electrical connection necessary for electrophoresis.

Figure 37A:
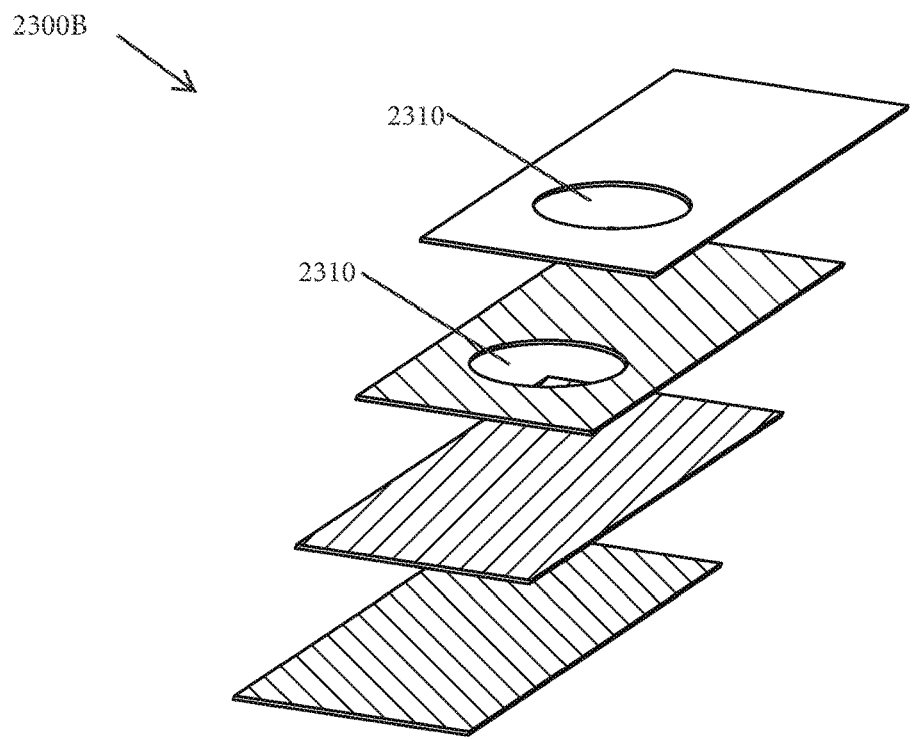
FIG. 37A illustrates a schematics of a gold leaf electrode, in accordance with at least one example of this disclosure.

FIG. 37A illustrates a schematics of a gold leaf electrode, in accordance with at least one example of this disclosure.

Figure 37B:
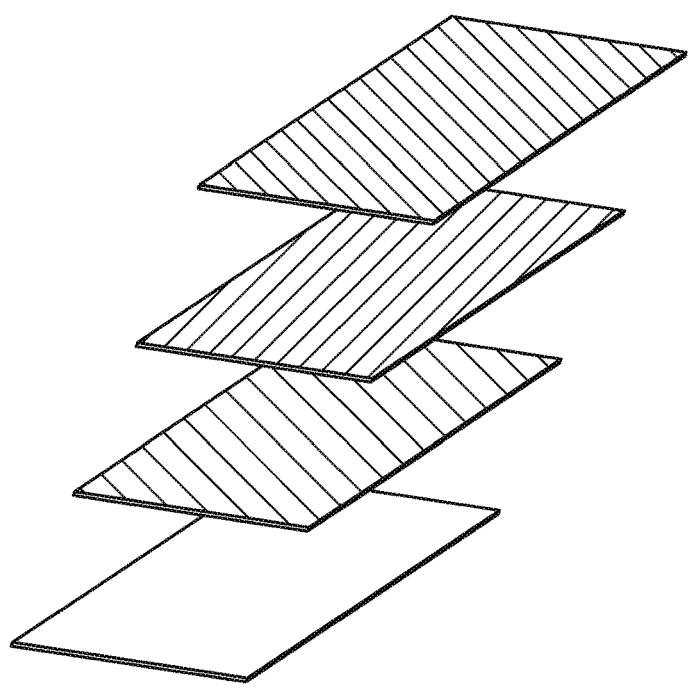
FIG. 37B illustrates a schematic of a gold leaf electrode, in accordance with at least one example of this disclosure.
Figure 37C:
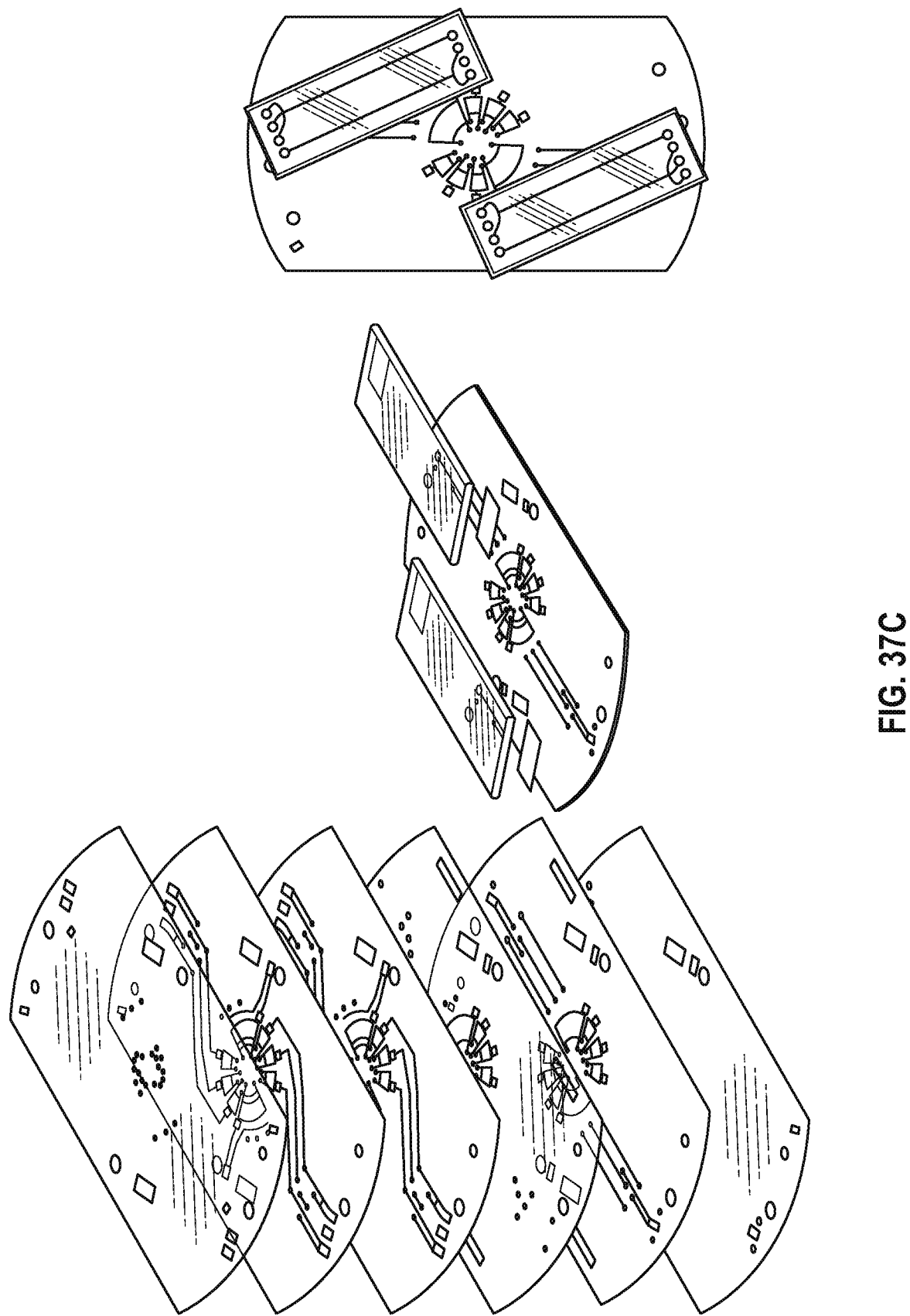
FIG. 37C illustrates a schematic showing components of an integrated separation device, in accordance with at least one example of this disclosure.

FIG. 37B illustrates a schematic of a gold leaf electrode, in accordance with at least one example of this disclosure. FIG. 37C illustrates a schematic showing components of an integrated separation device, in accordance with at least one example of this disclosure. FIGS. 37A-C. Detailed schematics of exemplary gold leaf electrode and separation device assemblies. A) A schematic illustrating the four layers and materials associated with type I electrodes. B) A schematic illustrating the four layers and materials associated with type II electrodes. C) A schematic detailing the fluidic frame work, individual layers and materials of an exemplary integrated separation device.

FIG. 37 displays a schematic demonstrating the various layers of a sole separation device that is comprised of polyethylene terephthalate, toner, a cyclic olefin copolymer separation chip, pressure sensitive adhesive, and gold leaf.

Figure 38A:
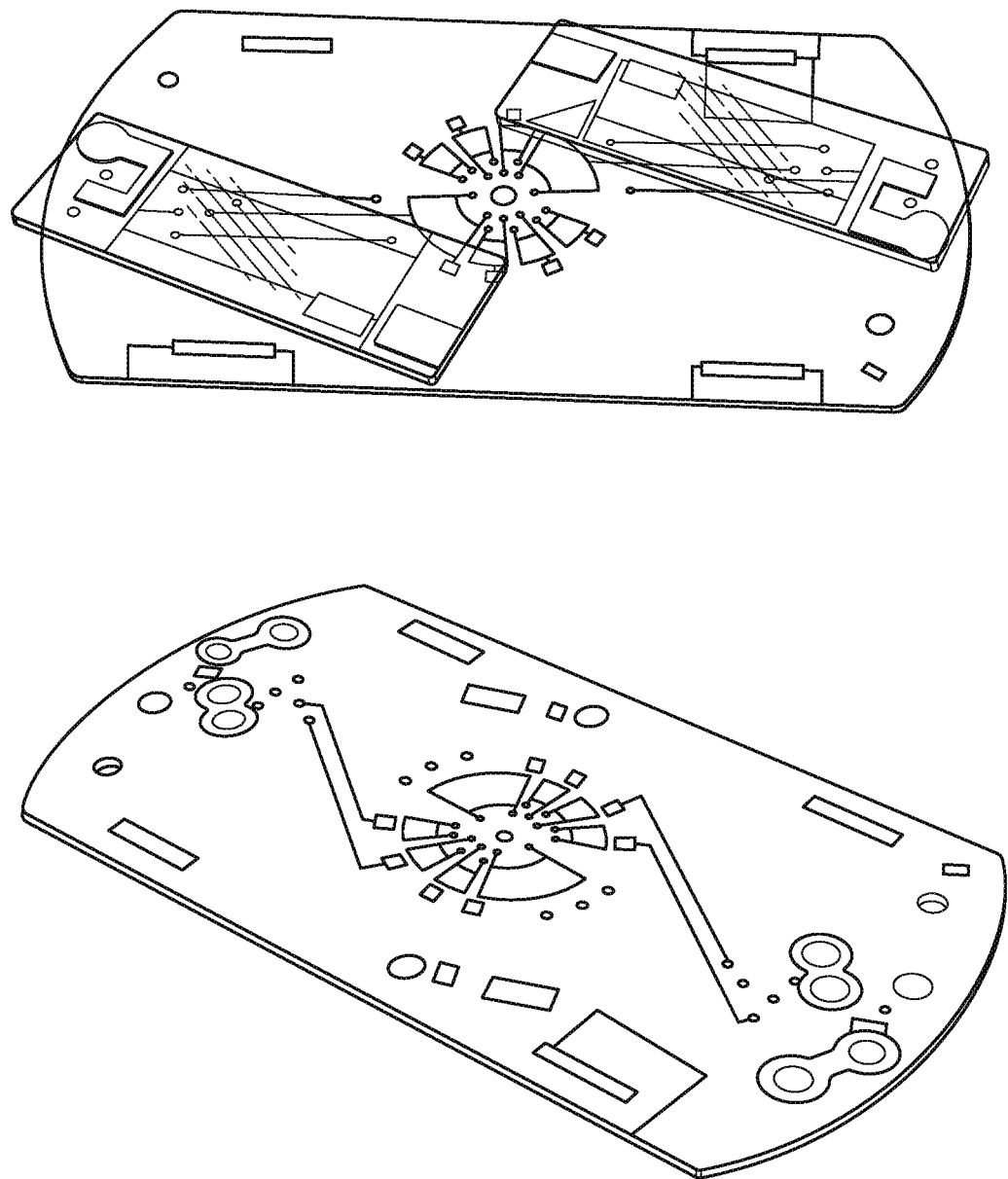
FIG. 38A illustrates perspective views of a front and backside of a fully integrated separation chip, in accordance with at least one example of this disclosure.
Figure 38B:
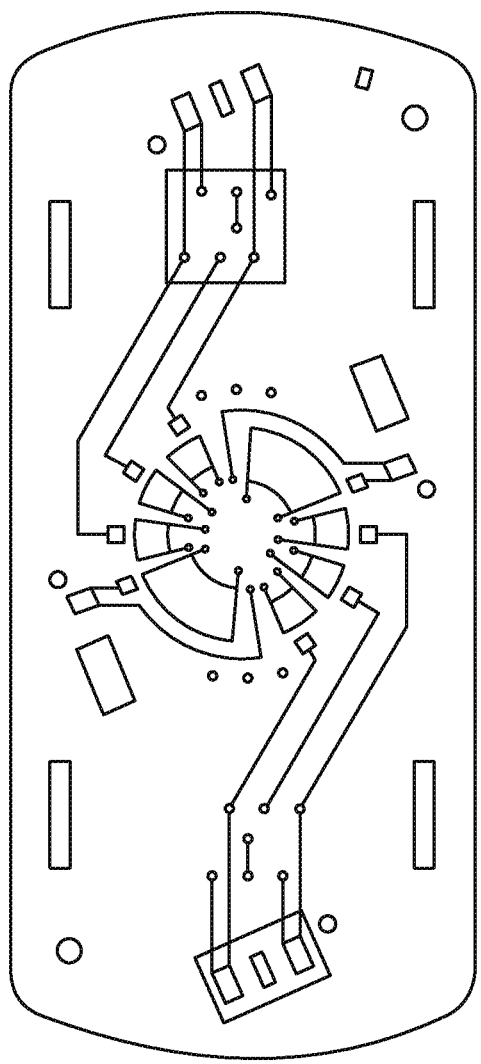
FIG. 38B illustrates a schematic showing an integrated device, in accordance with at least one example of this disclosure.

FIG. 38A illustrates perspective views of a front and backside of a fully integrated separation chip, in accordance with at least one example of this disclosure. FIG. 38B illustrates a schematic showing an integrated device, in accordance with at least one example of this disclosure. FIGS. 38A-B. Fully integrated microfluidic device. A) Images of the front and backside of a fully integrated separation chip that demonstrates one embodiment of placement of the gold leaf electrodes in relation to the microfluidic architecture. B) A detailed schematic illustrating another exemplary integrated device. FIG. 38 has real images showcasing the addition of the gold electrodes and architectural features utilized in our integrated device.

FIG. 39 illustrates an STR profile after separation on a fully integrated device at 6 different loci using a multicolored detection system. The strong profile identified all loci correctly, when compared to a separation performed on an ABI 310 instrument of the same sample, in accordance with at least one example of this disclosure.

Finally, FIG. 39 is a 6 loci STR profile that was obtained through the use of a hybrid separation device (materials listed above), where electrical current and connection was obtained through our custom gold leaf electrodes.

An aspect of an embodiment of the present invention provides, but not limited thereto, two parts: an on-chip sample lysis and an on-chip DNA extraction. Both of these processes are performed on a Pe-toner (PeT) microfluidic device composed of commercial-off-the-shelf (COTS) products and fabricated using 'print, cut, laminate' technology. Briefly, commercial printer toner is printed on both sides of Pe sheets which acts as the adhesive between each layer of the device. The architecture of each layer is then cut with a $CO_2$ laser before aligning the layers together and thermally laminating the layers to melt the toner and bond the layers of Pe for an enclosed system.

On-Chip Sample Lysis

Sample lysis exploits the biological properties of cells in the presence of chaotropic solutions. Each device is 4 layers and has a square cutout in the top of the chamber, which accommodates the placement of a swab cutting that is to be tested. A biocompatible adhesive sealed the chamber prior to filling with a chaotropic lysis buffer. Heating the chip on a heat block set at 56° C. allows the release of nuclear material. Initial experiments looked at parallel processing of a buccal swab cuttings: one placed in a chip for on-chip lysis and the other placed in a conventional tube lysis. Both samples, after the lysis step completed, were brought through the same DNA processing steps (e.g., DNA extraction, quantitation, amplification, and detection) together, and, upon examining the STR profiles obtained from both samples, there were no differences in the STR profiles. This on-chip assay is therefore able to achieve successful on-chip lysis with a 66% reduction of incubation time and less than 8% of the original volume compared to conventional techniques.

Thus, in one embodiment, a device and method which allows for sample lysis on a Pe microfluidic device is provided.

On-Chip DNA Extraction

Dynamic solid-phase extraction (dSPE), or the purification of DNA by moving the magnetic silica particles through a static solution, was chosen for the extraction protocol, as it circumvents the reproducible packing issues of packed silica extractions. The extraction protocol from a previously described PeT dSPE device, however, since the previous dSPE device required multiple manual pipetting and mixing steps, the device was moved to a centrifugal platform. Fluid, therefore, could be pushed through the device from the center towards the outer edges by simply spinning the device. There are two embodiments of this device that were developed based on the following dSPE protocol: (i.) mixing the particles and DNA-containing sample in a chaotropic solution to bind the DNA to beads, (ii.) washing the beads with an alcohol solution to solubilize any bound proteins and wash away contaminants, (iii.) wash away residual alcohol with a low-salt buffer, (iv.) release the DNA from the particles in a low-salt buffer, and (v.) transfer the purified DNA to a separate collection chamber. In order to take the sample out of the device, a polymer sleeve, covering the top of a recovery chamber containing purified DNA, is punctured is extracted from the device using a syringe. The first embodiment demonstrate successful DNA extraction, using a combination of passive and mechanical valves. The second embodiment improves the dSPE microfluidic design automation with the conversion of all mechanical valves to passive valves.

Thus, in one embodiment, a device and method which allows for centrifugally-driven DNA extraction in microfluidic device having Pe and printer toner is provided.

a) Fluidic Control

Successful extractions require sequential addition of the reagents mentioned previously, which could only be achieved with fluidic valving. To keep a system fully automated, yet simple enough for portability, it was important to use passive valving wherever possible. Ouyang et al. identified the usefulness of 'toner valves', or patches of printer toner on the top and bottom of a channel that could produce a large surface tension to prevent the passing of a solution until the surface tension was overcome by centrifugal force. Although these valves were useful for holding a wash buffer and the elution buffer until needed in the extraction, they are not compatible with alcohol solutions. Furthermore, these 'toner valves' are only a one-time actuated valve which cannot keep waste solutions from entering the DNA collection chamber only meant for the purified DNA solution.

A combination of resistive elements were used to keep the alcohol from entering the main DNA chamber during the initial binding of DNA and the silica particles. First, the absence of air vents between the main chamber and the chambers holding the alcohol solution produced a backpressure when the main DNA chamber was filled. Furthermore, the chambers holding the alcohol were designed to hold an extra 0.5 µL of volume which allowed air to separate the alcohol from leaving the chamber. Together, these kept the alcohol in place and, only when the device spun, was air displaced, allowing the alcohol to flow freely through the device.

Two valves were used to steer solutions either to the waste chamber or the DNA collection chamber, both of which connect below the main DNA chamber: a siphon valve and a 'tape valve'. A 'tape valve', similar to one developed by Lounsbury et al. on a poly(methyl methacrylate) (PMMA) microdevice, was used for controlled access to the DNA collection chamber[6]. The 'tape valve' was fabricated in PeT in two layers. The bottom layers were Pe material to make a valve seat and defined a physical barrier separating the incoming channel from the one coming out of the valve. The second layer was a double-sided adhesive that could stick to a piece of Scotch® tape which enclosed the device but also add height of the valve to lower the resistance for a solution to pass the physical barrier separating the channels.

One embodiment of this dSPE microfluidic device, having two 'tape valves', was used to separate both the waste chamber and the DNA chamber as well as the DNA collection chamber from the main DNA chamber. At the beginning of an extraction, the 'tape valve' between the DNA collection chamber and the main chamber would be closed while the 'tape valve' to the waste chamber was in the open position. This would allow all solutions to be driven down to the waste chambers. Once the washing steps were completed and the elution step was to be next, a blunt object was used to close the 'tape valve' that separated the waste chamber from the main DNA chamber by applying pressure to the adhesive that sits directly above the physical barrier of the valve. At this point, both 'tape valves' are closed, only allowing fluids to come to the main DNA chamber and no further. The elution solution, once released from the toner valve, comes down to the main chamber and is ready to mix with the magnetic particles to release the DNA. In order to transfer the elution solution to the DNA collection chamber and not to the waste, the width of the physical barriers of the 'tape valves' had to be different. The physical barrier separating the incoming from the outgoing channel was thinner for the 'tape valve' directing fluid to the DNA collection chamber, therefore, this 'tape valve' had a lower burst pressure and would be forced open first.

The manual closing of the tape valve compromised the automation of the device, therefore, improvements in the valving were done in a second embodiment. One of these improvements was to replace the 'tape valve' between the waste and the main DNA chamber with a siphon valve. A siphon valve was used to allow access to the waste reagents after initial binding, during the alcohol wash, and to eliminate residual alcohol, yet produce enough resistance such that when waste chambers would be full after all washing steps were completed, it would prevent the elution buffer from going to the waste. This allowed the elution buffer to be kept in the main DNA chamber. The extraction began with the 'tape valve' in the closed position, forcing all solutions to pass through to the waste chambers. Only when the device was spun in excess of the valve's burst pressure of 550 revolutions per minute (RPM) was the valve forced open. After the DNA was released from the particles, the device was spun at a high acceleration to 1000 RPM so the 'tape valve' was forced open before the solution could go through the siphon valve.

Thus, one embodiment provides for a 'tape valve' structure fabricated on a PeT microfluidic device; as well as first use of passive valving techniques to contain alcohol solutions on a PeT microfluidic device.

b) Magnetic Induced Mixing

Unlike all other extraction centrifugal platforms, the magnetic field remained static and the sample disc containing the dSPE reagents were moved bidirectionally ~43°. Two magnets were placed such that when the sample disc moved 43° counter-clockwise, the beads would be brought to the upper left corner of the chamber. The disc would then be brought 43° clockwise and come in contact with a second magnet that would bring the particles to the lower right corner of the chamber. The disc would then repeat this cycle, sweeping the beads to opposing corners of the chamber for full mixing (shown in FIG. 6). Validation of this mixing strategy was confirmed using fluorospectrometry for quantitating the presence of DNA followed by successful amplification of β-globin.

An aspect of various embodiments provides for magnetic mixing that is done with a microfluidic device moving around stationary magnets.

c) STR Amplification

DNA collected from a centrifugally-driven DNA extraction microdevice produced full STR profiles that were in 100% agreement with conventional benchtop processes. The profile quality (e.g., peak height and peak balance) was compared and there were no significant differences. Therefore, the PeT dSPE device can be used for reliable DNA extraction of forensically-relevant samples. The second embodiment design workflow was also validated with STR profiles from blood and buccal swab samples.

An aspect of various embodiments may provide a multiplexed amplification demonstrated from an automated DNA extraction device, and DNA taken from a centrifugally-driven DNA extraction microfluidic device that is compatible with multiplexed amplification.

Once the PCR amplification is completed, the product volume is spun down to another chamber, where the internal lane standard and water, are then subsequently added. The sandwich Peltier system then completely covers the chamber and heats to 95° C. for 1 minute. The Peltiers are then opened and the disc is spun at 1,000 rpm for 10 seconds. This "degassing" step was included to remove bubbles that are a common occurrence in centrifugal microfluidic processes, especially when heating is included in the process. By eliminating bubbles, there is no air expansion, which decreases unwanted fluid movement as well as sample evaporation. The chamber is then heated to 95° C. for 3 minutes, ultimately denaturing the DNA, and then is rapidly cooled to 10° C. to keep single stranded DNA from reannealing. The cooling rate of the Peltier system, which is dictated by our optimized PID parameters and code, is fast enough to perform a successful heat, snap cool, which is paramount for downstream DNA electrophoresis to occur properly.

FIG. 40 illustrates an electropherograms demonstrating the similarity between the heat, snap cool method versus the traditional (literature) method, in accordance with at least one example of this disclosure.

FIG. 40 demonstrates an electrophoretic separation with a sample that was heat, snap cooled (HSC) in tube, in the traditional manner, with a commercial thermocycler. The electropherogram below, displays an electrophoretic separation on a sample that was heat, snap cooled with the method described above using a Peltier system. The agreement between the two electropherograms, as far as the peak spacing, shows the ability to obtain a denatured DNA sample from our purposed method in the same manner the traditional way would offer.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions may or may not be provided on the aforementioned figures, the device may constitute various sizes, dimensions, contours, rigidity, shapes, flexibility and materials as it pertains to the components or portions of components of the device, and therefore may be varied and utilized as desired or required.

It should be appreciated that the device and related components discussed herein may take on all shapes along the entire continual geometric spectrum of manipulation of x, y and z planes to provide and meet the structural demands and operational requirements. Moreover, locations and alignments of the various components may vary as desired or required.

Notes and Examples

In Example 1, a centrifugal microfluidic device can include subject matter (such as a device or apparatus) configured to prepare a sample for nucleic acid analysis, the centrifugal microfluidic device comprising: a body formed from of a plurality of layers; an extraction portion of the body comprising: a first reagent storage chamber; and a liberation chamber; a reaction portion of the body comprising: a mixing chamber; and a second reagent chamber connected to the mixing chamber; a heat and snap-cool portion of the body; and a separation portion of the body comprising: a polymer loading reservoir and one or more polymer channels; and a separation channel connected to the one or more polymer channels and connected to an electrode.

In Example 2, the device of Example 1 can optionally be configured such that the liberation chamber is configured to receive a sample and configured to receive a first reagent from the first reagent storage chamber.

In Example 3, the device of any one or any combination of Examples 1-2 can optionally be configured such that the mixing chamber is configured to mix the first fluid with a specific volume of a second reagent to create a second fluid.

In Example 4, the device of any one or any combination of Examples 1-3 can optionally be configured such that the heat and snap-cool portion is configured to mix the second fluid with a third reagent to create a third fluid, and configured to heat and snap-cool the third fluid.

In Example 5, the device of any one or any combination of Examples 1-4 can optionally be configured such that the separation channel is configured to conduct electrophoretic separation on a mixture of the polymer and the third fluid to create a fourth fluid.

In Example 6, the device of any one or any combination of Examples 1-5 can optionally be configured such that at least one of the plurality of layers is comprised of poly methyl methacrylate In Example 7, the device of any one or any combination of Examples 1-6 can optionally be configured such that the plurality of layers are adhered by a heat sensitive adhesive.

In Example 8, the device of any one or any combination of Examples 1-7 can optionally be configured such that the electrode comprises: a gold leaf layer; an adhesive layer adhered to the gold leaf layer; and a transparent layer adhered to adhesive layer.

In Example 9, a method of preparing nucleic acid for analysis using a centrifugal microfluidic device can include subject matter (such as a method) comprising: moving a first reagent from a first reagent chamber to an extraction chamber using centrifugal force; extracting a first fluid from a sample cells or nucleic acid by heating the sample in the extraction chamber; and moving the first fluid to an aliquot chamber using centrifugal force; moving a first fluid to a mixing chamber using centrifugal force; introducing a second reagent into the mixing chamber through a metering chamber using centrifugal force thereby providing a third fluid; moving the third fluid to a reaction chamber using centrifugal force; degassing the third fluid using centrifugal force; moving the third fluid to a snap-cool chamber using centrifugal force; moving a third reagent using centrifugal force to the snap-cool chamber to form a fourth fluid; loading a polymer into a polymer chamber using centrifugal force; and mixing the fourth fluid with the polymer to create a fifth fluid.

In Example 10, the method of Example 9 can optionally be configured to further comprise: heating and cooling the third fluid cyclically.

In Example 11, the method of any one or any combination of Examples 9-10 can optionally be configured to further comprise: snap-cooling the third fluid.

In Example 12, the method of any one or any combination of Examples 9-11 can optionally be configured to further comprise: degassing the fourth fluid using centrifugal force; and moving the fourth fluid to a separation chamber using centrifugal force.

In Example 13, the method of any one or any combination of Examples 9-12 can optionally be configured to further comprise: subjecting the fifth fluid to electrophoretic separation.

In Example 14, an electrode can include subject matter (such as a device or apparatus) comprising: a gold leaf layer; an adhesive layer adhered to the gold leaf layer; and a transparent layer adhered to adhesive layer.

In Example 15, the device of Example 14 can optionally be configured such that the transparent layer and the adhesive layer each comprise a window exposing the gold leaf layer.

In Example 16, a chip configured for a nucleic acid amplification process can include subject matter (such as a device or apparatus) comprising: a vent configured to vent gas; a mixing chamber configured to mix and degas a fluid; a reaction chamber comprising: a first side connected to the vent by a vent channel; and a second side connected to the mixing chamber by a chamber channel; and a plurality of reagent chambers connected to the mixing chamber by a plurality of reagent channels, the reagent chambers having a volume that is larger than a volume of reagents.

In Example 17, the device of Example 16 can optionally be configured such that the reaction chip is comprised of polyester.

In Example 18, the device of any one or any combination of Examples 16-17 can optionally be configured to further comprise a hydrophobic toner valve connected to one or more of the plurality of reagent channels and the mixing chamber.

In Example 19, the device of any one or any combination of Examples 16-18 can optionally be configured such that the chip has a shape of an irregular hexagonal prism.

In Example 20, the device of any one or any combination of Examples 16-19 can optionally be configured to further comprise: a first thickness of the chip; and a reaction chamber thickness; wherein the first thickness of the chip is larger than the reaction chamber thickness.

In Example 21, the device of any one or any combination of Examples 16-20 can optionally be configured to further comprise: a reaction chamber volume, wherein a reaction chamber thickness to reaction chamber volume ratio is between about 1 and about 5 percent.

In Example 22, the device of any one or any combination of Examples 16-21 can optionally be configured such that the reaction chamber thickness to reaction chamber volume ratio is about 3 percent.

In Example 23, a reaction thermocycling device can include subject matter (such as a device or apparatus) comprising: a rotating platform configured to controllably spin a chip, the rotating platform comprising a first side and a second side opposing the first side; a first thermoelectric heat pump disposed adjacent the first side of the rotating platform; a second thermoelectric heat pump disposed adjacent the second side of the rotating platform; and a first fan adjacent to the first thermoelectric heat pump, the first fan configured to deliver a first flow of fluid to the rotating platform.

In Example 24, the device of Example 23 can optionally be configured to further comprise a second fan adjacent to the second thermoelectric heat pump, the second fan configured to deliver a second flow of fluid to the rotating platform.

In Example 25, the device of any one or any combination of Examples 23-24 can optionally be configured to further comprise a clamp connected to the first thermoelectric heat pump and the second thermoelectric heat pump, the clamp configured to position the first thermoelectric heat pump in contact with a first side of a chip connected to the rotating platform and configured to position the second thermoelectric heat pump in contact with a second side of the chip connected to the rotating platform.

In Example 26, the device of any one or any combination of Examples 23-25 can optionally be configured to further comprise an optical alignment switch connected to the rotating platform, the optical alignment switch configured to align a chip on the rotating platform.

In Example 27, the device of any one or any combination of Examples 23-26 can optionally be configured such that the first thermoelectric heat pump comprises an exposed metallic surface facing the rotating platform, the exposed metallic surface comprising a small thermal mass relative to the chip and the first thermoelectric heat pump.

In Example 28, a centrifugal microfluidic device configured for separation of nucleic acids can include subject matter (such as a device or apparatus) comprising: a top layer comprised of cyclic olefin copolymer, the top layer including a first top layer side and a second top layer side opposing the first top layer side; a middle layer comprising: a first middle layer side configured to mate to the second top layer side; and a second middle layer side opposing the first middle layer side; and a bottom layer comprised of cyclic olefin copolymer, the bottom layer comprising: a first bottom layer side configured to mate to the second middle layer side; and a second bottom layer side opposing the first bottom layer side.

In Example 29, the device of Example 28 can optionally be configured such that the middle layer is comprised of a pressure sensitive adhesive.

In Example 30, the device of Example 28 can optionally be configured such that the middle layer is comprised of toner-printed polyethylene terephthalate.

In Example 31, the device of any one of Examples 28-30 can optionally be configured such that the first middle layer side and the second middle layer side are each plasma oxidized.

In Example 32, the device of any one of Examples 28-31 can optionally be configured such that the first middle layer side and the second middle layer side are each plasma oxidized for about five to about ten minutes.

In Example 33, the device of any one or of Examples 28-32 can optionally be configured to further comprise: an injection molded separation device mounted to one of the top layer, the middle layer, and the bottom layer.

In Example 34, the device of any one of Examples 28-33 can optionally be configured such that the injection molded separation device is secured using an adhesive.

In Example 35, the device of any one of Examples 28-34 can optionally be configured such that the middle layer comprises: a sample reservoir disposed near a center of the middle layer; a plurality of polymer reservoirs disposed near a periphery of the middle layer; a separation channel extending radially outward from the sample reservoir; and a plurality of polymer reservoir channels, each connected to the separation channel and extending radially beyond the plurality of polymer reservoirs and each turning inward to connect to one of the plurality of polymer reservoirs.

In Example 36, the device of any one of Examples 28-35 can optionally be configured such that the separation channel extends circumferentially and radially from the sample reservoir to the periphery of the middle layer and then extends substantially circumferentially before connecting to the plurality of polymer reservoir channels.

In Example 37, the device of any one of Examples 28-36 can optionally be configured such that the separation channel extends radially inward before connecting to the plurality of polymer reservoir channels.

In Example 38, the device of any one of Examples 28-37 can optionally be configured such that the middle layer comprises: a plurality of sample reservoirs including the sample reservoir, wherein each of the plurality of sample reservoirs is disposed near a center of the middle layer; and a plurality of separation channels including the separation channel, wherein each of the plurality of separation channels extends radially outward from the sample reservoir.

In Example 39, a method of creating a centrifugal microfluidic device configured for separation of nucleic acids can include subject matter (such as a method) comprising: forming a top layer; forming a middle layer; ablating channels and chambers into the middle layer; surrounding the middle layer with non-bonding layers; re-profiling ridges adjacent the channels and the chambers after ablating the channels and chambers by introducing the middle layer surrounded by the non-bonding layers into a bonding laminator; forming a bottom layer; and bonding the top layer and the bottom layer to the middle layer.

In Example 40, the method of Example 39 can optionally be configured such that the top layer and the bottom layer are comprised of cyclic olefin copolymer.

In Example 41, the method of any one or any combination of Examples 39-40 can optionally be configured such that the middle layer is comprised of a toner-printed polyethylene terephthalate.

In Example 42, the method of any one or any combination of Examples 39-41 can optionally be configured to further comprise: plasma oxidizing a first side of the middle layer prior to boding one of the top layer and the bottom layer to the middle layer.

In Example 43, the method of any one or any combination of Examples 39-42 can optionally be configured to further comprise: plasma oxidizing a second side of the middle layer prior to boding one of the top layer and the bottom layer to the middle layer.

In Example 44, the method of any one or any combination of Examples 39-43 can optionally be configured such that the ablating process cuts entirely through the middle layer to create the channels and chambers.

In Example 45, a chip configured to isolate nucleic acid through a centrifugal process can include subject matter (such as a device or apparatus) comprising: a main vent, a recovery vent, a liberation vent, and a plurality of storage vents, each configured to vent gas; a first valve and a second valve; a reagent chamber connected the plurality of storage vents and connected to the first valve; a liberation chamber comprising: a first liberation chamber end connected to the first valve and connected to a liberation vent; and a second liberation chamber end connected to the second valve, wherein the second valve is connected to the recovery vent; and a recovery chamber comprising: a first recovery side connected to the main vent; and a second recovery side connected to the second valve.

In Example 46, the device of Example 45 can optionally be configured such that the chip is formed of a plurality of polyester layers.

In Example 47, the device of any one of Examples 45-46 can optionally be configured such that the first valve and the second valve are one of laser-actuated valves and hydrophobic valves.

In Example 48, the device of any one of Examples 45-47 can optionally be configured such that the liberation chamber is configured receive a sample and configured to mix a reagent with the sample.

In Example 49, the device of any one of Examples 45-48 can optionally be configured to further comprise: a liberation vent channel connected to the first liberation chamber end and connected to the liberation vent and forming a vent connection between the liberation vent channel and the first liberation chamber end; and a liberation first valve channel connected to the first valve and connected to the first liberation chamber end and forming a valve connection between the liberation first valve channel and the first liberation chamber end.

In Example 50, the device of any one of Examples 45-49 can optionally be configured such that the vent connection and the valve connection connect to the liberation chamber adjacently.

In Example 51, the device of any one of Examples 45-50 can optionally be configured to further comprise: a transition between the vent connection and the valve connection comprising a V shape In Example 52, a multiplexed device comprising a plurality chips can include the device of any one of Examples 45-51, such that the plurality of chips are circumferentially distributed around the chip such that a centrifugal process can be performed on each chip simultaneously.

In Example 53, a method of extracting a product using a chip can include subject matter (such as a method) comprising: pre-loading a reagent into a storage chamber of the chip; opening a liberation chamber of the chip; loading a swab into the liberation chamber; sealing the liberation chamber; opening a storage valve of the chip; spinning the chip to release the reagent from the storage chamber into the liberation chamber; aligning the chip to a heater; heating the chip to liberate the product; opening a recovery valve; and spinning the chip to separate product from the swab.

In Example 54, the method of Example 53 can optionally be configured such that the swab is one of a bristle swab, a foam swab, and a cotton swab.

In Example 55, the method of any one or any combination of Examples 53-54 can optionally be configured such that the chip is heated to about 75 degrees Celsius for about 2 minutes and about 95 degrees Celsius for about 30 seconds.

In Example 56, A method to extract, amplify and separate nucleic acid in a microfluidic device having a plurality of chambers and channels can include subject matter (such as a method) comprising: a) introducing a sample having nucleic acid to a first chamber of the microfluidic device and subjecting the cells in the first chamber to conditions that lyse the cells; b) subjecting the first chamber to centrifugal force, thereby allowing the lysate or a portion thereof having nucleic acid to be distributed to a second chamber through a first channel in the microfluidic device; c) combining the lysate or the portion thereof and reagents for amplification of the nucleic acid, thereby providing a second mixture; d) subjecting the second chamber to centrifugal force, thereby allowing gas to be expelled from the second mixture; e) subjecting the second mixture in the second chamber to cyclic amplification, thereby providing amplified nucleic acid; f) subjecting the second mixture having the amplified nucleic acid to centrifugal force, thereby allowing the amplified nucleic acid to be distributed to a third chamber in the microfluidic device through a second channel, which third chamber reduces the temperature of the amplified nucleic acid to provide denatured nucleic acid; g) subjecting the third chamber to centrifugal force, thereby allowing gas to be expelled from the second mixture; h) combining the amplified nucleic acid in the third chamber with a polymer, thereby providing a fourth mixture; and i) introducing the fourth mixture into a separation channel using centrifugal force.

In Example 57, the method of Example 56 can optionally be configured such that the conditions in a) are exposure to enzyme, a chaotropic solution or heat.

In Example 58, the method of any one or any combination of Examples 56-57 can optionally be configured such that the reagents for amplification prior to combining are in two or more separate storage chambers In Example 59, the method of any one or any combination of Examples 56-58 can optionally be configured such that one or more valves separate the chambers.

In Example 60, the method of any one or any combination of Examples 56-59 can optionally be configured such that a Peltier system is employed for heating in the cyclic amplification.

In Example 61, the method of any one or any combination of Examples 56-60 can optionally be configured such that the second chamber is formed of Pe toner.

In Example 62, the method of any one or any combination of Examples 56-61 can optionally be configured such that the separation channel comprises cyclic olefin copolymer, polyester, pressure sensitive adhesive, toner, or any combination thereof.

In Example 63, the method of any one or any combination of Examples 56-62 can optionally be configured such that the microfluidic device comprises a gold electrode.

In Example 64, the method of any one or any combination of Examples 56-63 can optionally be configured such that the microfluidic device is formed of polytetrafluoroethylene (PFTE) hydrophobic membrane filter, gold leaf, polyethyl terephthalate, toner, polymethylmethacrylate (PMMA), heat sensitive adhesive, pressure sensitive adhesive, or any combination thereof.

In Example 65, the method of any one or any combination of Examples 56-64 can optionally be configured such that the polymer comprises hydrophobically modified poly(acrylamide) HMPAM.

In Example 66, the method of any one or any combination of Examples 56-65 can optionally be configured such that the separation channel comprises gold leaf.

In Example 67, the method of any one or any combination of Examples 56-66 can optionally be configured such that the first chamber further comprises magnetic beads.

In Example 68, the method of any one or any combination of Examples 56-67 can optionally be configured such that one or more of the valves are passive valves.

Additional Notes and Examples

In Example 69, A method to extract, amplify and separate nucleic acid in a microfluidic device having a plurality of chambers and channels can include subject matter (such as a method) comprising: a) introducing a sample having nucleic acid to a first chamber of the microfluidic device and subjecting the cells in the first chamber to conditions that lyse the cells; b) subjecting the first chamber to centrifugal force, thereby allowing the lysate or a portion thereof having nucleic acid to be distributed to a second chamber through a first channel in the microfluidic device; c) combining the lysate or the portion thereof and reagents for amplification of the nucleic acid, thereby providing a second mixture; d) subjecting the second chamber to centrifugal force, thereby allowing gas to be expelled from the second mixture; e) subjecting the second mixture in the second chamber to cyclic amplification, thereby providing amplified nucleic acid; f) subjecting the second mixture having the amplified nucleic acid to centrifugal force, thereby allowing the amplified nucleic acid to be distributed to a third chamber in the microfluidic device through a second channel, which third chamber reduces the temperature of the amplified nucleic acid to provide denatured nucleic acid; g) subjecting the third chamber to centrifugal force, thereby allowing gas to be expelled from the second mixture; h) combining the amplified nucleic acid in the third chamber with a polymer, thereby providing a fourth mixture; and i) introducing the fourth mixture into a separation channel using centrifugal force.

In Example 70, the method of Example 69 can optionally be configured such that the conditions in a) are exposure to enzyme, a chaotropic solution or heat.

In Example 71, the method of any one or any combination of Examples 69-70 can optionally be configured such that the reagents for amplification prior to combining are in two or more separate storage chambers In Example 72, the method of any one or any combination of Examples 69-71 can optionally be configured such that one or more valves separate the chambers.

In Example 73, the method of any one or any combination of Examples 69-72 can optionally be configured such that a Peltier system is employed for heating in the cyclic amplification.

In Example 74, the method of any one or any combination of Examples 69-73 can optionally be configured such that the second chamber is formed of Pe toner.

In Example 75, the method of any one or any combination of Examples 69-74 can optionally be configured such that the separation channel comprises cyclic olefin copolymer, polyester, pressure sensitive adhesive, toner, or any combination thereof.

In Example 76, the method of any one or any combination of Examples 69-75 can optionally be configured such that the microfluidic device comprises a gold electrode.

In Example 77, the method of any one or any combination of Examples 69-76 can optionally be configured such that the microfluidic device is formed of polytetrafluoroethylene (PFTE) hydrophobic membrane filter, gold leaf, polyethyl terephthalate, toner, polymethylmethacrylate (PMMA), heat sensitive adhesive, pressure sensitive adhesive, or any combination thereof.

In Example 78, the method of any one or any combination of Examples 69-77 can optionally be configured such that the polymer comprises hydrophobically modified poly(acrylamide) HMPAM.

In Example 79, the method of any one or any combination of Examples 69-78 can optionally be configured such that the separation channel comprises gold leaf.

In Example 80, the method of any one or any combination of Examples 69-79 can optionally be configured such that the first chamber further comprises magnetic beads.

In Example 81, the method of any one or any combination of Examples 69-80 can optionally be configured such that one or more of the valves are passive valves.

In Example 82, a reaction thermocycling device can include subject matter (such as a device or apparatus) comprising: a rotating platform configured to controllably spin a chip, the rotating platform comprising a first side and a second side opposing the first side; a first thermoelectric heat pump disposed adjacent the first side of the rotating platform; a second thermoelectric heat pump disposed adjacent the second side of the rotating platform; and a first fan adjacent to the first thermoelectric heat pump, the first fan configured to deliver a first flow of fluid to the rotating platform.

In Example 83, the device of Example 82 can optionally be configured to further comprise a second fan adjacent to the second thermoelectric heat pump, the second fan configured to deliver a second flow of fluid to the rotating platform.

In Example 84, the device of any one or any combination of Examples 82-83 can optionally be configured to further comprise a clamp connected to the first thermoelectric heat pump and the second thermoelectric heat pump, the clamp configured to position the first thermoelectric heat pump in contact with a first side of a chip connected to the rotating platform and configured to position the second thermoelectric heat pump in contact with a second side of the chip connected to the rotating platform.

In Example 85, the device of any one or any combination of Examples 82-84 can optionally be configured to further comprise an optical alignment switch connected to the rotating platform, the optical alignment switch configured to align a chip on the rotating platform.

In Example 86, the device of any one or any combination of Examples 82-85 can optionally be configured such that the first thermoelectric heat pump comprises an exposed metallic surface facing the rotating platform, the exposed metallic surface comprising a small thermal mass relative to the chip and the first thermoelectric heat pump.

In Example 87, an electrode can include subject matter (such as a device or apparatus) comprising: a gold leaf layer; an adhesive layer adhered to the gold leaf layer; and a transparent layer adhered to adhesive layer.

In Example 88, the device of Example 87 can optionally be configured such that the transparent layer and the adhesive layer each comprise a window exposing the gold leaf layer.

REFERENCES

International Patent Application No. PCT/US2013/074152 entitled "FREQUENCY-BASED FILTERING OF MECHANICAL ACTUATION USING FLUIDIC DEVICE," filed Dec. 10, 2013.

U.S. patent application Ser. No. 13/849,691 entitled "Electrostatic Actuation for Management of Flow in Micro Total Analysis Systems and Related Method Thereof," filed Mar. 25, 2013.

U.S. patent application Ser. No. 13/294,908 entitled "Electrostatic Actuation for Management of Flow in Micro-Total Analysis Systems (u-TAS) and Related Method Thereof," filed Nov. 11, 2011; U.S. Pat. No. 8,403,294, issued Mar. 26, 2013.

U.S. patent application Ser. No. 11/665,326 entitled "Electrostatic Actuation for Management of Flow in Micro Total Analysis Systems and Related Method Thereof," filed Apr. 13, 2007; U.S. Pat. No. 8,056,881, issued Nov. 15, 2011

International Patent Application No. US2005/036675 entitled "Electrostatic Actuation for Management of Flow in Micro Total Analysis Systems and Related Method Thereof," filed Oct. 13, 2005.

U.S. patent application Ser. No. 13/699,983 entitled "METHOD FOR DETECTING NUCLEIC ACIDS BASED ON AGGREGATE FORMATION," filed Nov. 26, 2012; U.S. Patent Application Publication No. 2013/0203045, Aug. 8, 2013.

International Patent Application No. PCT/US2011/038166 entitled "METHOD FOR DETECTING NUCLEIC ACIDS BASED ON AGGREGATE FORMATION," filed May 26, 2011.

U.S. patent application Ser. No. 13/474,420 entitled "Passive Components for Micro-Fluidic Flow Profile Shaping and Related Method Thereof," filed May 17, 2012; U.S. Patent Application Publication No. 2012/0222747, Sep. 6, 2012.

U.S. patent application Ser. No. 12/064,557 entitled "Passive Components for Micro-Fluidic Flow Profile Shaping and Related Method Thereof," filed Feb. 22, 2008; U.S. Pat. No. 8,220,493, issued Jul. 17, 2012.

International Patent Application No. PCT/US2006/032717 entitled "Passive Components for Micro-Fluidic Flow Profile Shaping and Related Method Thereof," filed Aug. 23, 2006.

International Patent Application No. PCT/US2012/036105 entitled "METHOD AND SYSTEM FOR HIGH THROUGHPUT OPTICAL AND LABEL FREE DETECTION OF ANALYTES," filed May 2, 2012.

U.S. patent application Ser. No. 14/505,406 entitled "VERSATILE, VISIBLE METHOD FOR DETECTING POLYMERIC ANALYTES," filed May 1, 2012; U.S. Patent Application Publication No. 2013/0084565, Apr. 4, 2013.

U.S. patent application Ser. No. 13/116,659 entitled "METHOD FOR DETECTING NUCLEATED CELLS," filed May 26, 2011.

International Patent Application No. PCT/US2010/002883 entitled "VERSATILE, VISIBLE METHOD FOR DETECTING POLYMERIC ANALYTES," filed Nov. 3, 2010.

U.S. patent application Ser. No. 12/879,810 entitled "DETECTION OF POLYMERIC ANALYTES," filed Sep. 10, 2010; U.S. Patent Application Publication No. 2011/0070660, Mar. 24, 2011.

International Patent Application No. PCT/US2009/036983 entitled "DETECTION OF POLYMERIC ANALYTES," filed Mar. 12, 2009.

U.S. patent application Ser. No. 12/892,618 entitled "DNA EXTRACTION USING A PHOTO-POLYMERIZED MONOLITH IN A CAPILLARY," filed Sep. 28, 2010; U.S. Patent Application Publication No. 2011/0086181, Apr. 14, 2011.

U.S. patent application Ser. No. 11/885,181 entitled "Grafted Photo-Polymerized Monolithic Column," filed Aug. 28, 2007; U.S. Pat. No. 7,815,802, issued Oct. 19, 2010.

International Patent Application No. US2006/006845 entitled "DNA Extraction Using a Photo-Polymerized Monolith in a Capillary," filed Feb. 28, 2006. (01106-03)

U.S. patent application Ser. No. 12/090,233 entitled "Integrated Microfluidic Analysis Systems," filed Apr. 14, 2008.

International Patent Application No. US2006/039809 entitled "Integrated Microfluidic Analysis Systems," filed Oct. 12, 2006.

U.S. patent application Ser. No. 12/089,320 entitled "Microchip-based Acoustic Trapping or Capture of Cells for Forensic Analysis and Related Method Thereof," filed Apr. 4, 2008.

International Patent Application No. PCT/US2006/038943 entitled "Microchip-based Acoustic Trapping or Capture of Cells for Forensic Analysis and Related Method Thereof," filed Oct. 4, 2006.

U.S. patent application Ser. No. 11/989,794 entitled "Microdevices for Chemical Sensing and Chemical Actuation," filed Jan. 31, 2008; U.S. Pat. No. 8,343,755, issued Jan. 1, 2013.

International Patent Application No. PCT/US2006/030127 entitled "Microdevices for Chemical Sensing and Chemical Actuation," filed Aug. 1, 2006.

U.S. patent application Ser. No. 11/793,428 entitled "Use of Microwaves for Thermal and Non-Thermal Applications in Micro and Nanoscale Devices," filed Jan. 7, 2008; U.S. Patent Application Publication No. 2008/0277387, Nov. 13, 2008.)

International Patent Application No. US2005/046756 entitled "The Use of Microwaves for Thermal and Non-Thermal Applications in Micro and Nanoscale Devices," filed Dec. 22, 2005.

International Patent Application No. PCT/US2007/088662 entitled "Non-Contact Thermal Control of Small Volume and Related Apparatus Thereof," filed Dec. 21, 2007.

International Patent Application No. PCT/US2007/083964 entitled "DNA Purification in a Multi-Stage, Multi-Phase Microchip," filed Nov. 7, 2007.

U.S. patent application Ser. No. 11/884,351 entitled "Nucleic Acid Isolation Methods and Materials and Devices Thereof," filed Aug. 15, 2007.

International Patent Application No. PCT/US2006/005241 entitled "Nucleic Acid Isolation Methods and Materials and Devices Thereof," filed Feb. 15, 2006.

U.S. patent application Ser. No. 11/664,297 entitled "Localized Control of Thermal Properties on Microdevices and Applications Thereof," filed Mar. 19, 2007.

International Patent Application No. US2005/034674 entitled "Localized Control of Thermal Properties on Microdevices and Applications Thereof," filed Sep. 29, 2005.

U.S. patent application Ser. No. 10/535,926 entitled "Isolation of Sperm Cells from Other Biological Materials Using Microfabricated Devices and Related Methods Thereof," filed May 23, 2005.

International Patent Application No. US2003/037205 entitled "Isolation of Sperm Cells from Other Biological Materials Using Microfabricated Devices and Related Methods Thereof," filed Nov. 20, 2003.

U.S. patent application Ser. No. 10/530,728 entitled "Methods and Systems for Multiplexing IR-Mediated Heating on a Microchip," filed Apr. 8, 2005.

International Patent Application No. US2003/031806 entitled "Methods and Systems for Multiplexing IR Mediated Heating on a Microchip," filed Oct. 8, 2003.

International Patent Application No. US2005/005490 entitled "Method and System for Eluting Cells," filed Feb. 22, 2005

U.S. patent application Ser. No. 10/520,763 entitled "Hybrid Polymers for Functional Tuning of Microfluidic Device Surfaces," filed Jan. 10, 2005; U.S. Patent No.

International Patent Application No. US2003/022162 entitled "Hybrid Polymers for Functional Tuning of Microfluidic Device Surfaces," filed Jul. 15, 2003.

U.S. patent application Ser. No. 10/517,980 entitled "Apparatus and Method for Purification of Nucleic Acids," filed Dec. 13, 2004; U.S. Pat. No. 7,534,623, issued May 19, 2009

International Patent Application No. US2003/018403 entitled "Apparatus and Method or Purification of Nucleic Acids," filed Jun. 11, 2003.

International Patent Application No. US2004/001276 entitled "Method for Microchip and Capillary Detection of Proteins in the Sub-µG/ML Range," filed Jan. 20, 2004.

U.S. patent application Ser. No. 10/664,064 entitled "Remote Temperature Sensing of Small Volume and Related Apparatus Thereof," filed Sep. 17, 2003.

International Patent Application No. US2003/029249 entitled "Remote Temperature Sensing of Small Volume and Related Apparatus Thereof," filed Sep. 17, 2003.

U.S. patent application Ser. No. 10/432,141 entitled "Method for Orthogonal Analyte Stacking/Injection Systems in Electrophoresis," filed May 16, 2003.

International Patent Application No. US01/43259 entitled "Method For Orthogonal Analyte Stacking/Injection Systems In Electrophoresis," filed Nov. 19, 2001.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the scope of the disclosure, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

The invention claimed is:

1. A centrifugal microfluidic device configured to prepare a sample for nucleic acid analysis, the centrifugal microfluidic device comprising:
    a body formed from of a plurality of layers including a top layer;
    an extraction portion of the body, the extraction portion comprising:
        a first reagent storage chamber; and
        a liberation chamber connected to the first reagent storage chamber;
    a reaction portion of the body comprising:
        a second reagent chamber;
        an aliquot chamber connected to the liberation chamber; and
        a mixing chamber connected to the aliquot chamber and connected to the second reagent chamber;
    a heat and snap-cool portion of the body including a heat and snap-cool chamber connected to the mixing chamber; and
    a separation portion of the body connected to the heat and snap-cool portion of the body, the separation portion comprising:
        a polymer loading reservoir and one or more polymer channels; and
        a separation channel connected to the one or more polymer channels; and
    an electrode connected to the top layer of the body and connected to the separation channel through an opening in the top layer.

2. The centrifugal microfluidic device of claim 1, further comprising:
    a hydrophobic toner valve connected to the mixing chamber.

3. The centrifugal microfluidic device of claim 2, further comprising:
    a hydrophobic membrane filter.

4. The centrifugal microfluidic device of claim 3, wherein the electrode comprises:
    a gold leaf layer;
    an adhesive layer adhered to the gold leaf layer; and
    a transparent layer adhered to adhesive layer.

5. The centrifugal microfluidic device of claim 4, wherein the plurality of layers are adhered by a heat sensitive adhesive.

6. The centrifugal microfluidic device of claim 4, wherein the heat and snap-cool chamber has a length of 6 millimeters, a width of 5 millimeters, and a depth of 300 micrometers.

7. The centrifugal microfluidic device of claim 4, wherein the heat and snap-cool portion is defined at least in part by a PCR layer made of polyester and toner.

8. A centrifugal microfluidic device configured to prepare a sample for nucleic acid analysis, the centrifugal microfluidic device comprising:
- a body formed from of a plurality of layers;
- an extraction portion defined at least in part by a top layer of the body, the top layer made of poly methyl methacrylate, the extraction portion comprising:
  - a first reagent storage chamber; and
  - a liberation chamber connected to the first reagent storage chamber;
- a reaction portion of the body comprising:
  - a second reagent chamber; and
  - a mixing chamber connected to the liberation chamber and connected to the second reagent chamber;
- a heat and snap-cool portion of the body including a heat and snap-cool chamber connected to the mixing chamber; and
- a separation portion connected to the heat and snap-cool portion, the separation portion formed at least in part by a bottom portion of the disc, the separation portion comprising:
  - a polymer loading reservoir and one or more polymer channels; and
  - a separation channel connected to the one or more polymer channels; and
- an electrode connected to the top layer of the body and connected to the separation channel through an opening in the top layer.

9. The centrifugal microfluidic device of claim 8, wherein the separation portion includes a cyclic olefin copolymer layer and a polyester layer connected by pressure-sensitive adhesive.

* * * * *